US011612654B2

(12) United States Patent
Quan et al.

(10) Patent No.: US 11,612,654 B2
(45) Date of Patent: Mar. 28, 2023

(54) COMBINATION THERAPY COMPRISING NIVOLUMAB AND IPILIMUMAB

(71) Applicant: Bristol-Myers Squibb Company, Princeton, NJ (US)

(72) Inventors: Yong Quan, Dublin, CA (US); Vikram Sadineni, Belle Mead, NJ (US); Wallace Kaserer, Lawrence Township, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 406 days.

(21) Appl. No.: 16/723,854

(22) Filed: Dec. 20, 2019

(65) Prior Publication Data

US 2020/0197518 A1 Jun. 25, 2020

Related U.S. Application Data

(60) Division of application No. 15/365,717, filed on Nov. 30, 2016, now Pat. No. 10,512,689, which is a continuation of application No. 15/130,513, filed on Apr. 15, 2016, now abandoned.

(60) Provisional application No. 62/303,855, filed on Mar. 4, 2016, provisional application No. 62/269,000, filed on Dec. 17, 2015, provisional application No. 62/265,268, filed on Dec. 9, 2015, provisional application No. 62/149,325, filed on Apr. 17, 2015.

(51) Int. Cl.
| | |
|---|---|
| *A61K 39/395* | (2006.01) |
| *C07K 16/30* | (2006.01) |
| *C07K 16/28* | (2006.01) |
| *A61K 47/02* | (2006.01) |
| *A61K 47/12* | (2006.01) |
| *A61K 47/18* | (2017.01) |
| *A61K 47/26* | (2006.01) |
| *A61K 39/00* | (2006.01) |

(52) U.S. Cl.
CPC ........ *A61K 39/39591* (2013.01); *A61K 47/02* (2013.01); *A61K 47/12* (2013.01); *A61K 47/18* (2013.01); *A61K 47/183* (2013.01); *A61K 47/26* (2013.01); *C07K 16/28* (2013.01); *C07K 16/2803* (2013.01); *C07K 16/2818* (2013.01); *C07K 16/2878* (2013.01); *C07K 16/30* (2013.01); *C07K 16/303* (2013.01); *C07K 16/3015* (2013.01); *C07K 16/3023* (2013.01); *C07K 16/3038* (2013.01); *C07K 16/3046* (2013.01); *C07K 16/3053* (2013.01); *C07K 16/3069* (2013.01); *A61K 2039/507* (2013.01); *C07K 2317/21* (2013.01); *C07K 2317/76* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 5,821,337 | A | 10/1998 | Carter et al. |
| 5,977,318 | A | 11/1999 | Linsley et al. |
| 6,051,227 | A | 4/2000 | Allison et al. |
| 6,210,669 | B1 | 4/2001 | Aruffo et al. |
| 6,303,121 | B1 | 10/2001 | Kwon |
| 6,355,476 | B1 | 3/2002 | Kwon et al. |
| 6,362,325 | B1 | 3/2002 | Kwon |
| 6,569,997 | B1 | 5/2003 | Kwon |
| 6,682,736 | B1 | 1/2004 | Hanson et al. |
| 6,808,710 | B1 | 10/2004 | Wood et al. |
| 6,887,673 | B2 | 5/2005 | Kunkel et al. |
| 6,905,685 | B2 | 6/2005 | Kwon |
| 6,974,863 | B2 | 12/2005 | Kwon |
| 6,984,720 | B1 | 1/2006 | Korman et al. |
| 7,034,121 | B2 | 4/2006 | Carreno et al. |
| 7,214,493 | B2 | 5/2007 | Kunkel et al. |
| 7,288,638 | B2 | 10/2007 | Jure-Kunkel et al. |
| 7,488,802 | B2 | 2/2009 | Collins et al. |
| 7,595,048 | B2 | 9/2009 | Honjo et al. |
| 7,605,238 | B2 | 10/2009 | Korman et al. |
| 7,812,135 | B2 | 10/2010 | Smith et al. |
| 7,943,743 | B2 | 5/2011 | Korman et al. |
| 8,008,449 | B2 | 8/2011 | Korman et al. |

(Continued)

FOREIGN PATENT DOCUMENTS

| | | |
|---|---|---|
| JP | 2006502116 A | 1/2006 |
| JP | 2008278814 A | 11/2008 |

(Continued)

OTHER PUBLICATIONS

Cantrell et al. Uterine carcinosarcoma: A review of the literature, 2015, Gynecologic Oncology 137:581-588 (Year: 2015).*
Carrington, M. and Norman, P., The KIR Gene Cluster, National Center for Biotechnology Information, United States (2003).
Genbank, "cytotoxic T-lymphocyte-associated protein 4 [*Homo sapiens*]," Accession No. AAB59385.1, accessed at https://www.ncbi.nlm.nih.gov/protein/AAB59385, accessed on Dec. 1, 2016, 2 pages.

(Continued)

*Primary Examiner* — Sharon X Wen
(74) *Attorney, Agent, or Firm* — Sterne, Kessler, Goldstein & Fox P.L.L.C.

(57) ABSTRACT

This provides pharmaceutical compositions that comprise a combination of an anti-cancer agent which is an first antibody and a second antibody. In some embodiments, the first antibody is an anti-Programmed Death-1 (PD-1) antibody. In certain embodiments, the composition is a fixed dose formulation. In certain embodiments, the composition is administered as a flat-dose. The disclosure also provides a kit for treating a subject afflicted with a disease, the kit comprising a dosage of any composition disclosed herein and instructions for using the composition in any of the disclosed methods for treating a disease.

29 Claims, 27 Drawing Sheets

Specification includes a Sequence Listing.

(56) References Cited

U.S. PATENT DOCUMENTS

| | | |
|---|---|---|
| 8,168,179 B2 | 5/2012 | Honjo et al. |
| 8,168,757 B2 | 5/2012 | Finnefrock et al. |
| 8,217,149 B2 | 7/2012 | Irving et al. |
| 8,354,509 B2 | 1/2013 | Carven et al. |
| 8,383,796 B2 | 2/2013 | Korman et al. |
| 8,388,967 B2 | 3/2013 | Smith et al. |
| 8,399,623 B2 | 3/2013 | Terrett et al. |
| 8,609,089 B2 | 12/2013 | Langermann et al. |
| 8,709,424 B2 | 4/2014 | Schebye et al. |
| 8,728,474 B2 | 5/2014 | Honjo et al. |
| 8,779,105 B2 | 7/2014 | Korman et al. |
| 8,900,587 B2 | 12/2014 | Carven et al. |
| 9,067,999 B1 | 6/2015 | Honjo et al. |
| 9,073,994 B2 | 7/2015 | Honjo et al. |
| 9,084,776 B2 | 7/2015 | Korman et al. |
| 9,102,725 B2 | 8/2015 | Korman et al. |
| 9,169,325 B2 | 10/2015 | Keler et al. |
| 9,212,224 B2 | 12/2015 | Cogswell et al. |
| 9,273,135 B2 | 3/2016 | Korman et al. |
| 9,358,289 B2 | 6/2016 | Korman et al. |
| 9,387,247 B2 | 7/2016 | Korman et al. |
| 9,393,301 B2 | 7/2016 | Honjo et al. |
| 9,402,899 B2 | 8/2016 | Honjo et al. |
| 9,439,962 B2 | 9/2016 | Honjo et al. |
| 9,492,539 B2 | 11/2016 | Korman et al. |
| 9,492,540 B2 | 11/2016 | Korman et al. |
| 9,580,505 B2 | 2/2017 | Korman et al. |
| 9,580,507 B2 | 2/2017 | Korman et al. |
| 10,138,299 B2 | 11/2018 | Cogswell et al. |
| 10,512,689 B2 * | 12/2019 | Sadineni ............... A61P 17/00 |
| 2005/0095244 A1 | 5/2005 | Jure-Kunkel et al. |
| 2006/0110383 A1 | 5/2006 | Honjo et al. |
| 2009/0136494 A1 | 5/2009 | Ponath et al. |
| 2009/0311187 A1 | 12/2009 | Berman et al. |
| 2011/0150892 A1 | 6/2011 | Thudium et al. |
| 2012/0263677 A1 | 10/2012 | Eagle et al. |
| 2013/0017199 A1 | 1/2013 | Langermann |
| 2013/0183321 A1 | 7/2013 | Smith et al. |
| 2014/0065152 A1 | 3/2014 | Kwon |
| 2014/0072565 A1 | 3/2014 | Kwon |
| 2014/0072566 A1 | 3/2014 | Kwon |
| 2014/0093511 A1 | 4/2014 | Lonberg et al. |
| 2014/0220002 A1 | 8/2014 | Ponte et al. |
| 2014/0322208 A1 | 10/2014 | Kuhne et al. |
| 2014/0341917 A1 | 11/2014 | Nastri et al. |
| 2014/0348841 A1 | 11/2014 | Schebye et al. |
| 2015/0079109 A1 | 3/2015 | Li et al. |
| 2016/0075782 A1 | 3/2016 | Korman et al. |
| 2016/0304607 A1 | 10/2016 | Sadineni et al. |
| 2016/0362495 A1 | 12/2016 | Korman et al. |
| 2017/0051060 A1 | 2/2017 | Honjo et al. |
| 2017/0088615 A1 | 3/2017 | Korman et al. |
| 2017/0158767 A1 | 6/2017 | Korman et al. |
| 2018/0273624 A1 | 9/2018 | Cogswell et al. |
| 2018/0282414 A1 | 10/2018 | Cogswell et al. |
| 2018/0312590 A1 | 11/2018 | Cogswell et al. |
| 2018/0319887 A1 | 11/2018 | Cogswell et al. |

FOREIGN PATENT DOCUMENTS

| | | |
|---|---|---|
| JP | 2012510468 A | 5/2012 |
| WO | WO-0100244 A2 | 1/2001 |
| WO | WO-2004007520 A2 | 1/2004 |
| WO | WO-2005003168 A2 | 1/2005 |
| WO | WO-2005009465 A1 | 2/2005 |
| WO | WO-2006003179 A2 | 1/2006 |
| WO | WO-2006072625 A2 | 7/2006 |
| WO | WO-2006072626 A1 | 7/2006 |
| WO | WO-2006096491 A2 | 9/2006 |
| WO | WO-2006105021 A2 | 10/2006 |
| WO | WO-2006121168 A1 | 11/2006 |
| WO | WO-2007005874 A2 | 1/2007 |
| WO | WO-2007042573 A2 | 4/2007 |
| WO | WO-2007113648 A2 | 10/2007 |
| WO | WO-2008084106 A1 | 7/2008 |
| WO | WO-2009009116 A2 | 1/2009 |
| WO | WO-2009073533 A2 | 6/2009 |
| WO | WO-2010062896 A1 | 6/2010 |
| WO | WO-2010065939 A1 | 6/2010 |
| WO | WO-2011028683 A1 | 3/2011 |
| WO | WO-2012071411 A2 | 5/2012 |
| WO | WO-2012122444 A1 | 9/2012 |
| WO | WO-2012135408 A1 | 10/2012 |
| WO | WO-2012145493 A1 | 10/2012 |
| WO | WO-2012160448 A2 | 11/2012 |
| WO | WO-2013039954 A1 | 3/2013 |
| WO | WO-2013173223 A1 | 11/2013 |
| WO | WO-2013190555 A1 | 12/2013 |
| WO | WO-2014055648 A1 | 4/2014 |
| WO | WO-2014209804 A1 | 12/2014 |
| WO | WO-2015026684 A1 | 2/2015 |
| WO | WO-2015031667 A2 | 3/2015 |
| WO | WO-2015042246 A1 | 3/2015 |
| WO | WO-2015184099 A1 | 12/2015 |
| WO | WO-2015187835 A2 | 12/2015 |

OTHER PUBLICATIONS

Genbank, "*Homo sapiens* killer cell immunoglobulin like receptor, two Ig domains and long cytoplasmic tail 1 (KIR2DL1), mRNA," Accession No. NM_014218.2, accessed on https://www.ncbi.nlm.nih.gov/nuccore/NM014218, accessed on Dec. 1, 2016, 2 pages.

Genbank, "*Homo sapiens* killer cell immunoglobulin like receptor, two Ig domains and short cytoplasmic tail 2 (KIR2DS2), transcript variant 1, mRNA," Accession No. NM_012312.4, accessed at https://www.ncbi.nlm.nih.gov/nuccore/NM_012312, accessed on Dec. 1, 2016, 2 pages.

Genbank, "*Homo sapiens* natural killer-associated transcript 1 (NKAT1) mRNA, complete cds," Accession No. L41267.1, accessed at https://www.ncbi.nlm.nih.gov/nuccore/L41267, accessed on Dec. 1, 2016, 2 pages.

Genbank, "*Homo sapiens* natural killer-associated transcript 2 (NKAT2) mRNA, complete cds," Accession No. L41268.1, accessed at https://www.ncbi.nlm.nih.gov/nuccore/L41268, accessed on Dec. 1, 2016, 2 pages.

Genbank, "*Homo sapiens* natural killer-associated transcript 3 (NKAT3), complete cds," Accession No. L41269.1, accessed at https://www.ncbi.nlm.nih.gov/nuccore/L41269, accessed on Dec. 1, 2016, 2 pages.

Genbank, "*Homo sapiens* NKAT5-delta-Ig1/Ig2 mRNA, complete cds," Accession No. L76667.1, accessed at https://www.ncbi.nlm.nih.gov/nuccore/L76667, accessed on Dec. 1, 2016, 2 pages.

Genbank, "*Homo sapiens* NKAT6 mRNA, complete cds," Accession No. L76669.1, accessed at https://www.ncbi.nlm.nih.gov/nuccore/L76669, accessed on Dec. 1, 2016, 2 pages.

Genbank, "*Homo sapiens* nkat7 mRNA, complete cds," Accession No. L76670.1, accessed at https://www.ncbi.nlm.nih.gov/nuccore/L76670, accessed on Dec. 1, 2016, 2 pages.

Genbank, "*H. sapiens* mRNA for NK receptor, clone library 15.212," Accession No. X97229.1, accessed at https://www.ncbi.nlm.nih.gov/nuccore/X97229, accessed on Dec. 1, 2016, 2 pages.

Genbank, "*H. sapiens* mRNA for NK receptor (Eb6 ActI)," Accession No. X89892.1, accessed at https://www.ncbi.nlm.nih.gov/nuccore/X89892, accessed on Dec. 1, 2016, 2 pages.

Genbank, "Human hPD-1 (hPD-1) mRNA, complete cds," Accession No. U64863.1, accessed at https://www.ncbi.nlm.nih.gov/nuccore/U64863, accessed on Dec. 1, 2016, 2 pages.

Genbank, "Human p58 natural killer cell receptor precursor mRNA, clone cl-42, complete cds," Accession No. U24076.1, accessed at https://www.ncbi.nlm.nih, gov/nuccore/U24076, accessed on Dec. 1, 2016, 2 pages.

Genbank, "Human p58 natural killer cell receptor precursor mRNA, clone cl-43, complete cds," Accession No. U24075.1, accessed at https://www.ncbi.nlm.nih.gov/nuccore/U24075, accessed on Dec. 1, 2016, 2 pages.

Genbank, "Human p58 natural killer cell receptor precursor mRNA, clone cl-6, complete cds," Accession No. U24074.1, accessed at https://www.ncbi.nlm.nih. gov/nuccore/U24074, accessed on Dec. 1, 2016, 2 pages.

(56) References Cited

OTHER PUBLICATIONS

Genbank, "lymphocyte activation gene 3 protein precursor [*Homo sapiens*]," Accession No. NP 002277.4, accessed at https://www.ncbi.nlm.nih.gov/protein/NP_002277, accessed on Dec. 1, 2016, 2 pages.
Genbank, "lymphocyte activation gene 3 protein precursor [Mus musculus]," Accession No. NP_032505.1, accessed at https://www.ncbi.nlm.nih.gov/protein/NP032505, accessed on Dec. 1, 2016, 2 pages.
Genbank, "natural killer cell Ig-like receptor KIR2DS4 [*Homo sapiens*]," Accession No. AAR26325.1, accessed at https://www.ncbi.nlm.nih.gov/protein/AAR26325, accessed on Dec. 1, 2016, 2 pages.
Genbank, "natural killer cell inhibitory receptor [*Homo sapiens*]," Accession No. AAR16197.1, accessed at https://www.ncbi.nlm.nih.gov/protein/AAR16197, accessed on Dec. 1, 2016, 2 pages.
Genbank, "RecName: Full=Programmed cell death 1 ligand 1; Short=PD-L1; Short=PDCD1 ligand 1; Short-Programmed death ligand 1; AltName: Full-B7 homolog 1; Short=B7-H1; AltName: CD_antigen=CD274; Flags: Precursor," Accession No. Q9NZQ7.1, accessed at https://www.ncbi.nlm.nih.gov/protein/Q9NZQ7, accessed on Dec. 1, 2016, 2 pages.
Genbank, "tumor necrosis factor receptor superfamily member 18 isoform 1 precursor [*Homo sapiens*]," Accession No. NP_004186.1, accessed at https://www.ncbi.nlm.nih.gov/protein/NP_004186, accessed on Dec. 1, 2016, 2 pages.
Genbank, "tumor necrosis factor receptor superfamily member 18 isoform 2 precursor [*Homo sapiens*]," Accession No. NP_683699.1, accessed at https://www.ncbi.nlm.nih.gov/protein/NP683699, accessed on Dec. 1, 2016, 2 pages.
Genbank, "tumor necrosis factor receptor superfamily member 18 isoform 3 precursor [*Homo sapiens*]," Accession No. NP 683700.1, accessed at https://www.ncbi.nlm.nih.gov/protein/NP683700, accessed on Dec. 1, 2016, 2 pages.
Genbank, "tumor necrosis factor receptor superfamily member 9 precursor [*Homo sapiens*]," Accession No. NP_001552.2, accessed at https://www.ncbi.nlm.nih.gov/protein/NP001552, accessed on Dec. 1, 2016, 2 pages.
Herbst, R.S., et al., "A Study of MPDL3280A, an Engineered PD-L1 Antibody in Patients with Locally Advanced or Metastatic Tumors," *Journal of Clinical Oncology* 31 (*Suppl*):Abstract 3000, American Society of Clinical Oncology, United States (2013).
Jang, I.K., et al., "Human 4-1BB (CD137) Signals are Mediated by TRAF2 and Activate Nuclear Factor-Kappa B," *Biochemical and Biophysical Research Communications* 242(3):613-620, Academic Press, United States (1998).
Khleif, S., et al., "MEDI4736, an anti-PD-L1 antibody with modified Fc domain: Preclinical evaluation and early clinical results from a phase 1 study in patients with advanced solid tumors," Abstract 802, Proceedings from the European Cancer Congress, Amsterdam, Netherlands (Sep. 27, 2013-Oct. 1, 2013).

National Cancer Institute, "anti-PD-1 fusion protein AMP-224," accessed at http://www.cancer.gov/drugdictionarv?cdrid=695789, accessed at Dec. 1, 2016, 3 pages.
National Cancer Institute, "ant-PD-1 monoclonal antibody MEDI0680," accessed at http://www.cancer.gov/drugdictionary?cdrid=756047, accessed at Dec. 1, 2016, 3 pages.
National Cancer Institute, "pembrolizumab," accessed at http://www.cancer.gov/publications/dictionaries/cancer-drug?cdrid=700595, accessed at Dec. 1, 2016, 3 pages.
Nocentini, G., et al., "A New Member of the Tumor Necrosis Factor/Nerve Growth Factor Receptor Family inhibits T Cell Receptor-induced Apoptosis," *Proceedings of the National Academy of Sciences of the United States of America* 94(12):6216-6221, National Academy of Sciences, United States (1997).
Schaer, D.A., et al., "Modulation of GITR for Cancer Immunotherapy," *Current Opinion in Immunology* 24(2):217-224, Elsevier Ltd., England (2012).
Sjoblom, T., et al., "The Consensus Coding Sequences of Human Breast and Colorectal Cancers," *Science* 314(5797):268-274, American Association for the Advancement of Science, United States (2006).
Wang, C., et al., "In Vitro Characterization of the Anti-PD-1 Antibody Nivolumab, BMS-936558, and in Vivo Toxicology in Non-Human Primates," *Cancer Immunology Research* 2(9):846-856, American Association for Cancer Research, United States (May 28, 2014).
International Search Report and Written Opinion for International Application No. PCT/US2016/027913, European Patent Office, Netherlands, dated Jul. 7, 2016, 11 pages.
Uchiyama, S., et al., "Liquid formulation for antibody drugs," Biochimica et Biophysica Act (BBA)—Proteins and Proteomics 1844(11):2041-2052, Elsevier, Netherlands (Aug. 13, 2014).
Wolchok, J. D., et al. "Nivolumab plus ipilimumab in advanced melanoma." N Engl J Med 369 (2013): 122-133, Massachusetts Medical Society, United States (2013).
OPDIVO Package Insert, Bristol-Myers Squibb, Revised Jun. 2020.
U.S. Food Drug Administration, "Highlights of Prescribing Information Reference ID: 3677021", U.S. FDA, (2014), URL: https://www.accessdata.fda.gov/drugsatfda_docs/label/2014/125554lbl.pdf.
European Medicines Agency "Assessment Report For Yervoy (ipilimumab) Procedure No. EMEA/H/C/002213", pp. 1-71, URL: https://www.ema.europa.eu/en/documents/assessment-report/yervoy-epar-public-assessment-report_en.pdf.
Shire, S. "Formulation of proteins and monoclonal antibodies mAbs," in *Monoclonal Antibodies: Meeting The Challenges In Manufacturing, Formulation, Delivery And Stability Of Final Drug Product*, pp. 93-120 (Apr. 24, 2015).
Package Insert, "OPDIVO I.V. Infusion 20 mg, OPDIVO I.V. Infusion 100 mg, OPDIVO I.V. Infusion 240 mg," 11 pages (Sep. 2014).
English language translation of Office Action for Japanese Patent Application No. 2017554282, dated Apr. 23, 2020, mailed May 12, 2020, 4 pages.

* cited by examiner

Fig. 1: Commercial Formulations of Ipilimumab and Nivolumab

| Ipilimumab Composition | DS | DP |
|---|---|---|
| Type | IgG1; Mol. Wt.: 147,991 Daltons | |
| pI: | 8.7-8.8 | |
| BMS-734016 | 5 mg/ml | 5 mg/ml |
| Tris HCl, USP | 20 mM | 20 mM |
| pH | 7.0 | 7.0 |
| Sodium Chloride, USP | 100 mM | 100 mM |
| Mannitol (%w/v), USP | 1.0 % | 1.0% |
| Pentetic Acid (DTPA), USP | 100 µM | 100 µM |
| Polysorbate 80, NF | 0.01 % | 0.01% |
| Strengths (fill volumes): 50 mg (10 mL in a 10 mL vial) and 200 mg (40 mL in a 50 mL vial) DP Unit Ops: Fill, Finish | | |

| Nivolumab Composition | DS | DP |
|---|---|---|
| Type | IgG4; Mol. Wt.: 143,567 Daltons | |
| pI: | 8.0-8.1 | |
| BMS-936558 | 20 mg/ml | 10 mg/ml |
| Sodium Citrate Dihydrate, USP | 20 mM | 20 mM |
| pH | 6.0 | 6.0 |
| Sodium Chloride, USP | 50 mM | 50 mM |
| Mannitol (%w/v), USP | 3.0 % | 3.0 % |
| Pentetic Acid (DTPA), USP | 20 µM | 20 µM |
| Polysorbate 80, NF | 0.04 % | 0.02 % |
| Strength (fill volume): 100 mg (10 mL in a 10 mL vial) DP Unit Ops: Dilute, Fill, Finish | | |

DS: Drug Substance; DP: Drug Product

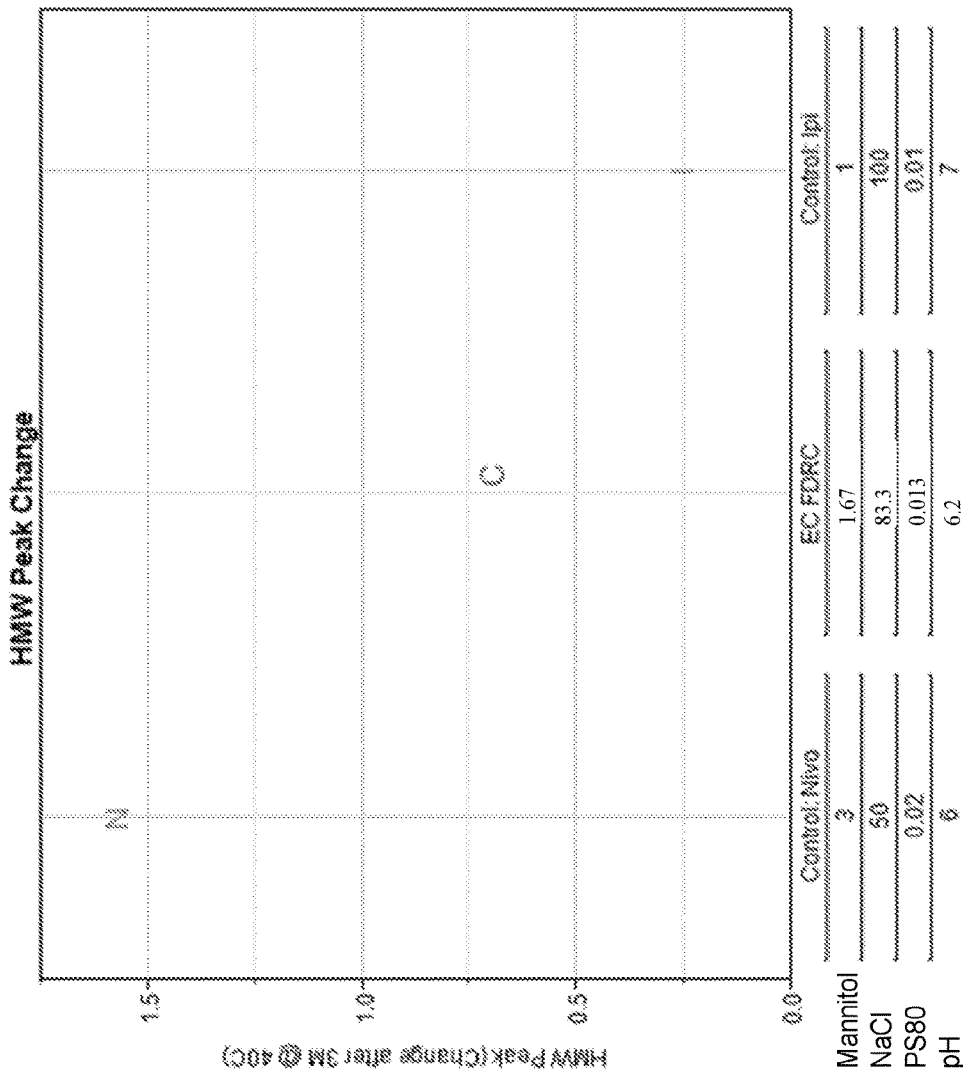
Fig. 2A: 1:1 Ratio Fixed Dosing Formulation for Nivolumab and Ipilimumab HMW Profile Change (3M at 40°C)

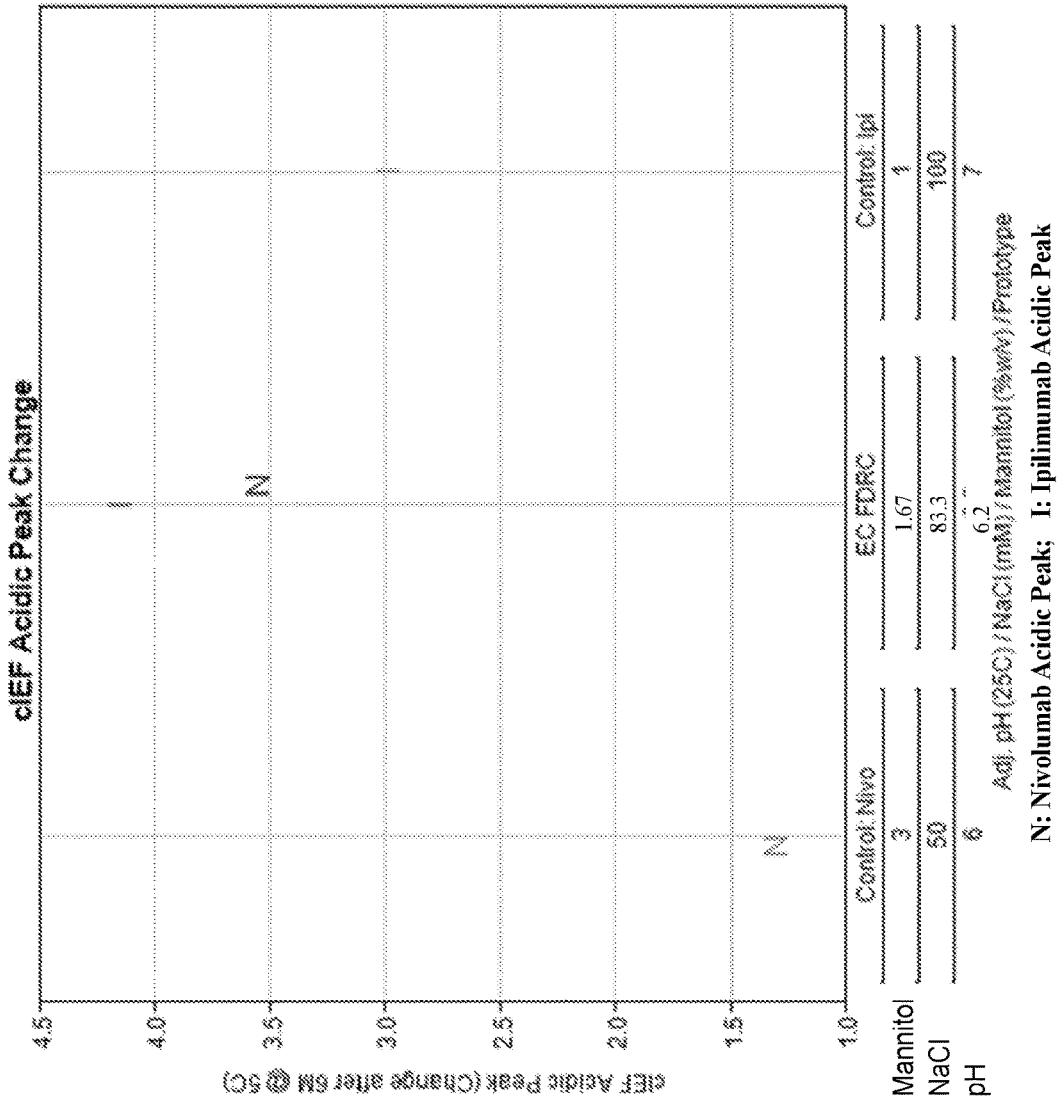
Fig. 2B: 1:1 Ratio Fixed Dosing Formulation for for Nivolumab and Ipilimumab Charge Profile Change (cIEF) (6M at 5°C)

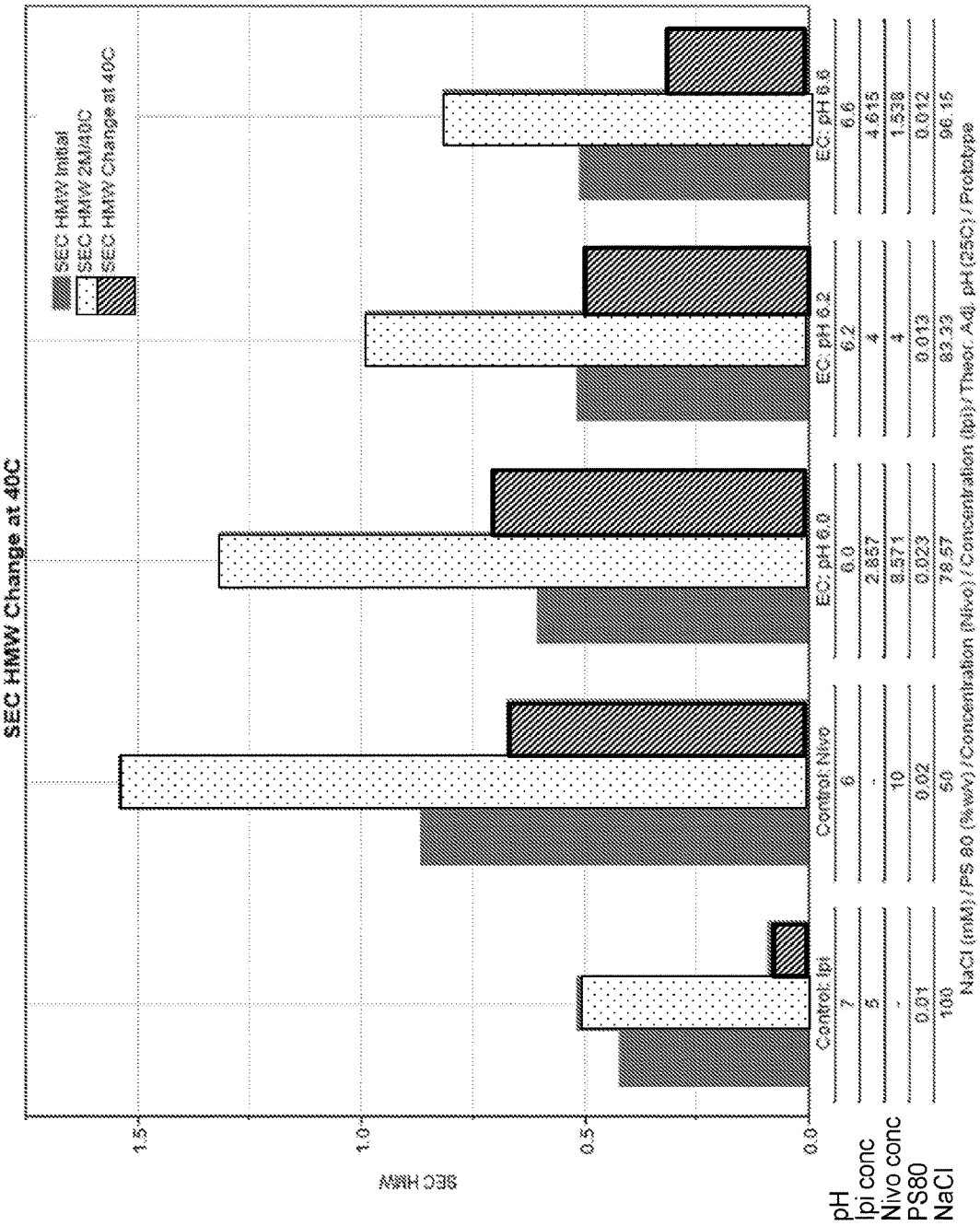
Fig. 3A: 1:3, 1:1, or 3:1 Ratio Fixed Dosing Formulations for Nivolumab and Ipilimumab: HMW Profile Change (2M at 40°C)

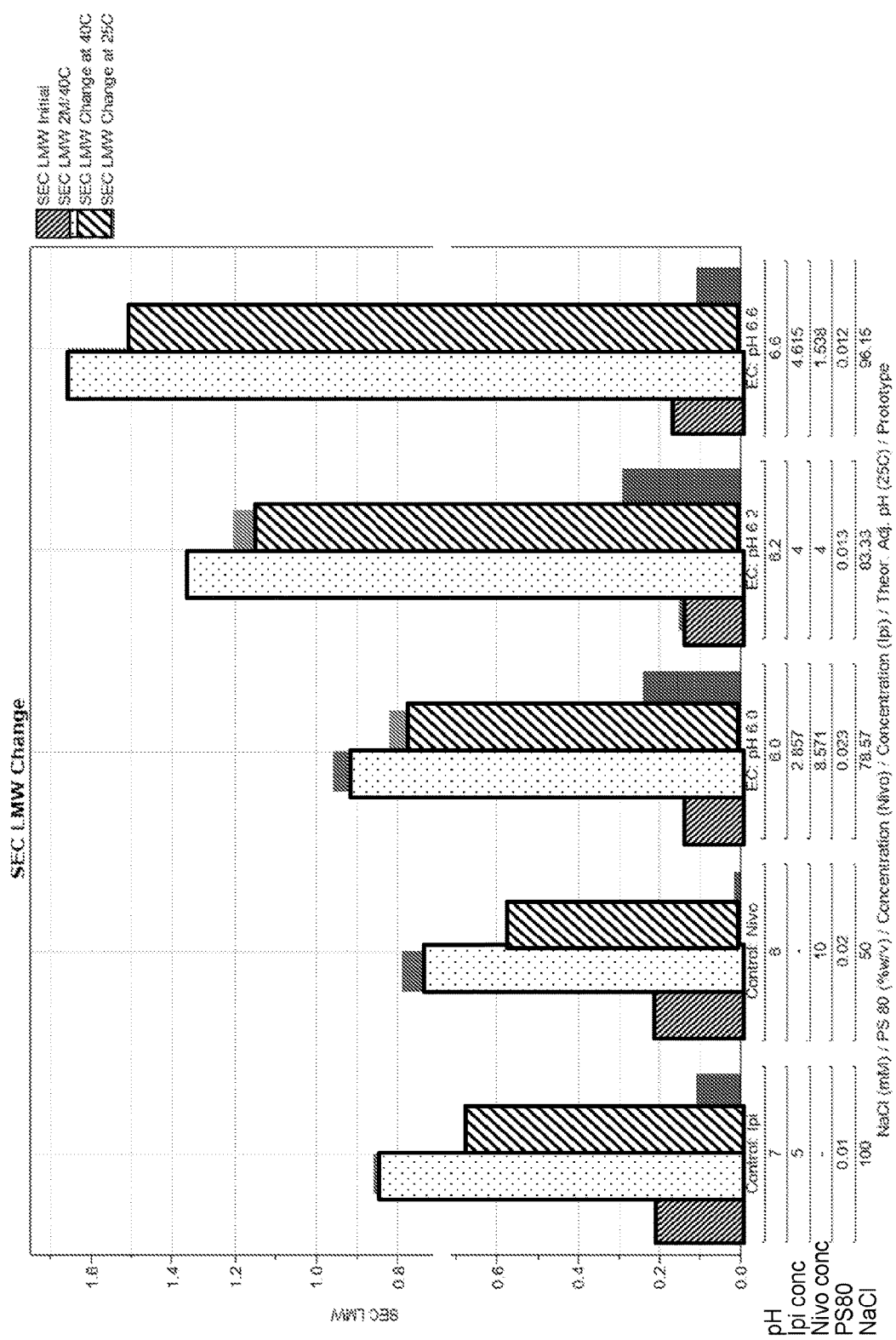

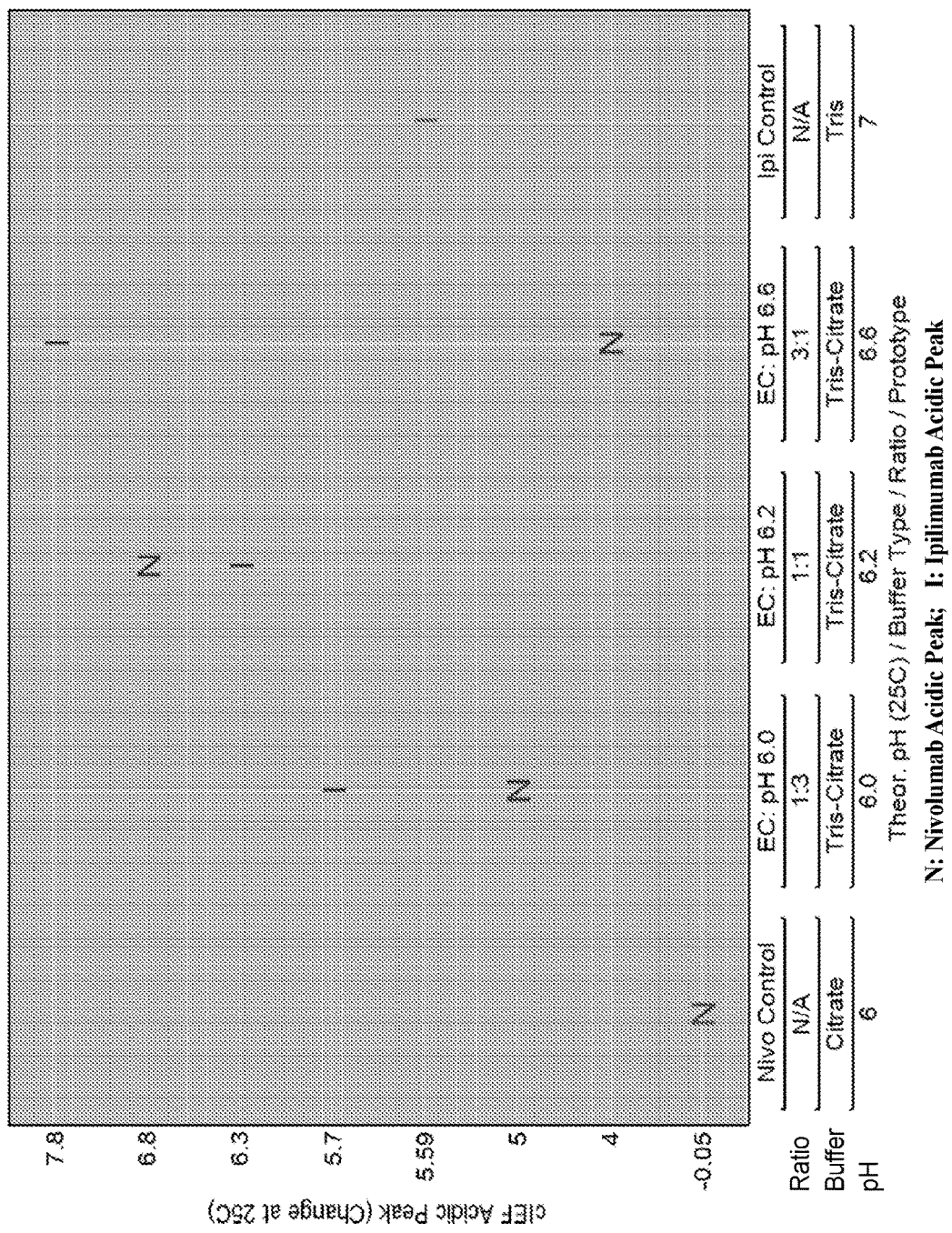

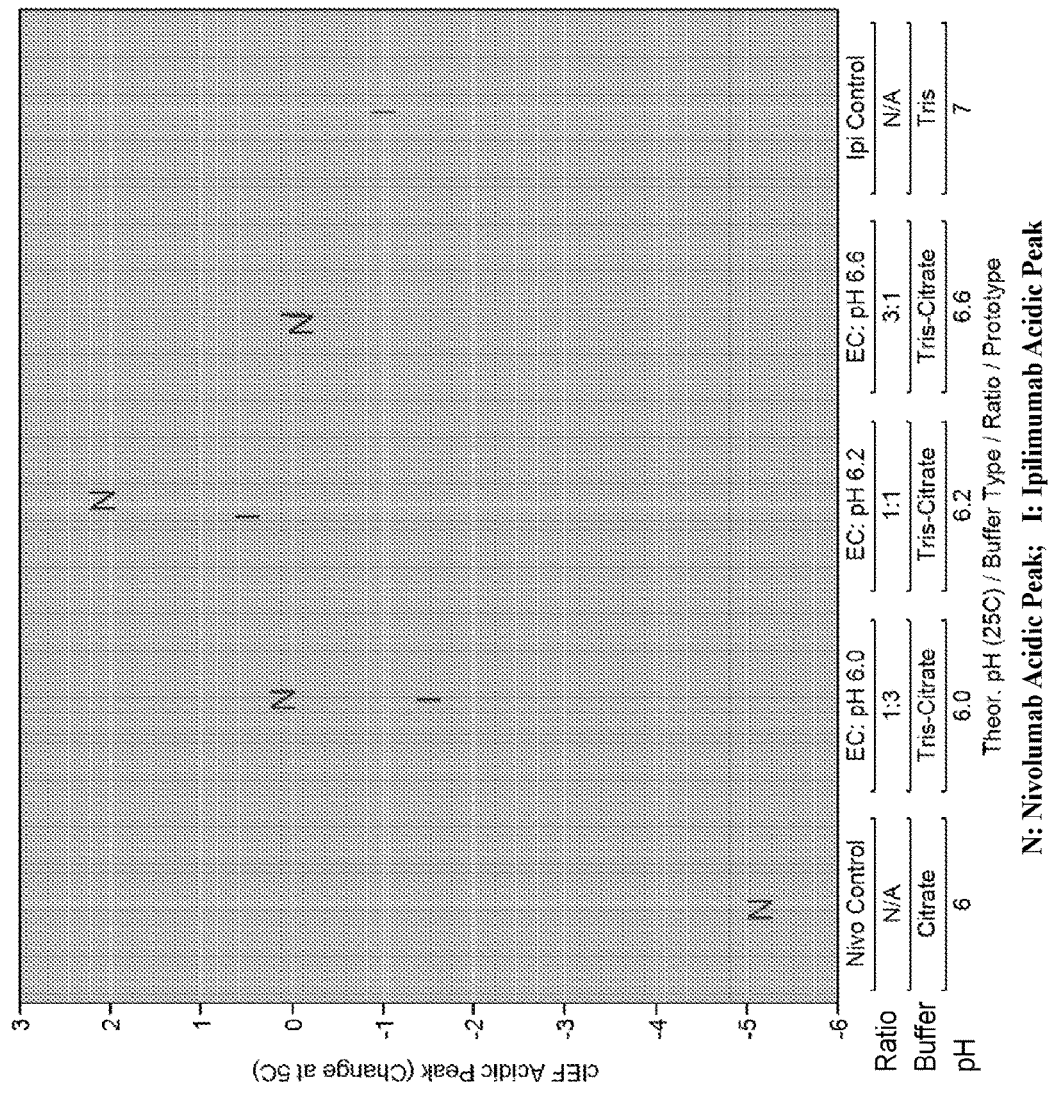

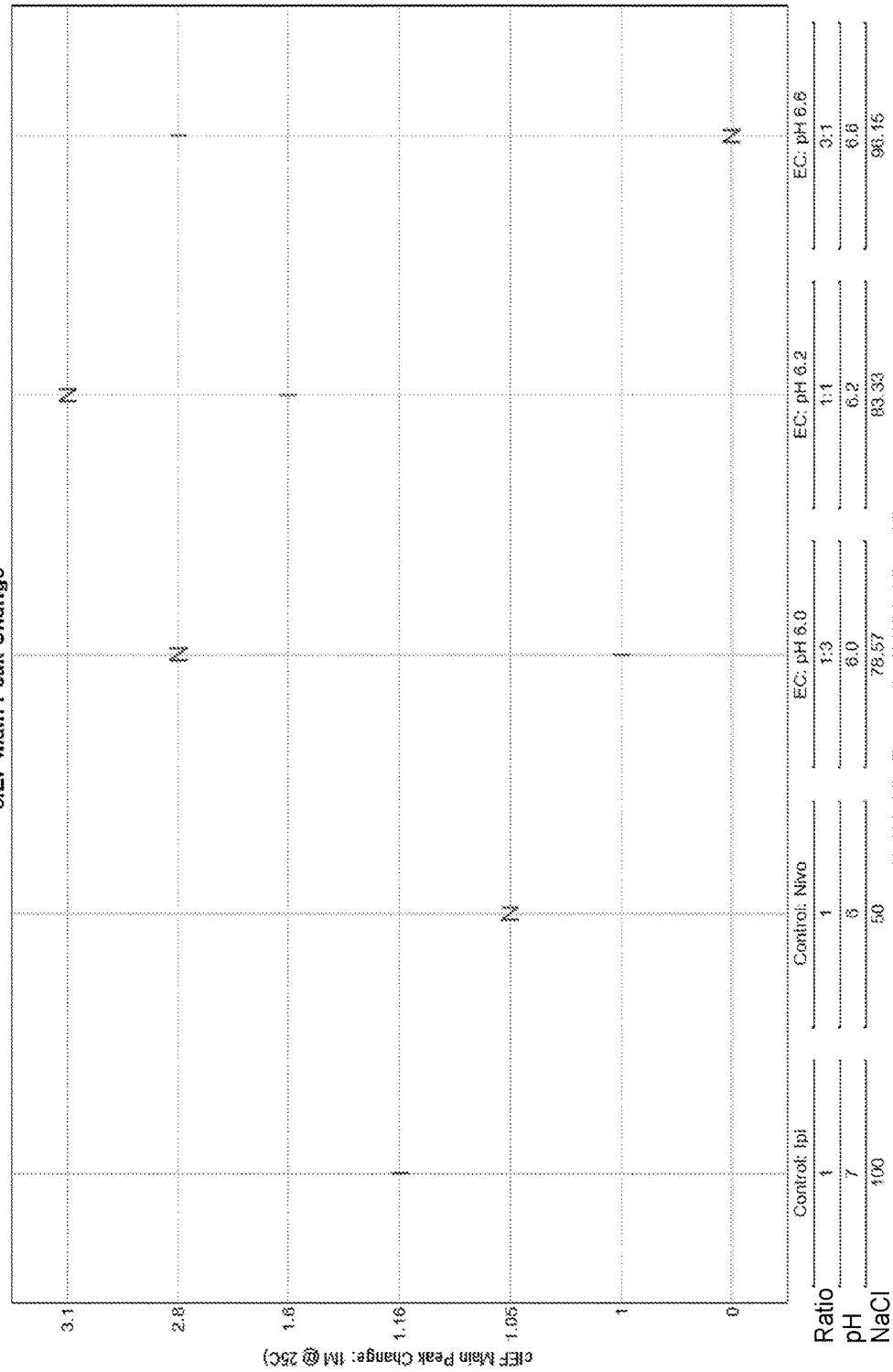

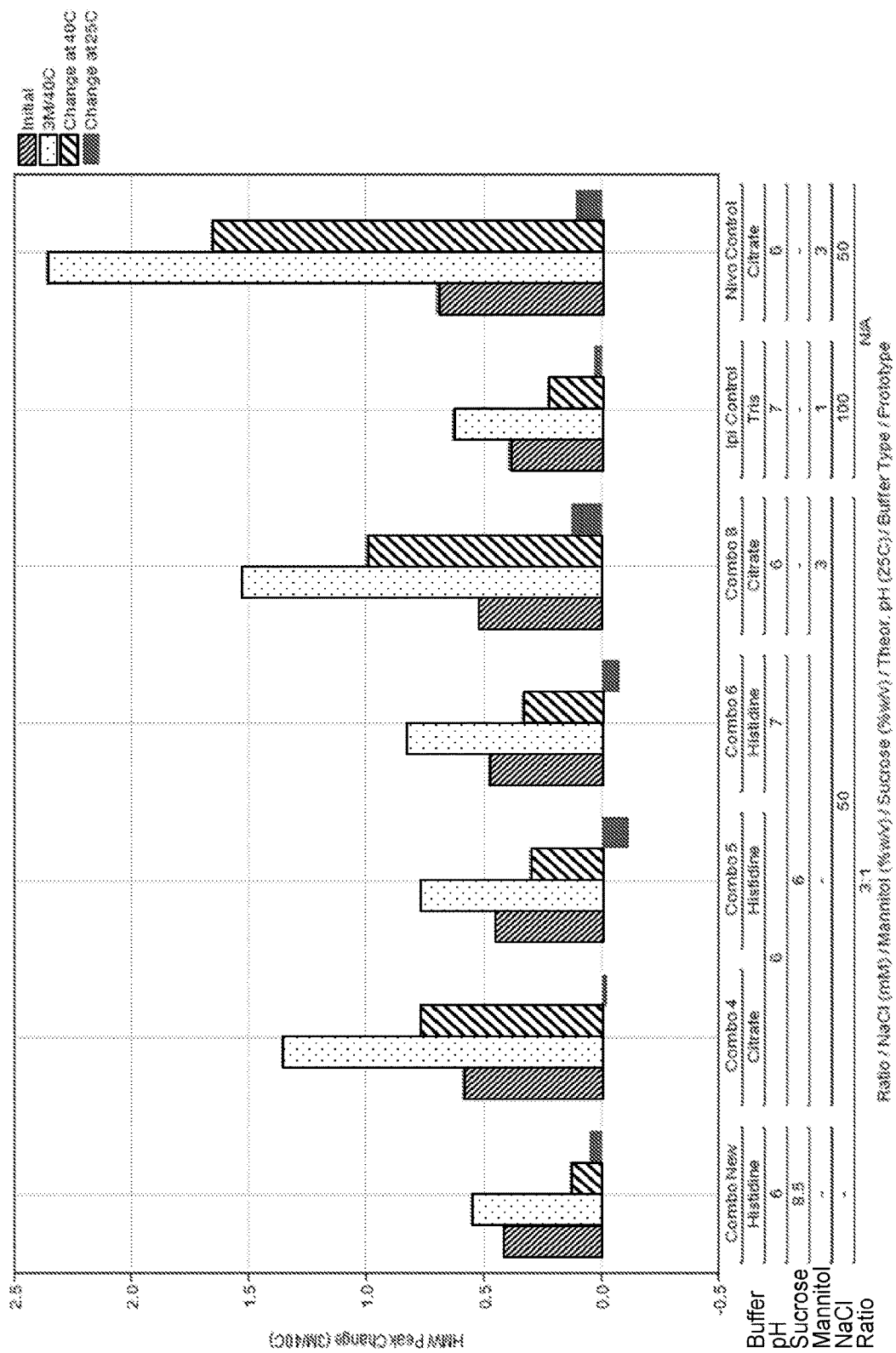

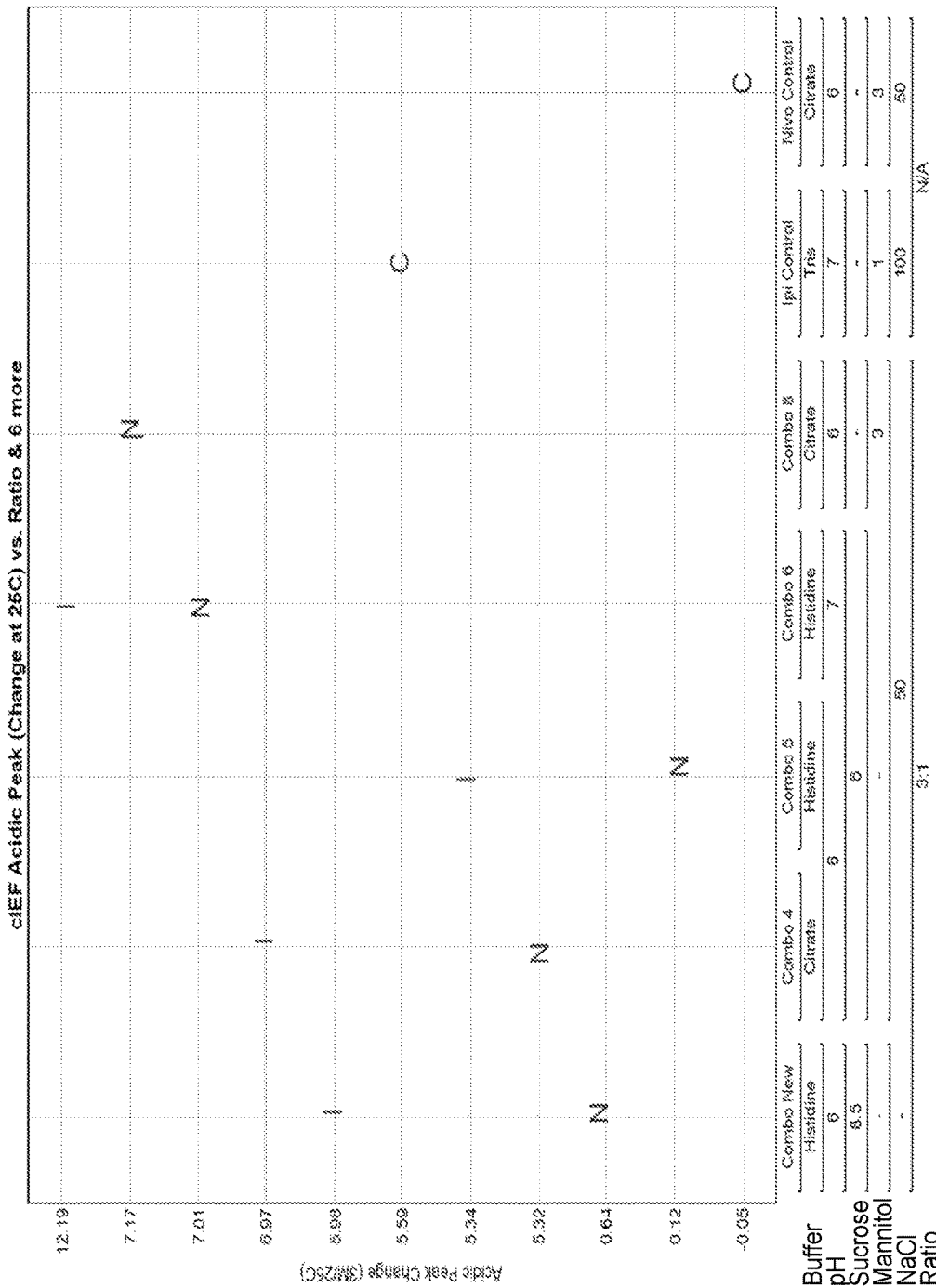

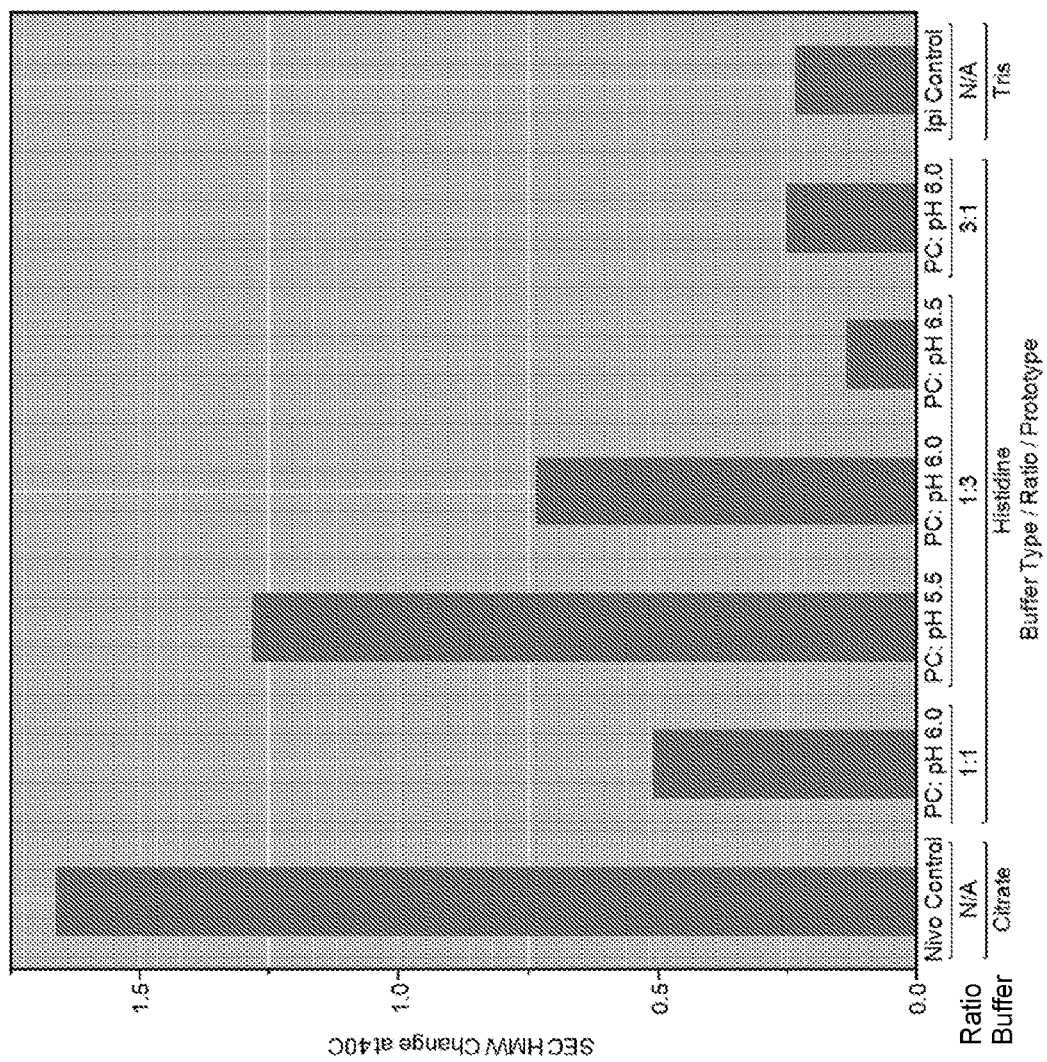

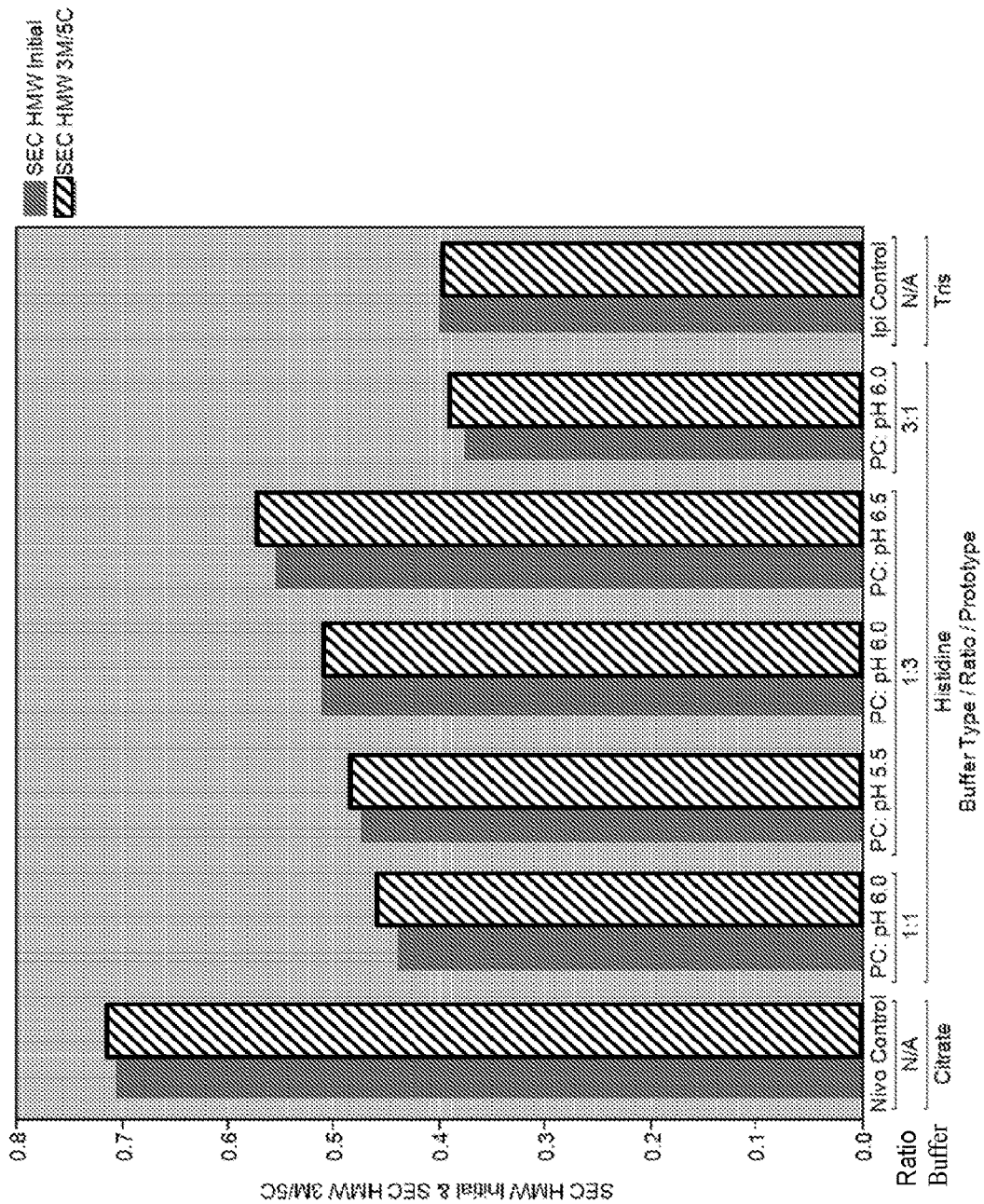

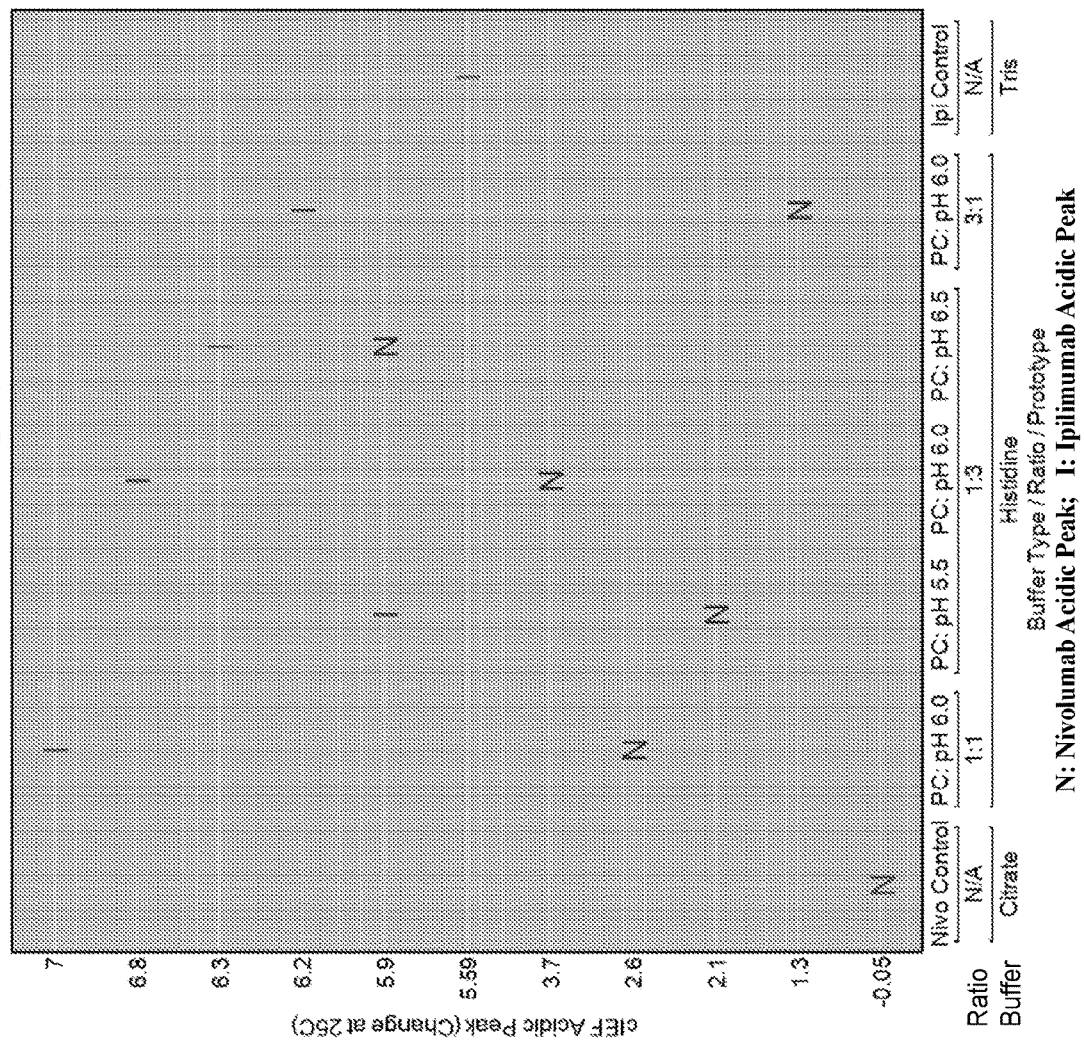

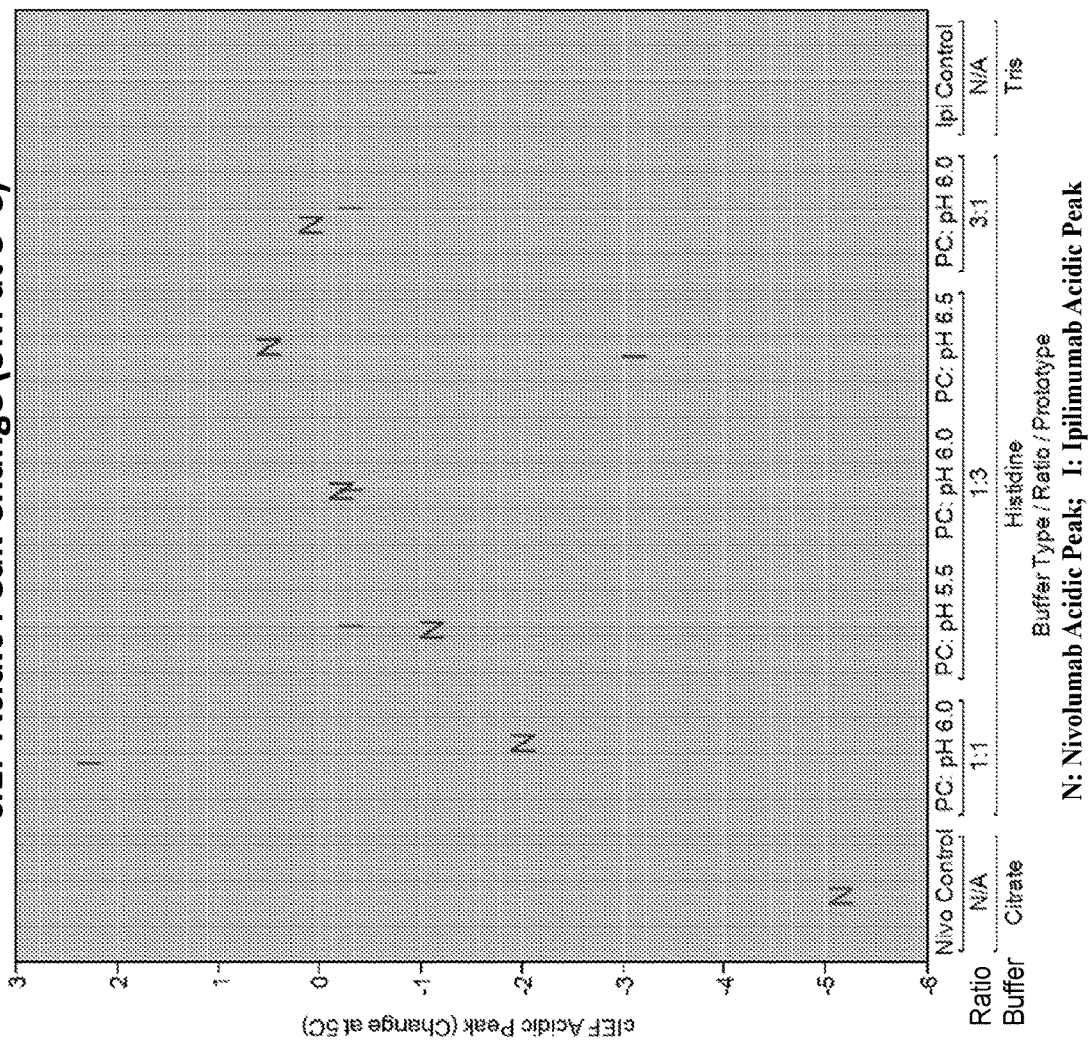

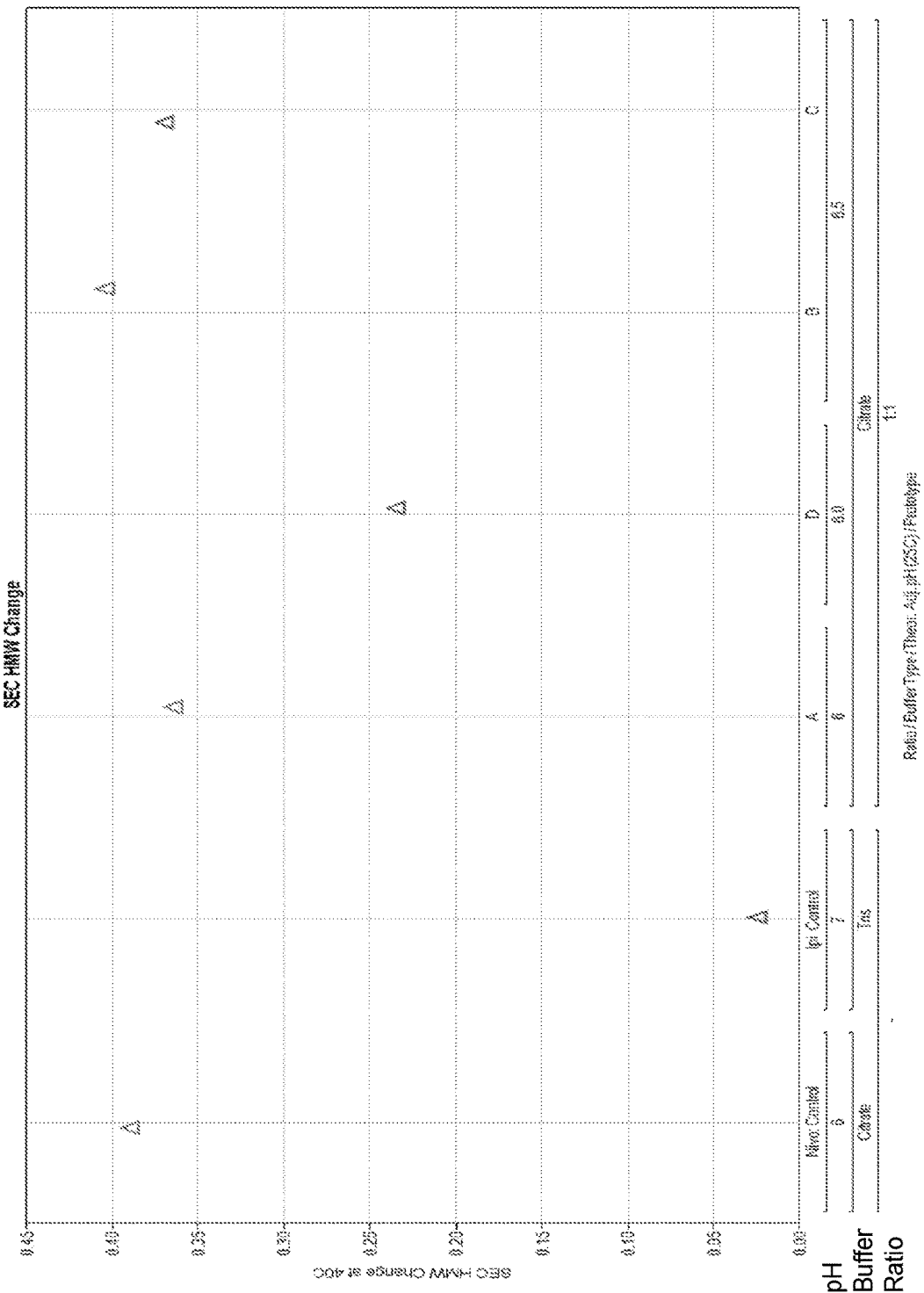

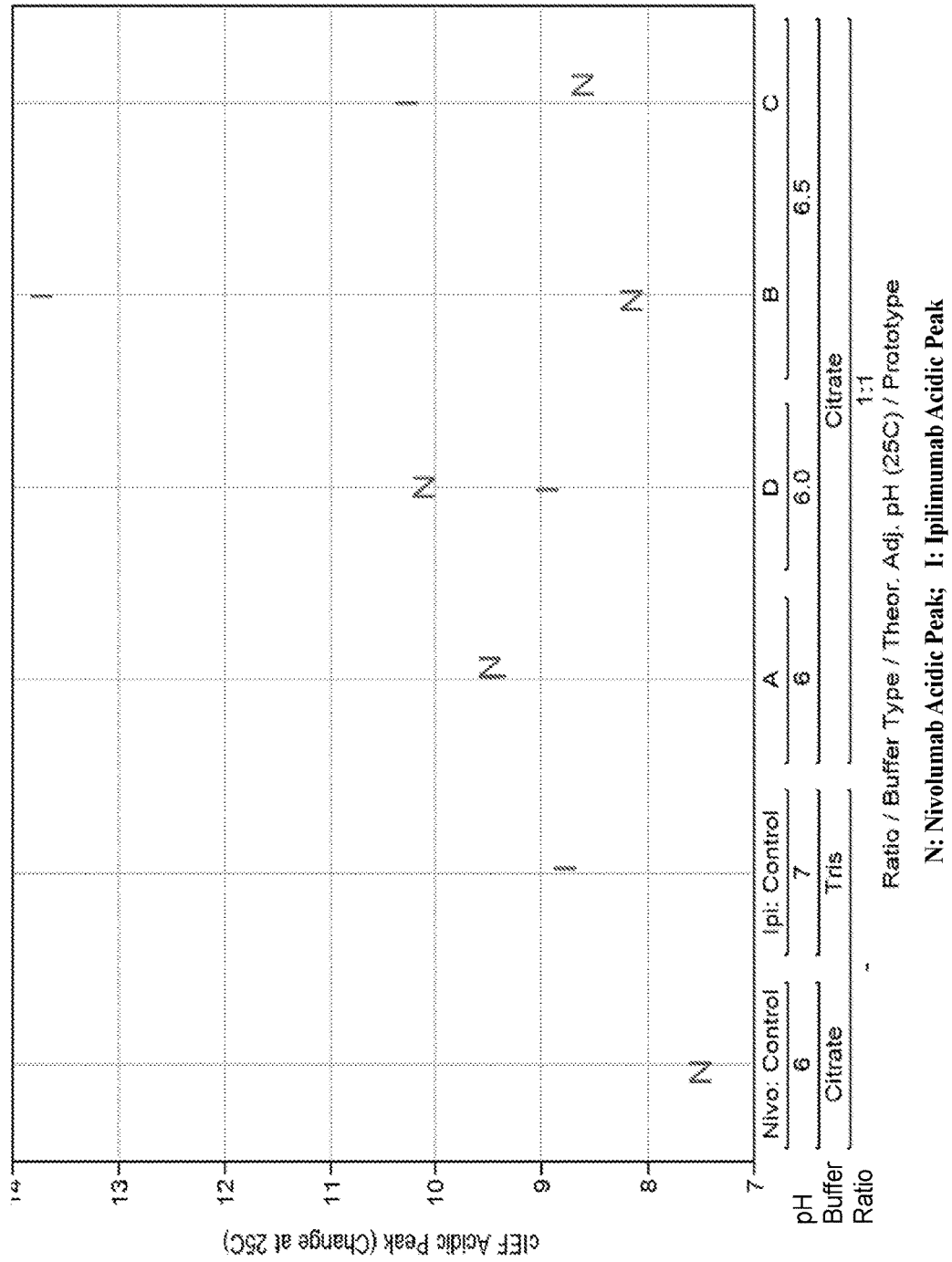

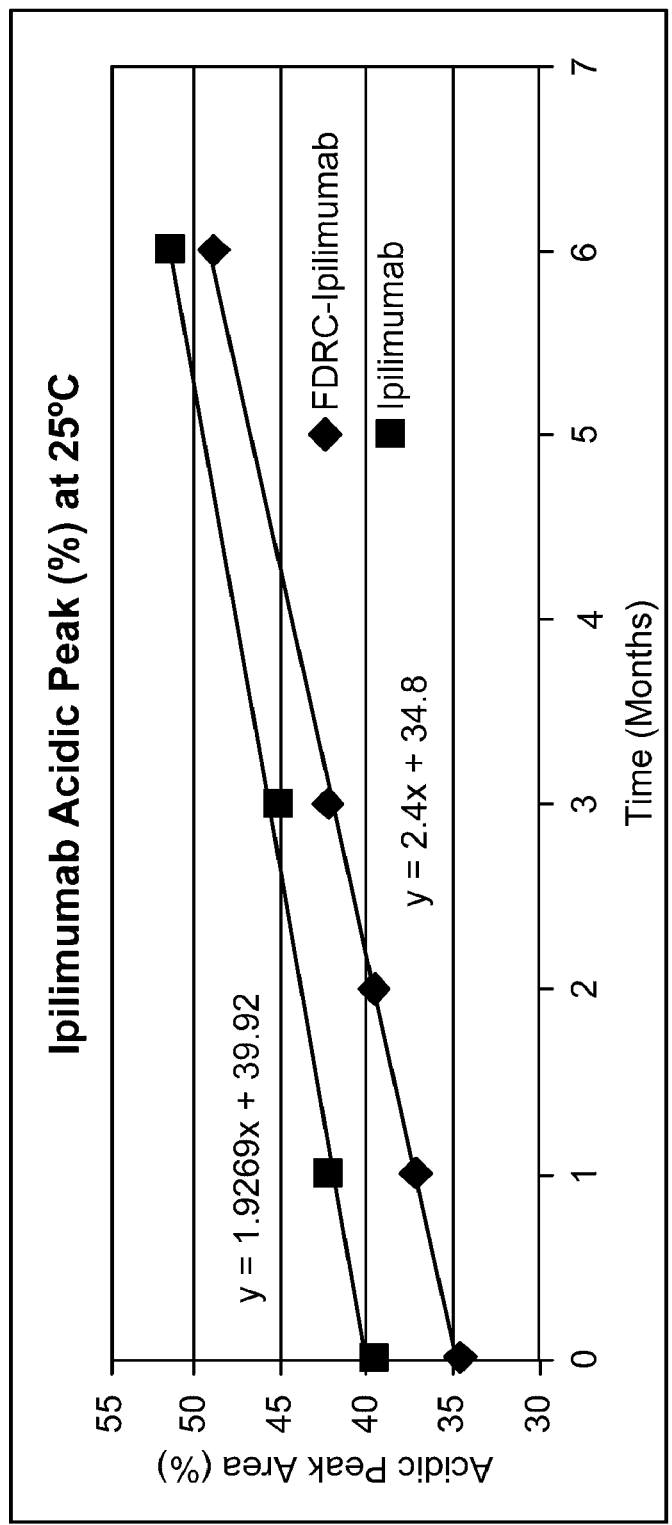
Fig. 10: Ipilimumab Acidic Peak Degradation Rate in FDRC and Commercial Composition at 25°C/60%RH

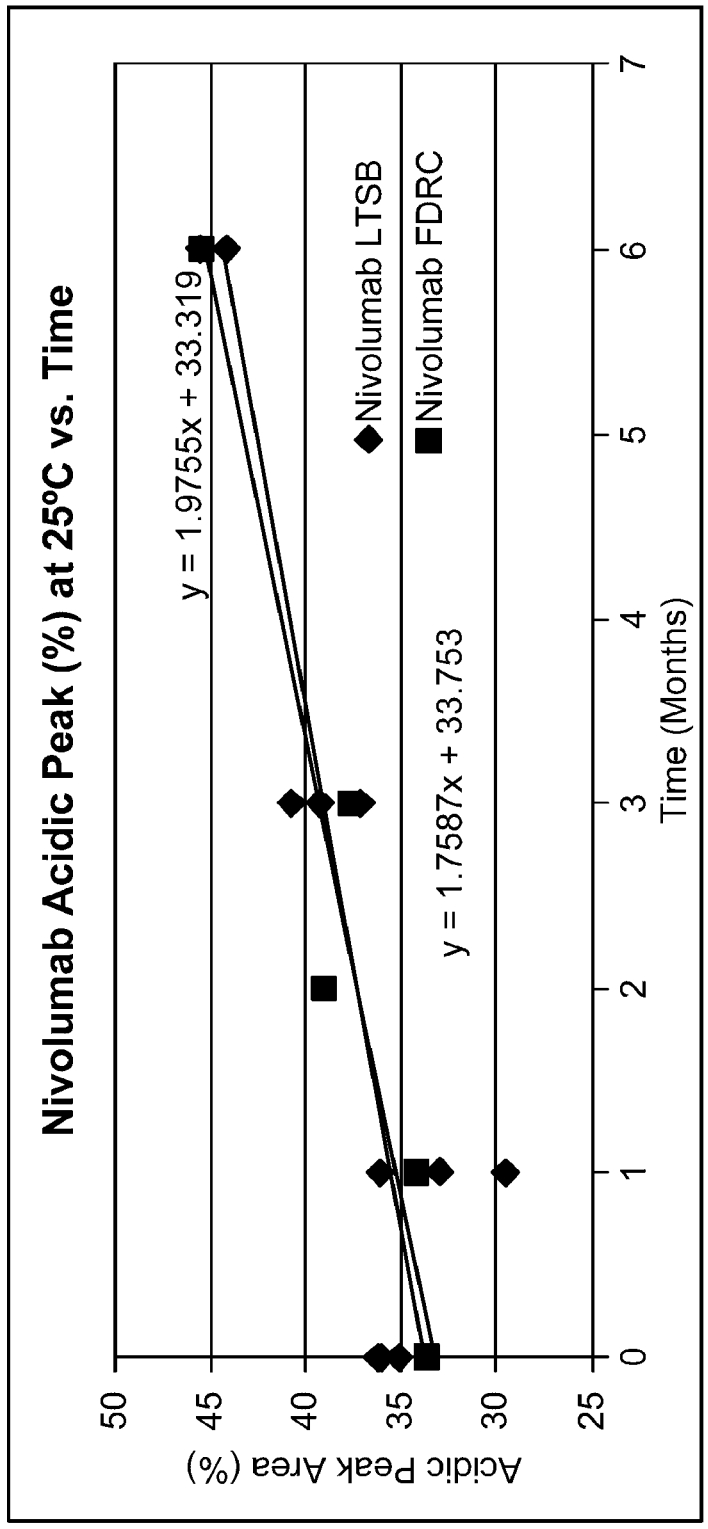
Fig. 11: Nivolumab Acidic Peak (%) in FDRC and Commercial Composition at 25°C/60%RH

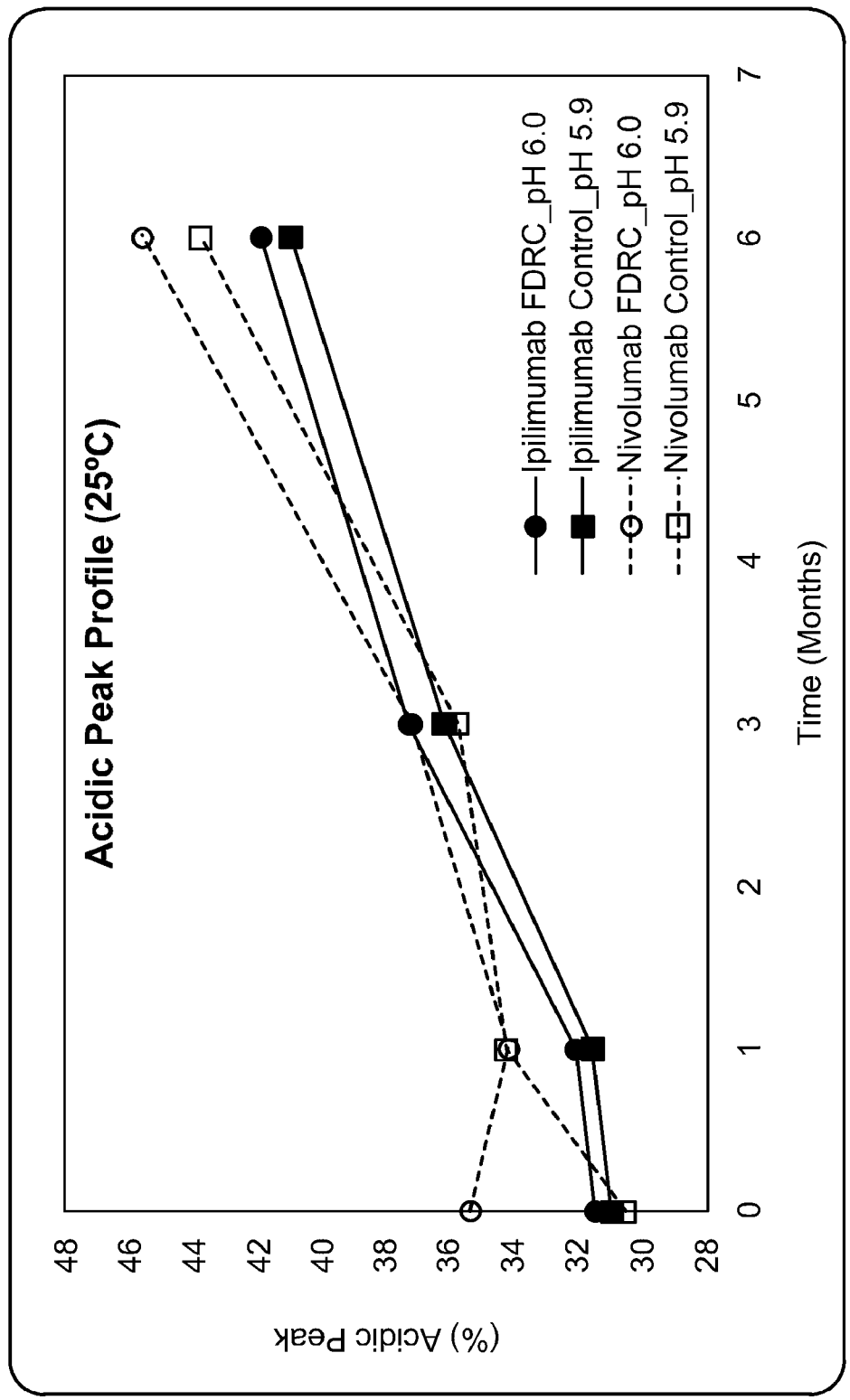
Fig. 12: Acidic Peak Profile at 25°C in pH ranging Study for Ipilimumab and Nivolumab

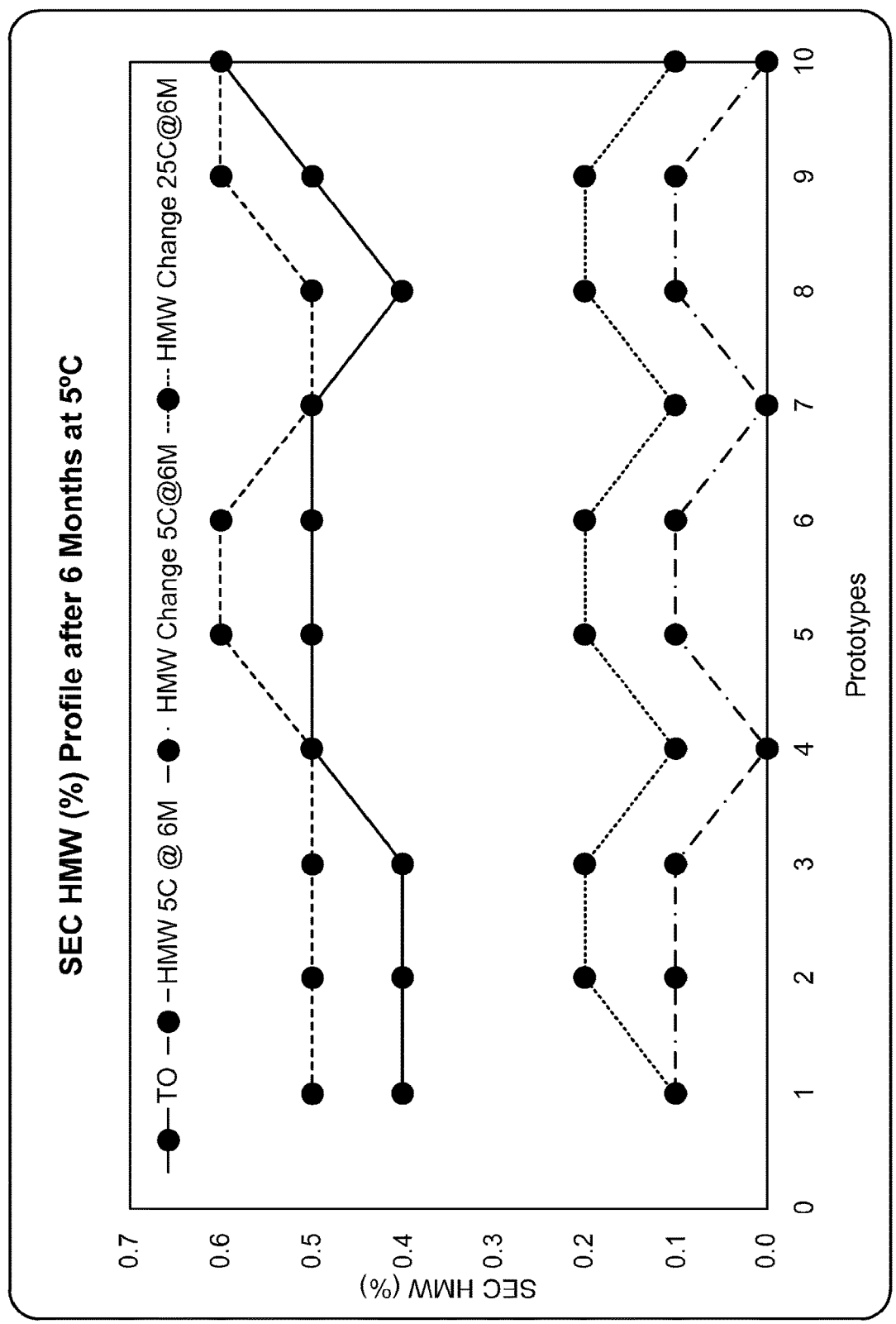
Fig. 13: SEC HMW Profile of DP Prototypes from Ruggedness Study

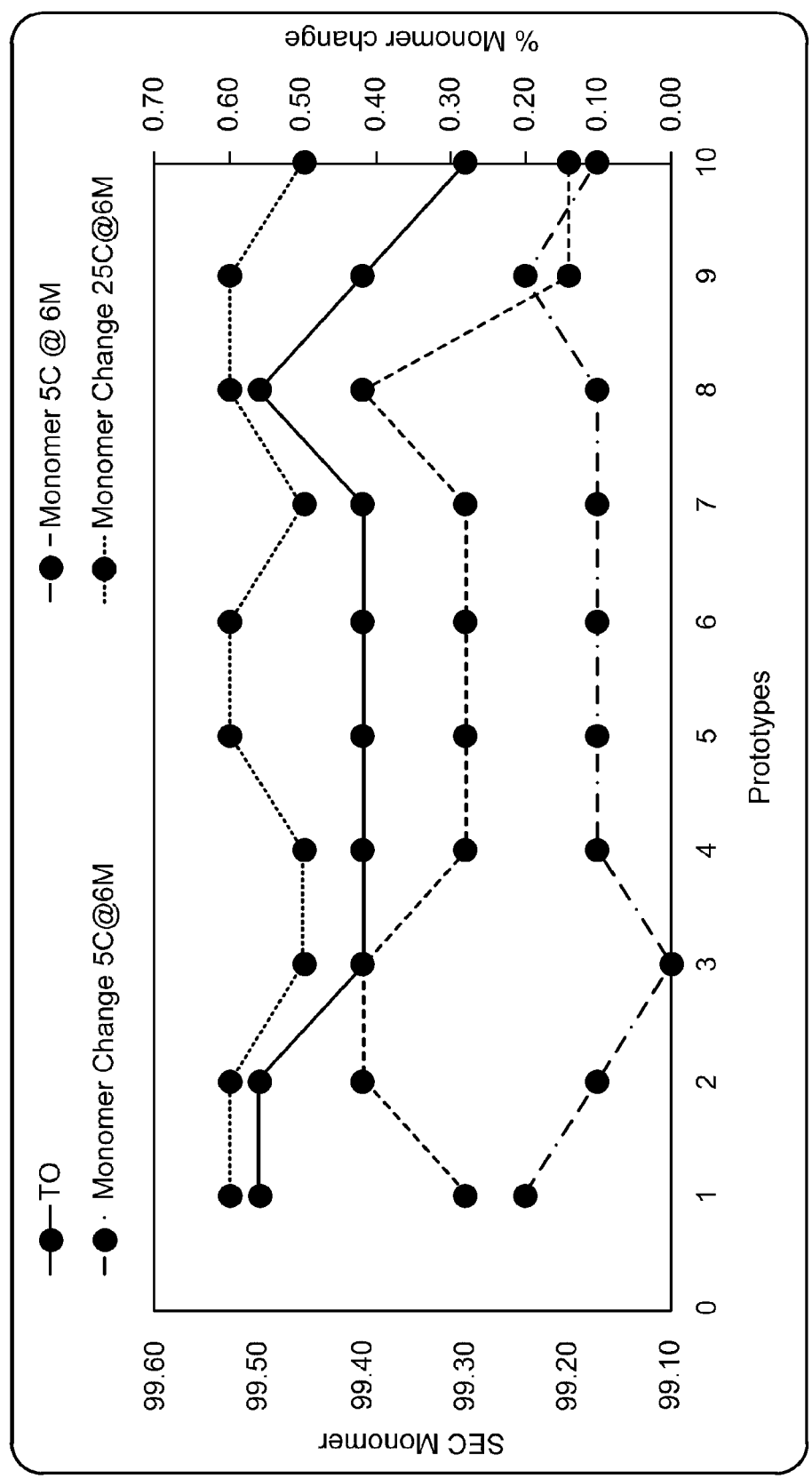
Fig. 14: SEC Monomer Profile

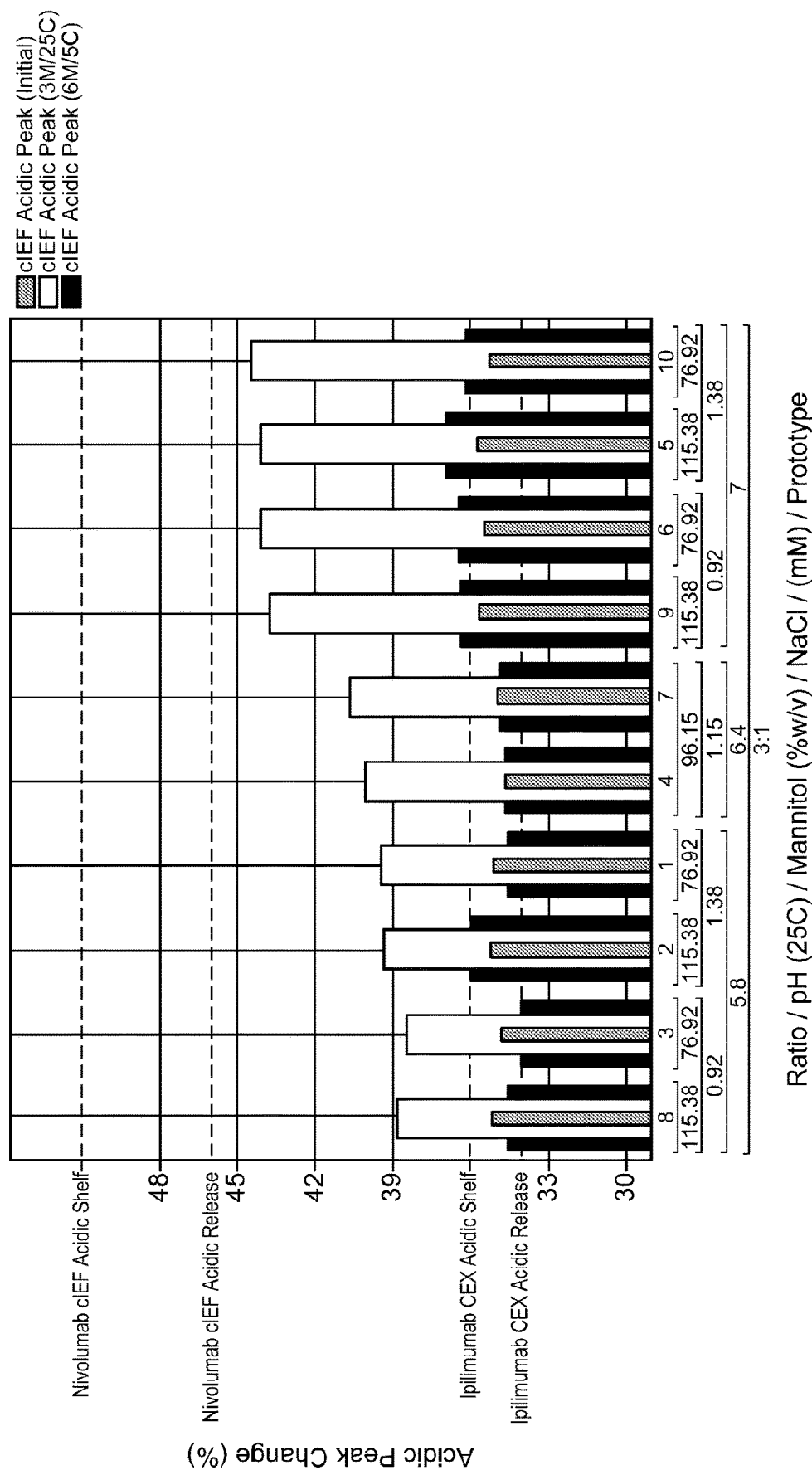
Fig. 15: Ipilimumab Acidic Peak Profile

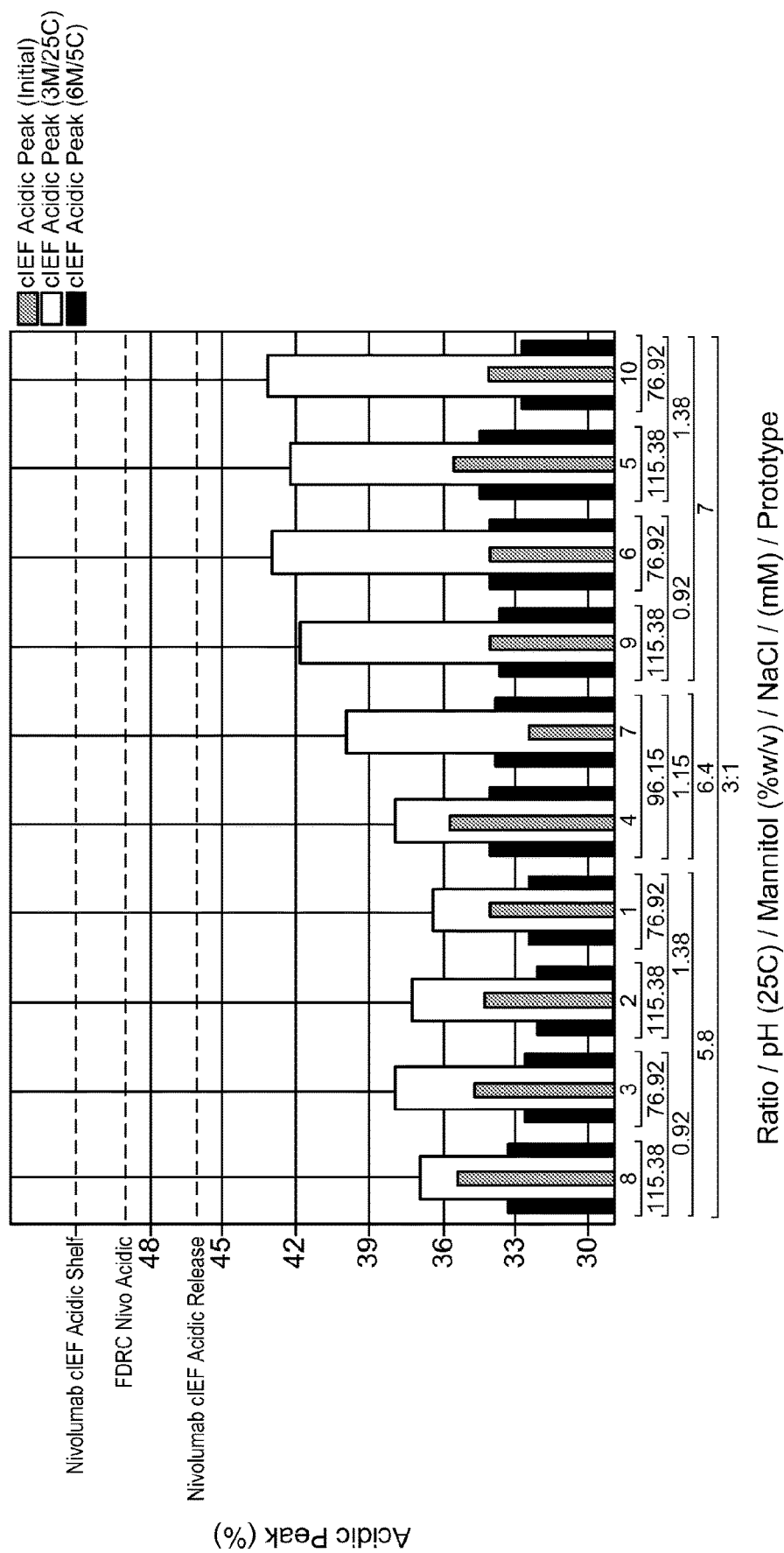
Fig. 16: Nivolumab Acidic Peak Profile

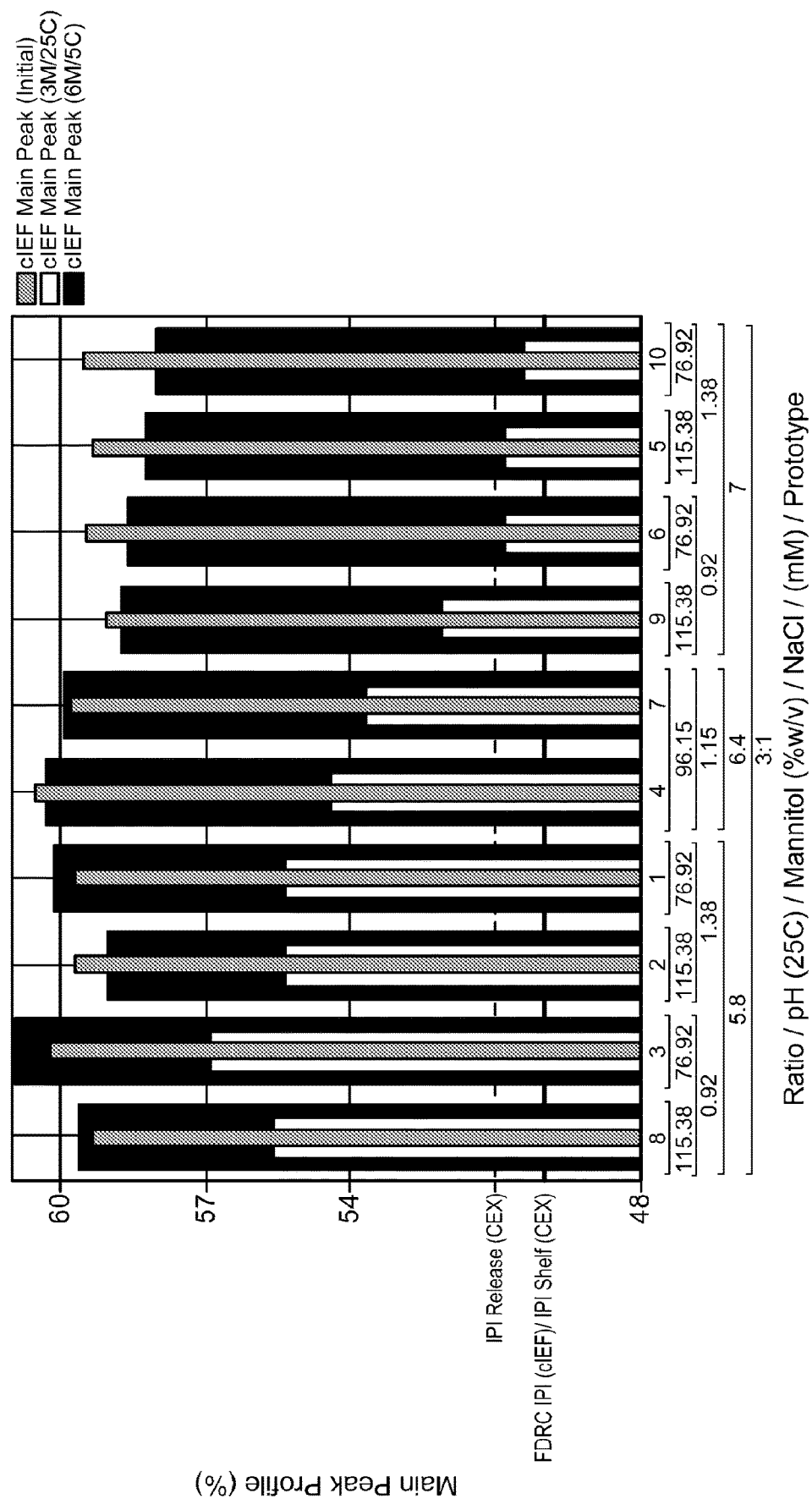

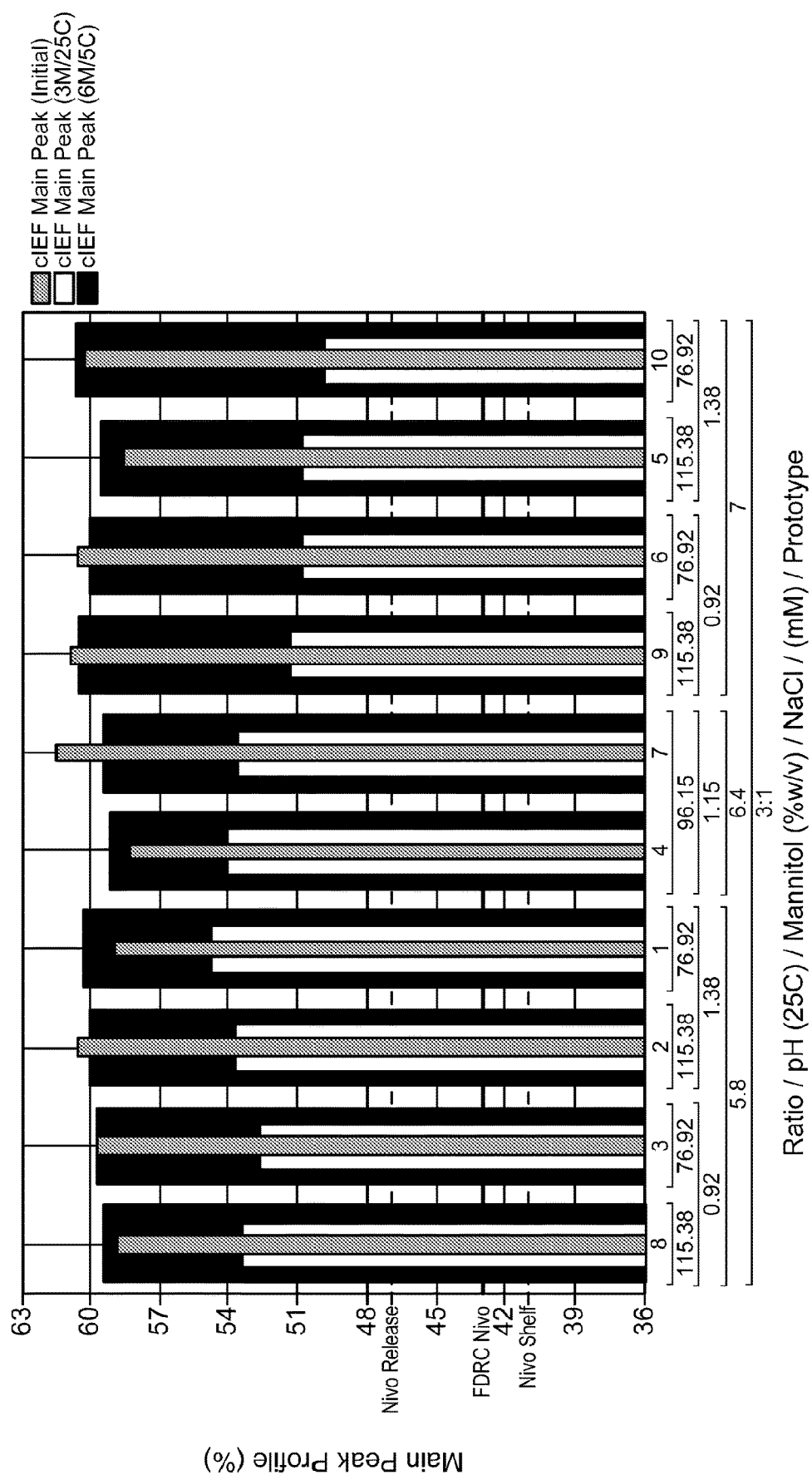

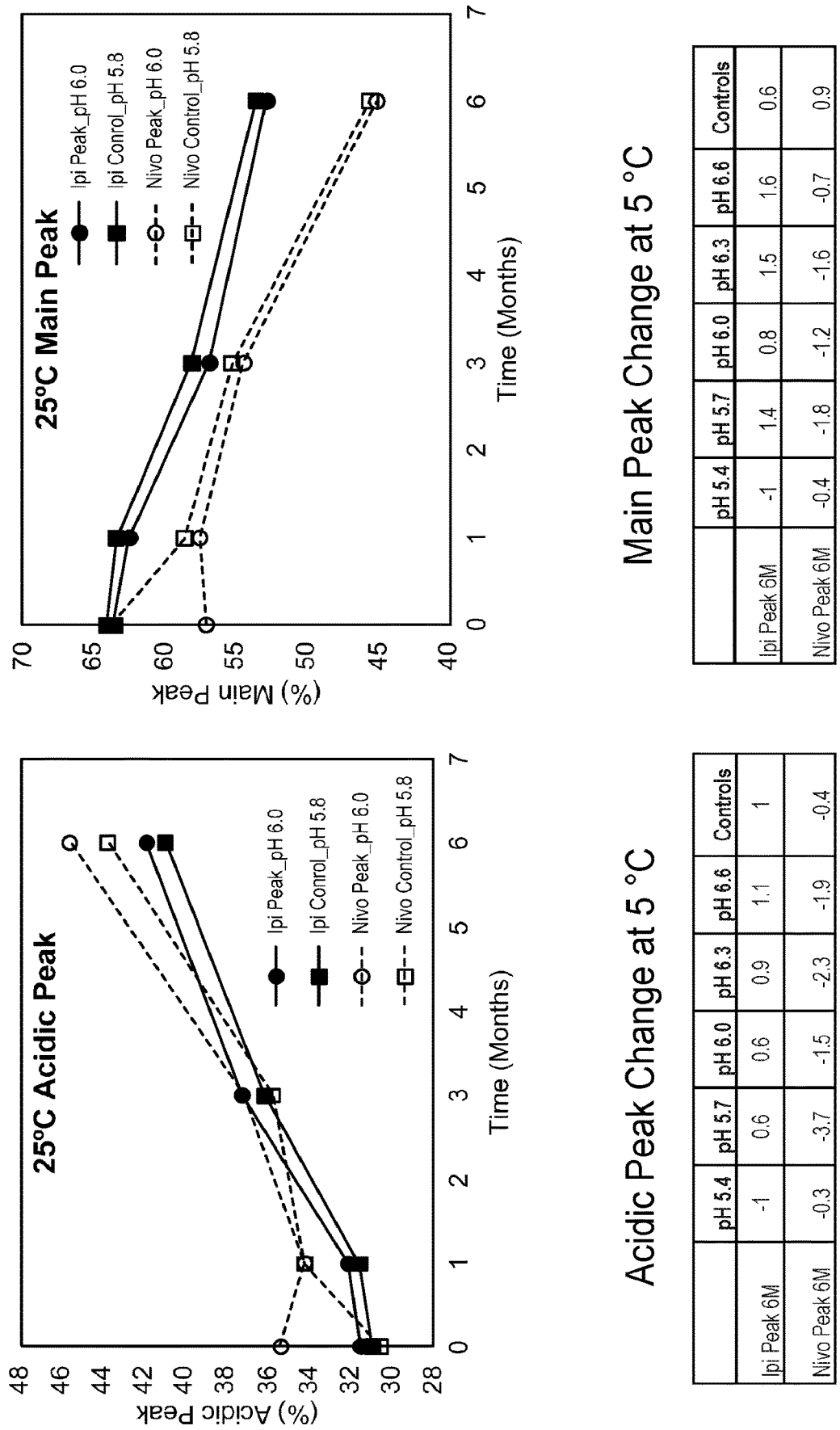
Figure 19. cIEF Peak Profile: Impact of pH

Figure 20. iCIEF Profile: pH range of 5.4 – 6.6

Ipilimumab Rate of Change/month Acidic and Main Peak

Note: 3 months data for 25°C and 5°C

| DP | Acidic Peak (%/Month) 25°C | Acidic Peak (%/Month) 5°C | Main Peak (%/Month) 25°C | Main Peak (%/Month) 5°C |
|---|---|---|---|---|
| FDRC (5.4) | 1.86 | 0.3 | -2.15 | -0.4 |
| FDRC (5.7) | 2.11 | 0.27 | -2.57 | -0.4 |
| FDRC (6.0) | 2.03 | 0.17 | -2.32 | -0.26 |
| FDRC (6.3) | 2.1 | 0.1 | -2.04 | -0.23 |
| FDRC (6.6) | 2.63 | 0.47 | -2.67 | -0.7 |

Nivolumab Rate of Change/month Acidic and Main Peak

Note: 3 months data for 25°C and 5°C

| DP | Acidic Peak (%/Month) 25°C | Acidic Peak (%/Month) 5°C | Main Peak (%/Month) 25°C | Main Peak (%/Month) 5°C |
|---|---|---|---|---|
| FDRC (5.4) | 1.15 | -0.33 | -2.15 | 0.33 |
| FDRC (5.7) | -0.08 | -0.6 | -0.96 | 0.36 |
| FDRC (6.0) | 0.72 | -0.03 | -0.96 | 0.5 |
| FDRC (6.3) | 0.8 | -0.4 | -1.16 | 0.36 |
| FDRC (6.6) | 1.7 | -0.07 | -1.71 | 0.1 |

SEQUENCE LISTING

<160> NUMBER OF SEQ ID NOS: 9

<210> SEQ ID NO 1
<211> LENGTH: 123
<212> TYPE: PRT
<213> ORGANISM: Artificial Sequence
<220> FEATURE:
<223> OTHER INFORMATION: VH chain

<400> SEQUENCE: 1

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Glu Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Met Val Arg Gly Asp Tyr Tyr Tyr Gly Met Asp
            100                 105                 110

Val Trp Gly Gln Gly Thr Thr Val Thr Val Ser
        115                 120

<210> SEQ ID NO 2
<211> LENGTH: 107
<212> TYPE: PRT
<213> ORGANISM: Artificial Sequence
<220> FEATURE:
<223> OTHER INFORMATION: VL chain

<400> SEQUENCE: 2

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Tyr
                85                  90                  95

Thr Phe Gly Gln Gly Thr Lys Leu Glu Ile Lys
            100                 105

<210> SEQ ID NO 3
<211> LENGTH: 123
<212> TYPE: PRT
<213> ORGANISM: Artificial Sequence
<220> FEATURE:
<223> OTHER INFORMATION: VH chain

<400> SEQUENCE: 3

Gln Val Gln Leu Val Glu Ser Gly Gly Gly Val Val Gln Pro Gly Arg
1               5                   10                  15

-continued

Ser Leu Arg Leu Ser Cys Ala Ala Ser Gly Phe Thr Phe Ser Ser Tyr
            20                  25                  30

Gly Phe His Trp Val Arg Gln Ala Pro Gly Lys Gly Leu Glu Trp Val
            35                  40                  45

Ala Val Ile Trp Tyr Ala Gly Ser Asn Lys Phe Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Gly Gln Leu Asp Tyr Tyr Tyr Tyr Val Met Asp Val
            100                 105                 110

Trp Gly Gln Gly Thr Thr Val Thr Val Ser Ser
            115                 120

<210> SEQ ID NO 4
<211> LENGTH: 107
<212> TYPE: PRT
<213> ORGANISM: Artificial Sequence
<220> FEATURE:
<223> OTHER INFORMATION: VL chain

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Tyr
                 85                  90                  95

Thr Phe Gly Gln Gly Thr Lys Leu Glu Ile Lys
            100                 105

<210> SEQ ID NO 5
<211> LENGTH: 122
<212> TYPE: PRT
<213> ORGANISM: Artificial Sequence
<220> FEATURE:
<223> OTHER INFORMATION: VH chain

<400> SEQUENCE: 5

Val Gln Leu Val Glu Ser Gly Gly Gly Val Val Gln Pro Gly Arg Ser
1               5                   10                  15

Leu Arg Leu Ser Cys Ala Ala Ser Gly Phe Thr Phe Ser Ser Tyr Gly
            20                  25                  30

Met His Trp Val Arg Gln Ala Pro Gly Lys Gly Leu Glu Trp Val Ala
            35                  40                  45

Val Ile Trp Tyr Ala Gly Ser Asn Lys Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala

```
                    85                  90                  95
Arg Gly Gly Arg Ile Ala Val Ala Phe Tyr Tyr Ser Met Asp Val Trp
                100                 105                 110

Gly Gln Gly Thr Thr Val Thr Val Ser Ser
            115                 120

<210> SEQ ID NO 6
<211> LENGTH: 107
<212> TYPE: PRT
<213> ORGANISM: Artificial Sequence
<220> FEATURE:
<223> OTHER INFORMATION: VL chain

<400> SEQUENCE: 6

Asp Ile Gln Met Thr Gln Ser Pro Ser Leu Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Glu Lys Ala Pro Lys Ser Leu Ile
            35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
            100                 105

<210> SEQ ID NO 7
<211> LENGTH: 449
<212> TYPE: PRT
<213> ORGANISM: Artificial Sequence
<220> FEATURE:
<223> OTHER INFORMATION: heavy chain

<400> SEQUENCE: 7

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Glu Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Met Val Arg Gly Asp Tyr Tyr Gly Met Asp
                100                 105                 110

Val Trp Gly Gln Gly Thr Thr Val Thr Val Ser Ser Ala Ser Thr Lys
            115                 120                 125

Gly Pro Ser Val Phe Pro Leu Ala Pro Cys Ser Arg Ser Thr Ser Glu
            130                 135                 140

Ser Thr Ala Ala Leu Gly Cys Leu Val Lys Asp Tyr Phe Pro Glu Pro
145                 150                 155                 160
```

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
    210                 215                 220

Lys Cys Cys Val Glu Cys Pro Cys Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Phe Arg
        290                 295                 300

Val Val Ser Val Leu Thr Val Val His Gln Asp Trp Leu Asn Gly Lys
305                 310                 315                 320

Glu Tyr Lys Cys Lys Val Ser Asn Lys Gly Leu Pro Ala Pro Ile Glu
                325                 330                 335

Lys Thr Ile Ser Lys Thr Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly

<210> SEQ ID NO 8
<211> LENGTH: 214
<212> TYPE: PRT
<213> ORGANISM: Artificial Sequence
<220> FEATURE:
<223> OTHER INFORMATION: light chain

<400> SEQUENCE: 8

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro

```
                65                  70                  75                  80
Glu Asp Phe Ala Thr Tyr Tyr Cys Gln Gln Phe Asn Ser Tyr Pro Tyr
                    85                  90                  95

Thr Phe Gly Gln Gly Thr Lys Leu Glu Ile Lys Arg Thr Val Ala Ala
                100                 105                 110

Pro Ser Val Phe Ile Phe Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
            210

<210> SEQ ID NO 9
<211> LENGTH: 453
<212> TYPE: PRT
<213> ORGANISM: Artificial Sequence
<220> FEATURE:
<223> OTHER INFORMATION: heavy chain

<400> SEQUENCE: 9

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Glu Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Met Val Arg Gly Asp Tyr Tyr Gly Met Asp
                100                 105                 110

Val Trp Gly Gln Gly Thr Thr Val Thr Val Ser Ser Ala Ser Thr Lys
            115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Arg Val Glu Pro
```

-continued

```
                210                 215                 220
Lys Ser Cys Asp Lys Thr His Thr Cys Pro Pro Cys Pro Ala Pro Glu
225                 230                 235                 240

Ala Glu Gly Ala Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
            290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ser Ser Ile Glu Lys Thr Ile Ser Lys Ala Lys Gly Gln Pro Arg Glu
                340                 345                 350

Pro Gln Val Tyr Thr Leu Pro Pro Ser Arg Glu Glu Met Thr Lys Asn
                355                 360                 365

Gln Val Ser Leu Thr Cys Leu Val Lys Gly Phe Tyr Pro Ser Asp Ile
            370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
            435                 440                 445

Ser Leu Ser Pro Gly
            450
```

COMBINATION THERAPY COMPRISING NIVOLUMAB AND IPILIMUMAB

CROSS-REFERENCE TO RELATED APPLICATIONS

The present application is a division of U.S. application Ser. No. 15/365,717, filed on Nov. 30, 2016, which is a continuation of U.S. application Ser. No. 15/130,513, filed on Apr. 15, 2016, which claims benefit to U.S. Provisional Application Nos. 62/303,855, filed Mar. 4, 2016; 62/269,000, filed Dec. 17, 2015; 62/265,268, filed Dec. 9, 2015; and 62/149,325, filed Apr. 17, 2015, each of which is incorporated by reference herein in its entirety.

REFERENCE TO A SEQUENCE LISTING SUBMITTED ELECTRONICALLY VIA EFS-WEB

The content of the electronically submitted sequence listing (Name: 3338_0260007_SL.txt; Size: 16,905 bytes; and Date of Creation: Dec. 20, 2019) is herein incorporated by reference in its entirety.

Throughout this application, various publications are referenced in parentheses by author name and date, or by Patent number or Patent Publication number. The disclosures of these publications are hereby incorporated in their entireties by reference into this application in order to more fully describe the state of the art as known to those skilled therein as of the date of the invention described and claimed herein. However, the citation of a reference herein should not be construed as an acknowledgement that such reference is prior art to the present invention.

FIELD OF THE INVENTION

This invention relates to pharmaceutical compositions that comprise a combination of an immune checkpoint antibody and a second antibody at a fixed dose formulation.

BACKGROUND OF THE INVENTION

Human cancers harbor numerous genetic and epigenetic alterations, generating neoantigens potentially recognizable by the immune system (Sjoblom et al. (2006) *Science* 314:268-74). The adaptive immune system, comprised of T and B lymphocytes, has powerful anti-cancer potential, with a broad capacity and exquisite specificity to respond to diverse tumor antigens. Further, the immune system demonstrates considerable plasticity and a memory component. The successful harnessing of all these attributes of the adaptive immune system would make immunotherapy unique among all cancer treatment modalities.

Recently, several immune checkpoint pathway inhibitors have begun to provide new immunotherapeutic approaches for treating cancer, including the development of an antibody (Ab), ipilimumab (YERVOY®), that binds to and inhibits Cytotoxic T-Lymphocyte Antigen-4 (CTLA-4) for the treatment of patients with advanced melanoma and the development of antibodies such as nivolumab and pembrolizumab (formerly lambrolizumab; USAN Council Statement (2013) Pembrolizumab: Statement on a nonproprietary name adopted by the USAN Council (ZZ-165), Nov. 27, 2013) that bind specifically to the Programmed Death-1 (PD-1) receptor and block the inhibitory PD-1/PD-1 ligand pathway.

Immune checkpoint antibodies can be administered in combination with other antibodies. Nonetheless, administering two antibodies can be burdensome due to different dosing and dosing interval between two antibodies, thereby causing multiple intravenous injections at different time points. Furthermore, two antibodies can have drastically different stability profiles. Due to the unique nature of each antibody, e.g., variations in Fc glycosylation, partial heavy chain C-terminal Lys processing, Fc methionine oxidation, hinge-region cleavage, and glycation of Lys residues, each antibody has varied physicochemical and/or thermodynamic properties, e.g., different degradation profiles when exposed to heat, freezing, light, pH extremes, agitation, sheer-stress, some metals, and organic solvents. Therefore, while a single formulation containing two antibodies would improve convenience, the unique nature of each antibody makes such a single formulation difficult to identify.

SUMMARY OF THE INVENTION

The present invention relates to a pharmaceutical composition comprising an X amount of a first antibody or an antigen-binding fragment thereof, which comprises an anti-PD-1 antibody or an antigen-binding fragment thereof, and a Y amount of a second antibody or an antigen-binding fragment thereof, wherein the ratio of the X amount to the Y amount is about 50:1 to about 1:50. In some embodiments, the ratio of X to Y is about 50:1, about 40:1, about 30:1, about 20:1, about 10:1, about 5:1, about 3:1, about 1:1, about 1:3, about 1:5, about 1:10, about 1:20, about 1:30, about 1:40, or about 1:50.

In some embodiments, the anti-PD-1 antibody is nivolumab or pembrolizumab. In a particular embodiment, the anti-PD-1 antibody is nivolumab.

In certain embodiments, the X amount of the first antibody or antigen binding fragment thereof is at least about 60 mg, about 80 mg, about 100 mg, about 120 mg, about 140 mg, about 160 mg, about 180 mg, about 200 mg, about 220 mg, about 240 mg, about 260 mg, about 280 mg, or about 300 mg. In some embodiments, the X amount of the first antibody is at least about 80 mg, about 160 mg, or about 240 mg. In other embodiments, the X amount of the first antibody or antigen-binding fragment thereof is about 60 mg, about 80 mg, about 100 mg, about 120 mg, about 140 mg, about 160 mg, about 180 mg, about 200 mg, about 220 mg, about 240 mg, about 260 mg, about 280 mg, or about 300 mg. In certain embodiments, the X amount of the first antibody or antigen-binding fragment thereof is about 80 mg or about 240 mg. In other embodiments, the X amount of the first antibody or antigen binding fragment thereof is more than at least about 300 mg. In some embodiments, the X amount of the first antibody or antigen binding fragment thereof is from at least about 300 mg to at least about 500 mg, from at least about 300 mg to at least about 450 mg, from at least about 300 mg to at least about 400 mg, from at least about 300 mg to at least about 350 mg, from at least about 350 mg to at least about 500 mg, from at least about 400 mg to at least about 500 mg, or from at least about 450 mg to at least about 500 mg. In certain embodiments, the X amount is at least about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg. In one particular embodiment, the X amount of the first antibody or antigen binding fragment thereof is about 360 mg. In another embodiment, the X amount of the first antibody or antigen binding fragment thereof is about 480 mg.

In one aspect, the second antibody or antigen-binding fragment thereof can be an anti-CTLA4 antibody. The ratio of the X amount of the first antibody (e.g., an anti-PD-1 antibody or anti-PD-L1 antibody) to the Y amount of the second antibody (e.g., an anti-CTLA-4 antibody) is about 3:1, about 1:1, or about 1:3. In some embodiments, (i) the X amount of an anti-PD-1 antibody is about 240 mg and the Y amount of an anti-CTLA-4 antibody is about 80 mg, (ii) the X amount is about 80 mg and the Y amount is about 80 mg; (iii) the X amount is about 160 mg and the Y amount is about 160 mg; (iv) the X amount is about 240 mg and the Y amount is about 240 mg; or (v) the X amount is about 80 mg and the Y amount is about 240 mg. In certain embodiments, the anti-CTLA4 antibody is tremelimumab or ipilimumab.

In another aspect, the second antibody can be an anti-LAG3 antibody. The ratio of the X amount of the first antibody (e.g., an anti-PD-1 antibody or anti-PD-L1 antibody) to the Y amount of the second antibody (e.g., anti-LAG-3 antibody) is about 12:1, about 3:1, or about 1:1. In a particular embodiment, the anti-LAG3 antibody is BMS-986016.

In other aspects, the second-antibody is an anti-CD137 antibody. In some embodiments, the ratio of the X amount of the first antibody (e.g., an anti-PD-1 antibody or anti-PD-L1 antibody) to the Y amount of the second antibody (e.g., anti-CD-137 antibody) is about 1:1, about 1:2, about 1:3, about 1:4, about 1:5, about 1:10, about 1:20, about 1:30, about 1:40, about 1:50, about 50:1, about 40:1, about 30:1, about 20:1, about 10:1, about 5:1, about 4:1 or about 2:1. In a particular embodiment, the anti-CD137 antibody is urelumab.

In some aspects, the second antibody is an anti-KIR antibody. In some embodiments, the ratio of the X amount of the first antibody (e.g., an anti-PD-1 antibody or anti-PD-L1 antibody) to the Y amount of the second antibody (e.g., anti-KIR antibody) is about 30:1, about 10:1, about 3:1, about 1:1, or about 1:2. In some embodiments, the anti-KIR antibody is 1-7F9 or lirilumab.

In certain aspects, the second antibody can be an anti-GITR antibody. In some embodiments, the anti-GITR antibody is MK4166 or TRX518. In other embodiments, the ratio of the X amount of the first antibody (e.g., an anti-PD-1 antibody or anti-PD-L1 antibody) to the Y amount of the second antibody (e.g., anti-GITR antibody) is about 1:1, about 1:2, about 1:3, about 1:4, about 1:5, about 1:6, about 1:7, about 1:8, about 1:9, about 1:10, about 2:1, about 3:1, about 4:1, about 5:1, about 6:1, about 7:1, about 8:1, about 9:1, or about 10:1.

In other aspects, the second antibody is selected from the group consisting of: an anti-TGFβ antibody, an anti-IL-10 antibody, an anti-B7-H4 antibody, an anti-Fas ligand antibody, an anti-CXCR4 antibody, an anti-mesothelin antibody, an anti-CD27 antibody, an anti-CD73 antibody, and any combination thereof.

A pharmaceutical composition of the invention can further comprises one or more additional components selected from the group consisting of: a bulking agent, a stabilizing agent, a chelating agent, a surfactant, a buffering agent, an ionic agent and any combination thereof.

In one embodiment, the pharmaceutical composition of the present invention is formulated in one or more of various buffering agents. For example, a composition of the invention can be formulated in a Tris-Cl, histidine, citrate or Tris-citrate buffer. In one embodiment, the composition is formulated in a Tris-Cl buffer, the concentration of Tris-Cl being at least about 5 mM, about 10 mM, about 15 mM, about 20 mM, about 25 mM, about 30 mM, about 35 mM, about 40 mM, or about 50 mM. In another embodiment, the concentration of Tris-Cl is about 20 mM. In other embodiments, the composition is formulated in a citrate buffer, the concentration of citrate being at least about 5 mM, about 10 mM, about 15 mM, about 20 mM, about 25 mM, about 30 mM, about 35 mM, about 40 mM, or about 50 mM. In a particular embodiment, the citrate concentration is about 10 mM or about 20 mM. In some embodiments, the composition is formulated in a histidine buffer, the concentration of histidine being at least about 5 mM, about 10 mM, about 15 mM, about 20 mM, about 25 mM, about 30 mM, about 35 mM, about 40 mM, or about 50 mM. In some embodiments, the histidine concentration is about 20 mM. In other embodiments, the composition is formulated in a Tris-citrate buffer, the concentration of Tris-Cl being at least about 5 mM, about 10 mM, about 15 mM, about 20 mM, about 25 mM, about 30 mM, about 35 mM, about 40 mM, or about 50 mM, and the concentration of citrate being at least about 2 mM, about 5 mM, about 10 mM, about 15 mM, about 20 mM, about 25 mM, about 30 mM, about 35 mM, about 40 mM, or about 50 mM. In certain embodiments, the concentration of Tris-Cl is about 13.3 mM and the concentration of citrate is about 6.7 mM.

The composition of the invention can have a pH ranging from about 5 to about 8. For example, the pH of the composition can be at least about 5, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, or about 8.0. In some embodiments, the pH of the composition is at least about 6.0, about 6.2, about 6.5, about 6.6 or about 7.0

The composition can further comprise a bulking agent. In certain embodiments, the bulking agent is selected from the group consisting of NaCl, mannitol, glycine, alanine, and any combination thereof.

In certain embodiments, the composition comprises a stabilizing agent. The stabilizing agent is selected from the group consisting of sucrose, trehalose, raffinose, arginine; or any combination thereof.

In other embodiments, the composition comprises a chelating agent. The chelating agent is selected from the group consisting of diethylenetriaminepentaacetic acid (DTPA), ethylenediaminetetraacetic acid, nitrilotriacetic acid, and any combination thereof.

In certain embodiments, the surfactant is selected from the group consisting of polysorbate 80 (PS80), polysorbate 20 (PS20), and any combination thereof.

In some embodiments, the composition comprises NaCl at a concentration of at least about 5 mM, at least about 10 mM, at least about 15 mM, at least about 20 mM, at least about 25 mM, at least about 30 mM, at least about 35 mM, at least about 40 mM, at least about 45 mM, at least about 50 mM, at least about 60 mM, at least about 70 mM, at least about 75 mM, at least about 80 mM, at least about 90 mM, at least about 100 mM, at least about 110 mM, at least about 120 mM, at least about 130 mM, at least about 140 mM, at least about 150 mM, at least about 175 mM, at least about 200 mM, at least about 225 mM, at least about 250 mM, at least about 275 mM, at least about 300 mM, at least about 350 mM, at least about 400 mM, at least about 450 mM or at least about 450 mM. In some embodiments, the concentration of NaCl is about 100 mM, about 96.15 mM, about 83.3 mM, about 78.57 mM or about 50 mM.

In some embodiments, the composition comprises mannitol (% w/v) USP at a concentration of at least about 0.25%, at least about 0.5%, at least about 0.75%, at least about 1%, at least about 1.5%, at least about 2%, at least about 2.5%, at least about 3%, at least about 3.5%, at least about 4%, at least about 4.5%, at least about 5%, at least about 7.5% or at least about 10%. In some embodiments, the concentration of mannitol is about 1%, about 1.15%, about 1.67%, about 1.86%, or about 3%.

In some embodiments, the composition comprises DTPA, USP at a concentration of at least about 5 µM, at least about 10 µM, at least about 15 µM, at least about 20 µM, at least about 25 µM, at least about 30 µM, at least about 40 µM, at least about 50 µM, at least about 60 µM, at least about 70 µM, at least about 75 µM, at least about 80 µM, at least about 90 µM, at least about 100 µM, at least about 110 µM, at least about 120 µM, at least about 130 µM, at least about 140 µM, at least about 150 µM, at least about 175 µM, or at least about 200 µM. In some embodiments, the concentration of DTPA is about 20 µM, about 50 µM, about 65.71 µM, about 73.3 µM, about 93.85 µM, or about 100 µM.

In some embodiments, the composition comprises PS80 (% w/v) at a concentration of at least about 0.005%, at least about 0.01%, at least about 0.015%, at least about 0.02%, at least about 0.03%, at least about 0.04%, at least about 0.05%, at least about 0.06%, at least about 0.07%, at least about 0.08%, at least about 0.09%, or at least about 0.1%. In some embodiments, the concentration of PS80 is about 0.01%, about 0.012%, about 0.013%, about 0.02%, about 0.23%, about 0.04%, or about 0.05%.

In some embodiments, the composition comprises sucrose (% w/v) at a concentration of at least about 1%, at least about 2%, at least about 3%, at least about 4%, at least about 4.5%, at least about 5%, at least about 5.5%, at least about 6%, at least about 6.5%, at least about 7%, at least about 7.5%, at least about 8%, at least about 8.5%, at least about 9%, at least about 9.5%, at least about 10%, at least about 12% or at least about 15%. In some embodiments, the concentration of sucrose is about 6% or about 8.5%.

In certain embodiments, the invention includes the following compositions: (i) a pharmaceutical composition comprising a 1:1 ratio of nivolumab to ipilimumab in a buffer comprising about 13.3 mM Tris, about 6.7 mM citrate, about 1.67% mannitol, about 83.3 mM NaCl, about 73.3 µM DTPA and about 0.013% PS80 at a pH of about 6.2; (ii) a pharmaceutical composition comprising a 3:1 ratio of nivolumab to ipilimumab in a Tris-citrate buffer comprising about 1.15% mannitol, about 96.15 mM NaCl, about 93.85 µM DTPA and about 0.012% PS80 at a pH of about 6.6; (iii) a pharmaceutical composition comprising a 1:3 ratio of nivolumab to ipilimumab in a Tris-citrate buffer comprising about 1.86% mannitol, about 78.57 mM NaCl, about 65.71 µM DTPA and about 0.023% PS80 at a pH of about 6.0; (iv) a pharmaceutical composition comprising a 3:1 ratio of nivolumab to ipilimumab in a 20 mM histidine buffer comprising about 50 mM NaCl, about 50 µM DTPA, about 6% sucrose, and about 0.05% PS80 at about pH 6; (v) a pharmaceutical composition comprising a 3:1 ratio of nivolumab to ipilimumab in a about 20 mM histidine buffer comprising about 50 mM NaCl, about 50 µM DTPA, about 6% sucrose, and about 0.05% PS80 at about pH 7; (vi) a pharmaceutical composition comprising a 3:1 ratio of nivolumab to ipilimumab in an about 20 mM histidine buffer comprising about 50 µM DTPA, about 8.5% sucrose, and about 0.05% PS80 at about pH 6; (vii) a pharmaceutical composition comprises comprises a 3:1 ratio of nivolumab to ipilimumab in an about 20 mM citrate buffer comprising about 50 mM NaCl, about 50 µM DTPA, about 6% sucrose, and about 0.05% PS80 at about pH 6; (viii) a pharmaceutical composition comprising a 3:1 ratio of nivolumab to ipilimumab in an about 20 mM citrate buffer comprising about 50 mM NaCl, about 20 µM DTPA, about 3% mannitol, and about 0.04% PS80 at about pH 6; (ix) a pharmaceutical composition comprising a 1:1 ratio of nivolumab to ipilimumab in an about 20 mM citrate buffer comprising about 50 mM NaCl, about 100 µM DTPA, about 3% mannitol, and about 0.02% PS80 at about pH 6; (x) a pharmaceutical composition comprising a 1:1 ratio of nivolumab to ipilimumab in an about 20 mM citrate buffer comprising about 50 mM NaCl, about 100 µM DTPA, about 3% mannitol, and about 0.02% PS80 at about pH 6.5; (xi) a pharmaceutical composition comprising a 1:1 ratio of nivolumab to ipilimumab in an about 20 mM citrate buffer comprising about 100 mM NaCl, about 100 µM DTPA, about 1.0% mannitol, and about 0.02% PS80 at about pH 6.5; or (xii) a pharmaceutical composition comprising a 1:1 ratio of nivolumab to ipilimumab in an about 20 mM citrate buffer comprising about 50 mM NaCl, about 100 µM DTPA, about 6% sucrose, and about 0.02% PS80 at about pH 6.0.

In other embodiments, the invention includes a pharmaceutical composition comprising a 1:3 ratio of nivolumab to ipilimumab comprising about 4.62 mg/ml nivolumab, about 1.54 mg/ml ipilimumab, about 18.5 mM Tris Hydrochloride, about 1.5 mM Sodium Citrate Dihydrate, about 96.2 mM NaCl, about 1.2% Mannitol, about 93.9 µM Pentetic Acid, and about 0.012% PS80 at pH 6.0 or a pharmaceutical composition comprising a 1:3 ratio of nivolumab to ipilimumab comprising about 4.61 mg/ml nivolumab, about 1.54 mg/ml ipilimumab, about 18.46 mM Tris Hydrochloride, about 1.54 mM Sodium Citrate Dihydrate, about 96.15 mM NaCl, about 1.15% Mannitol, about 93.85 µM Pentetic Acid, and about 0.012% PS80 at pH 6.3.

The composition of the invention after formulation can be stable and stored at about 5° C. for at least about 1 week, at least about 2 weeks, at least about 1 month, at least about 2 months, at least about 3 months, at least about 6 months, at least about 9 months, at least about 1 year, at least about 2 years or at least about 5 years. In some embodiments, the composition is stable and can be stored at about 40° C. for at least about 1 week, at least about 2 weeks, at least about 1 month, at least about 2 months, at least about 3 months, at least about 6 months, at least about 9 months, at least about 1 year, at least about 2 years or at least about 5 years. In other embodiments, the composition is stable and can be stored at about 25° C. for at least about 1 week, at least about 2 weeks, at least about 1 month, at least about 2 months, at least about 3 months, at least about 6 months, at least about 9 months, at least about 1 year, at least about 2 years or at least about 5 years.

The pharmaceutical composition of the invention can exhibit a minimal change of an acidic peak upon stress, e.g., after being stored at a particular temperature for a long period of time. In one embodiment, the composition exhibits a change of an acidic peak less than about 10%, about 9%, about 8%, about 7%, about 6%, about 5%, about 4%, about 3%, about 2%, or about 1% after being stored for about 6 months or about 3 months at about 5° C. In certain embodiments, the composition exhibits a change of an acidic peak that is less than about 15%, about 14%, about 13%, about 12%, about 11%, about 10%, about 9%, about 8%, about 7%, about 6%, about 5%, about 4%, about 3%, about 2% or about 1% after being stored for about 3 months at about 25° C. In other embodiments, the composition exhibits a change of an acidic peak that is less than about 15%, about 14%, about 13%, about 12%, about 11%, about 10%, about 9%, about 8%, about 7%, about 6%, about 5%, about 4%, about 3%, about 2% or about 1% after being stored for about 3 months at about 40° C.

The composition of the invention can also exhibit a minimal change of high molecular weight peak after being stored for a long period of time, several weeks, months, or years. In one embodiment, the composition exhibits a change of a high molecular weight peak less than about 5%, about 4%, about 3%, about 2%, about 1.5%, about 1.4%, about 1.3%, about 1.2%, about 1.1%, about 1%, about 0.9%, about 0.8%, about 0.7%, about 0.6%, about 0.5%, about 0.4%, about 0.3%, about 0.2%, or about 0.1% after being stored for about 3 months at about 4° C. In another embodiment, the composition exhibits a change of a high molecular weight peak that is less than about 5%, about 4%, about 3%, about 2%, about 1.5%, about 1.4%, about 1.3%, about 1.2%, about 1.1%, about 1%, about 0.9%, about 0.8%, about 0.7%, about 0.6%, about 0.5%, about 0.4%, about 0.3%, about 0.2%, or about 0.1% after being stored for about 2 months or about 3 months at about 25° C. In other embodiments, the composition exhibits a change of a high molecular weight peak that is less than about 5%, about 4%, about 3%, about 2%, about 1.5%, about 1.4%, about 1.3%, about 1.2%, about 1.1%, about 1%, about 0.9%, about 0.8%, about 0.7%, about 0.6%, about 0.5%, about 0.4%, about 0.3%, about 0.2%, or about 0.1% after being stored for about 2 months or about 3 months at about 40° C.

Furthermore, in certain embodiments, the composition can exhibit a minimal change of a main peak determined by Capillary Isoelectric Focusing (cIEF) analysis. In one embodiment, the composition shows a change of a main peak less than about 5%, about 4%, about 3%, about 2%, about 1.5%, about 1.4%, about 1.3%, about 1.2%, about 1.1%, about 1%, about 0.9%, about 0.8%, about 0.7%, about 0.6%, about 0.5%, about 0.4%, about 0.3%, about 0.2%, or about 0.1% after being stored for about 1 month at about 4° C. In some embodiments, the composition exhibits a change of a main peak of Capillary Isoelectric Focusing (cIEF) analysis that is less than about 5%, about 4%, about 3%, about 2%, about 1.5%, about 1.4%, about 1.3%, about 1.2%, about 1.1%, about 1%, about 0.9%, about 0.8%, about 0.7%, about 0.6%, about 0.5%, about 0.4%, about 0.3%, about 0.2%, or about 0.1% after being stored for about 1 month at about 25° C. In some embodiments, the composition exhibits a change of a main peak of Capillary Isoelectric Focusing (cIEF) analysis that is less than about 5%, about 4%, about 3%, about 2%, about 1.5%, about 1.4%, about 1.3%, about 1.2%, about 1.1%, about 1%, about 0.9%, about 0.8%, about 0.7%, about 0.6%, about 0.5%, about 0.4%, about 0.3%, about 0.2%, or about 0.1% after being stored for about 1 month at about 40° C.

In some embodiments, the composition exhibits a minimal change of a low molecular weight peak. In one embodiment, the composition exhibits a change of a low molecular weight peak less than about 5%, about 4%, about 3%, about 2%, about 1.5%, about 1.4%, about 1.3%, about 1.2%, about 1.1%, about 1%, about 0.9%, about 0.8%, about 0.7%, about 0.6%, about 0.5%, about 0.4%, about 0.3%, about 0.2%, or about 0.1% after being stored for about 2 months at about 40° C. In certain embodiments, the composition exhibits a change of a low molecular weight peak that is less than about 5%, about 4%, about 3%, about 2%, about 1.5%, about 1.4%, about 1.3%, about 1.2%, about 1.1%, about 1%, about 0.9%, about 0.8%, about 0.7%, about 0.6%, about 0.5%, about 0.4%, about 0.3%, about 0.2%, or about 0.1% after being stored for about 2 months at about 25° C. In certain embodiments, the composition exhibits a change of a low molecular weight peak that is less than about 5%, about 4%, about 3%, about 2%, about 1.5%, about 1.4%, about 1.3%, about 1.2%, about 1.1%, about 1%, about 0.9%, about 0.8%, about 0.7%, about 0.6%, about 0.5%, about 0.4%, about 0.3%, about 0.2%, or about 0.1% after being stored for about 2 months at about 4° C.

In some embodiments, the composition is diluted prior to use. In some embodiments, the composition is diluted with 0.9% Sodium Chloride Injection, USP or 5% Dextrose Injection, USP prior to use. In some embodiments, the composition is diluted to obtain a desired concentration of first and second antibody.

In some embodiments, the disclosure is directed to a kit comprising a composition disclosed herein.

In some embodiments, the disclosure is directed to method of making a composition disclosed herein. In some embodiments, a formulation comprising the anti-PD-1 antibody drug product is mixed with a formulation comprising the second antibody drug product to obtain the desired ratio in a final drug product with no buffer changes. In some embodiments, a formulation comprising the anti-PD-1 antibody drug substance and a formulation comprising the second antibody drug substance is subject to buffer exchanges and/or concentration before being mixed to obtain the desired ratio in a final drug product.

In some embodiments, the disclosure is directed to a method of modulating an immune response to a patient in need thereof comprising administering a composition disclosed herein to the patient.

In some embodiments, the disclosure is directed to a method of administering two antibodies at the same time to a patient in need thereof comprising administering to the patient a composition disclosed herein, wherein the antibodies are capable of treating at least one disease or condition.

In some embodiments, the disclosure is directed to method of treating a disease or condition comprising administering a composition disclosed herein to a patient.

In some embodiments, the disease or condition is an infectious disease. In some embodiments, the disease is cancer. In some embodiments, the cancer is melanoma cancer, renal cancer, prostate cancer, breast cancer, colon cancer, lung cancer, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and any combinations thereof.

In some embodiments, the composition is administered intravenously. In some embodiments, the composition is diluted prior to administration. In some embodiments, the composition is administered at a flat dose. In some embodiments, the amount of the first antibody and the amount of the second antibody administered to the patient at a single dose are identical the X amount and the Y amount, respectively. In some embodiments, the composition is administered at a weight-based dose. In some embodiments, the amount of the first antibody administered to the patient is at least about 0.5 mg/kg, about 1 mg/kg, about 1.5 mg/kg, about 2 mg/kg, about 3 mg/kg or about 5 mg/kg. In some embodiments, the amount of the first antibody administered to the patient at least about 1 mg/kg.

In some embodiments, the composition is administered at least about weekly, at least about twice weekly, at least about every two weeks, at least about every three weeks, or at least about monthly. In some embodiments, the administering lasts for at least about 8 weeks, at least about 12 weeks, at least about 3 months, at least about 6 months, at least about 9 months, at least about 1 year, at least about 18 months, at least about 2 years or greater than 2 years. In some embodiments, the patient is also treated with another anti-cancer agent.

BRIEF DESCRIPTION OF THE FIGURES

FIG. 1 shows the compositions of an anti-CTLA4 antibody (i.e., ipilimumab) and an anti-PD-1 antibody (i.e., nivolumab) drug substance (DS) and drug product (DP) formulations.

FIG. 2A shows the results of size exclusion chromatography (SEC) of the combined 1:1 ratio fixed dosing combination (FDRC=fixed dose ratio combination) formulation of an anti-PD-1 antibody (e.g., nivolumab) and an anti-CTLA-4 antibody (e.g., ipilimumab). FIG. 2B shows imaged capillary isoelectric focusing (cIEF) analyses of the combined 1:1 ratio fixed dosing combination (FDRC=fixed dose ratio combination) formulation of an anti-PD-1 antibody (e.g., nivolumab) and an anti-CTLA-4 antibody (e.g., ipilimumab). EC indicates a mix of Tris and citrate buffers. The nivolumab DP and ipilimumab DP results are shown as controls; and the combination of an anti-PD-1 antibody and an anti-CTLA4 antibody (e.g., nivolumab and ipilimumab) are shown as EC FDRC in FIGS. 2A-B. FIG. 2A shows the actual change in the high molecular weight (HMW) peak size (%) in formulations stored for 3 months at 40° C. as compared to day-0 controls. The adjusted pH at 25° C. and the concentrations of polysorbate 80 (PS80), NaCl, and Mannitol for each prototype formulation are shown below the x-axis in FIG. 2A. FIG. 2B shows the actual change in the acidic peak size (%) of nivolumab and ipilimumab in formulations stored for 6 months at 5° C. as compared to day-0 controls. The adjusted pH at 25° C. and the concentrations of NaCl and Mannitol for each formulation are shown below the x-axis in FIG. 2B. Data points are labeled as N (nivolumab), C (combination of nivolumab and ipilimumab), and I (ipilimumab) in FIGS. 2A-B.

FIGS. 3A-B show the results of SEC analyses of the 1:3, 1:1, or 3:1 ratio fixed dosing formulations for an anti-PD-1 antibody (e.g., nivolumab) and an anti-CTLA-4 antibody (e.g., ipilimumab). The nivolumab DP and ipilimumab DP results are shown as controls; and the combination of an anti-PD-1 antibody and an anti-CTLA4 antibody (e.g., nivolumab and ipilimumab) are shown as EC (FIGS. 3A-B). FIG. 3A shows the HMW peak size (%) at day 0 (Initial), the HMW peak size after 2 months at 40° C., and the change in HMW peak size between the day-0 control and the formulation at 2 months at 40° C. for each sample and prototype (EC:pH 6.0 (1 ipilimumab:3 nivolumab); EC:pH 6.2 (1 ipilimumab:1 nivolumab); and EC:pH 6.6 (3 ipilimumab:1 nivolumab)) formulation. FIG. 3B shows the LMW peak size (%) at day 0 (Initial), the LMW peak size after 2 months at 40° C., the change in LMW peak size between the day-0 control and each formulation following storage for 2 months at 40° C., and the change in LMW peak size between the day-0 control and each formulation following storage for 3 months at 25° C. The concentrations of the adjusted pH at 25° C., ipilimumab concentration, nivolumab concentration, PS80, and NaCl for each formulation are shown below the x-axes (FIGS. 3A-B).

FIGS. 4A-C show the results of cIEF analysis of the 1:3, 1:1, or 3:1 ratio fixed dosing formulations for an anti-PD-1 antibody (e.g., nivolumab) and an anti-CTLA-4 antibody (e.g., ipilimumab) following storage for 3 months at 25° C. (FIG. 4A), 3 months at 5° C. (FIG. 4B), and 1 month at 25° C. (FIG. 4C). The nivolumab DP and ipilimumab DP results are shown as controls (FIGS. 4A-C). The actual differences in the nivolumab (N) and ipilimumab (I) acidic peak sizes (%) at the selected time points relative to the day-0 controls are shown for the controls and each prototype (EC:pH 6.0 (1 ipilimumab:3 nivolumab); EC:pH 6.2 (1 ipilimumab:1 nivolumab); and EC:pH 6.6 (3 ipilimumab:3 nivolumab)) formulation (FIGS. 4A-C). The theoretical pH at 25° C., the buffer type, and the ratio of ipilimumab to nivolumab for each formulation are shown below the x-axis in FIGS. 4A-B; and the NaCl concentration, the theoretical pH at 25° C., and the ratio of ipilimumab to nivolumab for each formulation are shown below the x-axis in FIG. 4C. The theoretical pH is equivalent to the stability study pH (FIGS. 4A-C).

FIGS. 5A-B show the results of SEC (FIG. 5A) and cIEF (FIG. 5B) analyses of the novel design-of-experiment (DoE) 3:1 Ratio Fixed Dosing formulations for an anti-PD-1 antibody (e.g., nivolumab) and an anti-CTLA-4 antibody (e.g., ipilimumab). The nivolumab DP and ipilimumab DP results are shown as controls (FIGS. 5A-B). FIG. 5A shows the HMW peak size (%) at day 0 (Initial), the HMW peak size after 3 months at 40° C., the change in HMW peak size between the day-0 control and the formulation following storage for 3 months at 40° C., and the change in HMW peak size between the day-0 control and the formulation following storage for 3 months at 25° C. for the control formulations and each prototype formulation (Combo New, Combo 4, Combo 5, Combo 6, and Combo 8). FIG. 5B shows the actual differences in the nivolumab (N) and ipilimumab (I) acidic peak sizes (%) relative to the day-0 controls for each formulation prototype following storage for 3 months at 25° C. The ratio of ipilimumab to nivolumab; the concentrations of NaCl, mannitol, and sucrose; the theoretical pH at 25° C., and the buffer type for each formulation are shown below the x-axes (FIGS. 5A-B).

FIGS. 6A-B show the results of SEC analyses of the platform combined (PC) 1:1; 1:3; or 3:1 ratio fixed dosing formulations for an anti-PD-1 antibody (e.g., nivolumab) and an anti-CTLA-4 antibody (e.g., ipilimumab) following storage for 3 months at 40° C. (FIG. 6A) and 3 months at 5° C. (FIG. 6B). The nivolumab DP and ipilimumab DP results are shown as controls (FIGS. 6A-B). FIG. 6A shows the actual change in the BMW peak size (%) between the day-0 controls and each control and prototype (PC:pH 6.0-1:1; PC:pH 5.5-1:3; PC:pH 6.0-1:3; PC:pH 6.5-1:3; and PC:pH 6.0-3:1) formulation following storage for 3 months at 40° C. FIG. 6B shows the HMW peak size (%) at day 0 (Initial) and the HMW peak size after 3 months at 5° C. for each formulation. The buffer type and the ratio of ipilimumab to nivolumab for each formulation are shown below the x-axes (FIGS. 6A-B).

FIGS. 7A-B show the results of cIEF analyses of the platform combined (PC) 1:1; 1:3; or 3:1 ratio fixed dosing formulations for an anti-PD-1 antibody (e.g., nivolumab) and an anti-CTLA-4 antibody (e.g., ipilimumab) following storage for 3 months at 25° C. (FIG. 7A) and 3 months at 5° C. (FIG. 7B). The nivolumab DP and ipilimumab DP results are shown as controls (FIGS. 7A-B). FIG. 7A shows the actual differences in the nivolumab (N) and ipilimumab (I) acidic peak sizes (%) relative to the day-0 controls for each control and prototype (PC:pH 6.0-1:1; PC:pH 5.5-1:3; PC:pH 6.0-1:3; PC:pH 6.5-1:3; and PC:pH 6.0-3:1) formulation following storage for 3 months at 25° C. FIG. 7B shows the actual differences in the nivolumab (N) and ipilimumab (I) acidic peak sizes (%) relative to the day-0 controls for each formulation following storage for 3 months at 5° C. The buffer type and the ratio of ipilimumab to nivolumab for each formulation are shown below the x-axes (FIGS. 7A-B).

FIG. 8 shows the results of SEC analyses of the nivolumab-DP-based FDRC (1:1) formulations following storage for 1 month at 40° C. The nivolumab DP and ipilimumab DP results are shown as controls (FIG. 8). The actual change in the BMW peak size (%) between the day-0 controls and the formulations following storage for 1 month at 40° C. is shown for each control and prototype (A, B, C, and D) formulation (FIG. 8). The ratio of ipilimumab to nivolumab, the buffer type, and the theoretical adjusted pH for each formulation are shown below the x-axis (FIG. 8).

FIG. 9 shows the results of cIEF analyses of the nivolumab-DP-based FDRC (1:1) formulations following storage for 3 months at 25° C. The nivolumab DP and ipilimumab DP results are shown as controls. FIG. 9 shows the actual differences in the nivolumab (N) and ipilimumab (I) acidic peak sizes (%) relative to the day-0 controls for each control and prototype (A, B, C, and D) formulation following storage for 3 months at 25° C. The ratio of ipilimumab to nivolumab, the buffer type, and the theoretical adjusted pH for each formulation are shown below the x-axis.

FIG. 10 shows the ipilimumab acidic peak degradation rate in the FDRC and commercial composition at 25° C./60% RH (relative humidity). The FDRC composition is shown at Table 7.

FIG. 11 shows the nivolumab acidic peak degradation rate in the FDRC and commercial composition at 25° C./60% RH. The FDRC composition is shown at Table 7.

FIG. 12 shows the acidic peak profile at 25° C. for ipilimumab and nivolumab in a pH ranging study.

FIG. 13 shows the size exclusion chromatography high molecular weight profile of DP prototypes from the ruggedness study. The HMW profile of the FDRC DP remained unchanged after 6 months of storage at 2-8° C. and 25° C.

FIG. 14 shows the size exclusion chromatography monomer profile of the FDRC DP after 6 months of storage at 2-8° C. and 25° C.

FIG. 15 shows the ipilimumab acidic peak profile. The evaluation indicates a pH dependence of deamidation at accelerated temperature of 25° C., as indicated by an increase in acidic peak profile at higher temperature range of pH 7.0.

FIG. 16 shows the nivolumab acidic peak profile. The evaluation indicates a pH dependence of deamidation at accelerated temperature of 25° C., as indicated by an increase in acidic peak profile at higher temperature range of pH 7.0.

FIG. 17 shows the ipilimumab main peak profile. The evaluation indicates a pH dependence of deamidation at accelerated temperature of 25° C., as indicated by an increase in acidic peak profile at higher temperature range of pH 7.0.

FIG. 18 shows the nivolumab main peak profile. The evaluation indicates a pH dependence of deamidation at accelerated temperature of 25° C., as indicated by an increase in acidic peak profile at higher temperature range of pH 7.0.

FIG. 19 shows the impact of pH on the cIEF profile.

FIG. 20 shows the iCIEF profile over a pH range of 5.4-6.6.

DETAILED DESCRIPTION OF THE INVENTION

The present invention relates pharmaceutical compositions comprising both an anti-PD-1 antibody and a second antibody. In some embodiments, the composition is a fixed dose formulation. The advantages of such a single-formulation fixed dose composition can include improved medical compliance by reducing the time of treatment (for a composition given, for example, intravenously) or reduced administration burden (e.g., multiple i.v. injections) and the ability to have a combined drug profile for both drugs. However, such a single-formulation fixed dose composition can induce undesirable interactions between the two antibodies, thereby reducing the total amount of active ingredient, as well as a limitation on the ability of a physician to customize doses.

Terms

In order that the present disclosure may be more readily understood, certain terms are first defined. As used in this application, except as otherwise expressly provided herein, each of the following terms shall have the meaning set forth below. Additional definitions are set forth throughout the application.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. The headings provided herein are not limitations of the various aspects of the disclosure, which can be had by reference to the specification as a whole. Accordingly, the terms defined immediately below are more fully defined by reference to the specification in its entirety.

"Administering" refers to the physical introduction of a composition comprising a therapeutic agent to a subject, using any of the various methods and delivery systems known to those skilled in the art. Preferred routes of administration for the formulations disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the formulation is administered via a non-parenteral route, preferably orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

An "adverse event" (AE) as used herein is any unfavorable and generally unintended or undesirable sign (including an abnormal laboratory finding), symptom, or disease associated with the use of a medical treatment. For example, an adverse event may be associated with activation of the immune system or expansion of immune system cells (e.g., T cells) in response to a treatment. A medical treatment may have one or more associated AEs and each AE may have the same or different level of severity. Reference to methods capable of "altering adverse events" means a treatment regime that decreases the incidence and/or severity of one or more AEs associated with the use of a different treatment regime.

An "antibody" (Ab) shall include, without limitation, a glycoprotein immunoglobulin which binds specifically to an antigen and comprises at least two heavy (H) chains and two light (L) chains interconnected by disulfide bonds, or an antigen-binding portion thereof. Each H chain comprises a heavy chain variable region (abbreviated herein as $V_H$) and a heavy chain constant region. The heavy chain constant region comprises three constant domains, $C_{H1}$, $C_{H2}$ and $C_{H3}$. Each light chain comprises a light chain variable region (abbreviated herein as $V_L$) and a light chain constant region. The light chain constant region is comprises one constant domain, $C_L$. The $V_H$ and $V_L$ regions can be further subdivided into regions of hypervariability, termed complementarity determining regions (CDRs), interspersed with regions that are more conserved, termed framework regions (FR). Each $V_H$ and $V_L$ comprises three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

An immunoglobulin may derive from any of the commonly known isotypes, including but not limited to IgA, secretory IgA, IgG and IgM. IgG subclasses are also well known to those in the art and include but are not limited to human IgG1, IgG2, IgG3 and IgG4. "Isotype" refers to the antibody class or subclass (e.g., IgM or IgG1) that is encoded by the heavy chain constant region genes. The term "antibody" includes, by way of example, both naturally occurring and non-naturally occurring antibodies; monoclonal and polyclonal antibodies; chimeric and humanized antibodies; human or nonhuman antibodies; wholly synthetic antibodies; and single chain antibodies. A nonhuman antibody may be humanized by recombinant methods to reduce its immunogenicity in man. Where not expressly stated, and unless the context indicates otherwise, the term "antibody" also includes an antigen-binding fragment or an antigen-binding portion of any of the aforementioned immunoglobulins, and includes a monovalent and a divalent fragment or portion, and a single chain antibody.

The term "monoclonal antibody" ("mAb") refers to a non-naturally occurring preparation of antibody molecules of single molecular composition, i.e., antibody molecules whose primary sequences are essentially identical, and which exhibits a single binding specificity and affinity for a particular epitope. A mAb is an example of an isolated antibody. MAbs may be produced by hybridoma, recombinant, transgenic or other techniques known to those skilled in the art.

A "human" antibody (HuMAb) refers to an antibody having variable regions in which both the framework and CDR regions are derived from human germline immunoglobulin sequences. Furthermore, if the antibody contains a constant region, the constant region is also derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences. The terms "human" antibodies and "fully human" antibodies and are used synonymously.

A "humanized antibody" refers to an antibody in which some, most or all of the amino acids outside the CDR domains of a non-human antibody are replaced with corresponding amino acids derived from human immunoglobulins. In one embodiment of a humanized form of an Ab, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody.

An "anti-antigen" antibody refers to an antibody that binds specifically to the antigen. For example, an anti-PD-1 antibody binds specifically to PD-1 and an anti-CTLA-4 antibody binds specifically to CTLA-4.

An "antigen-binding portion" of an antibody (also called an "antigen-binding fragment") refers to one or more fragments of an antibody that retain the ability to bind specifically to the antigen bound by the whole antibody.

A "cancer" refers a broad group of various diseases characterized by the uncontrolled growth of abnormal cells in the body. Unregulated cell division and growth divide and grow results in the formation of malignant tumors that invade neighboring tissues and may also metastasize to distant parts of the body through the lymphatic system or bloodstream. A "cancer" or "cancer tissue" can include a tumor.

"CD137", "CD-137", "tumor necrosis factor receptor superfamily member 9 (TNFRSF9)", "4-1BB" and "induced by lymphocyte activation (ILA)" all refer to the same member of the tumor necrosis factor receptor family. One activity CD137 has been implicated in is costimulatory activity for activated T cells. (Jang et al. (1998) *Biochem. Biophys. Res. Commun.* 242 (3): 613-20). The term "CD137" as used herein includes human CD137 (hCTLA-4), variants, isoforms, and species homologs of hCD137, and analogs having at least one common epitope with hCD137. The amino acid sequence for hCD137 can be found under GenBank Accession No. NP_001552.

"Cytotoxic T-Lymphocyte Antigen-4" (CTLA-4) refers to an immunoinhibitory receptor belonging to the CD28 family. CTLA-4 is expressed exclusively on T cells in vivo, and binds to two ligands, CD80 and CD86 (also called B7-1 and B7-2, respectively). The term "CTLA-4" as used herein includes human CTLA-4 (hCTLA-4), variants, isoforms, and species homologs of hCTLA-4, and analogs having at least one common epitope with hCTLA-4. The complete hCTLA-4 sequence can be found under GenBank Accession No. AAB59385.

A "disease" refers to any disorder of structure or function in an organism, for example a human that is not the direct result of a physical injury. An "infectious disease" is a disease that is caused by an organism such as a bacterium, fungus, parasite virus or other pathogen.

"Dosing interval," as used herein, means the amount of time that elapses between multiple doses of a formulation disclosed herein being administered to a subject. Dosing interval can thus be indicated as ranges.

The term "dosing frequency" as used herein refers to the frequency of administering doses of a formulation disclosed herein in a given time. Dosing frequency can be indicated as the number of doses per a given time, e.g., once a week or once in two weeks.

The use of the term "fixed dose" with regard to a composition of the invention means that two or more different antibodies in a single composition are present in the composition in particular (fixed) ratios with each other. In some embodiments, the fixed dose is based on the weight (e.g., mg) of the antibodies. In certain embodiments, the fixed dose is based on the concentration (e.g., mg/ml) of the antibodies. In some embodiments, the ratio is at least about 1:1, about 1:2, about 1:3, about 1:4, about 1:5, about 1:6, about 1:7, about 1:8, about 1:9, about 1:10, about 1:15, about 1:20, about 1:30, about 1:40, about 1:50, about 1:60, about 1:70, about 1:80, about 1:90, about 1:100, about 1:120, about 1:140, about 1:160, about 1:180, about 1:200, about 200:1, about 180:1, about 160:1, about 140:1, about 120:1, about 100:1, about 90:1, about 80:1, about 70:1, about 60:1, about 50:1, about 40:1, about 30:1, about 20:1, about 15:1, about 10:1, about 9:1, about 8:1, about 7:1, about 6:1, about 5:1, about 4:1, about 3:1, or about 2:1 mg first antibody to mg second antibody. For example, the 3:1 ratio of a first antibody and a second antibody can mean that a vial can contain about 240 mg of the first antibody and 80 mg of the second antibody or about 3 mg/ml of the first antibody and 1 mg/ml of the second antibody.

The use of the term "flat dose" with regard to the composition of the invention means a dose that is administered to a patient without regard for the weight or body surface area (BSA) of the patient. The flat dose is therefore not provided as a mg/kg dose, but rather as an absolute amount of the agent (e.g., the anti-CTLA4 antibody and/or anti-PD-1 antibody). For example, a 60 kg person and a 100 kg person would receive the same dose of the composition (e.g., 240 mg of an anti-PD-1 antibody and 80 mg of an anti-CTLA4 antibody in a single fixed dosing formulation vial containing both 240 mg of an anti-PD-1 antibody and 80 mg of an anti-CTLA4 antibody (or two fixed dosing formulation vials containing 120 mg of an anti-PD-1 antibody and 40 mg of an anti-CTLA4 antibody, etc)).

The term "weight based dose" as referred to herein means that a dose that is administered to a patient is calculated based on the weight of the patient. For example, when a patient with 60 kg body weight requires 3 mg/kg of an anti-PD-1 antibody in combination with 1 mg/kg of an anti-CTLA4 antibody, one can draw the appropriate amounts of the anti-PD-1 antibody (i.e., 180 mg) and the anti-CTLA4 antibody (i.e., 60 mg) at once from a 3:1 ratio fixed dosing formulation of an anti-PD-1 antibody and an anti-CTLA4 antibody.

The term "reference composition" as used herein refers to a composition comprising either the first antibody or the second antibody, but not both. The reference composition can comprise the same components of the composition comprising the first antibody and the second antibody except the presence of one antibody. In other embodiments, the reference composition is a commercially available, corresponding composition, e.g., OPDIVO® or KEYRUDA® for anti-PD-1 antibody or YERVOY® for anti-CTLA-4 antibody.

The term "GITR", "tumor necrosis factor receptor superfamily member 18", "activation-inducible TNFR family receptor" or "glucocorticoid-induced TNFR-related protein" all refer to a protein that is a member of the tumor necrosis factor receptor super family. GITR is encoded for by the TNFRSF18 gene in humans. It is a 241 amino acid type I transmembrane protein characterized by three cysteine pseudo-repeats in the extracellular domain and specifically protects T-cell receptor-induced apoptosis, although it does not protect cells from other apoptotic signals, including Fas triggering, dexamethasone treatment, or UV irradiation (Nocentini, G, et al. (1997) *Proc. Natl. Acad. Sci, USA* 94:6216-622). The term GITR as used herein includes human GITR (hGITR), variants, isoforms, and species homologs of hGITR, and analogs having at least one common epitope with hGITR. Three isoforms of hGITR have been identified, all of which share the same extracellular domain, except for its C-terminal portion. Variant 1 (Accession No. NP_004186) consists of 241 amino acids and represents the longest transcript. It contains an extra coding segment that leads to a frame shift, compared to variant 2. The resulting protein (isoform 1) contains a distinct and shorter C-terminus, as compared to isoform 2. Variant 2 (Accession No. NP_683699) encodes the longest protein (isoform 2), consisting of 255 amino acids, and is soluble. Variant 3 (Accession No. NP_683700) contains an extra coding segment that leads to a frame shift, compared to variant 2. The resulting protein (isoform 3) contains a distinct and shorter C-terminus, as compared to isoform 2, and consists of 234 amino acids.

The term "immunotherapy" refers to the treatment of a subject afflicted with, or at risk of contracting or suffering a recurrence of, a disease by a method comprising inducing, enhancing, suppressing or otherwise modifying an immune response.

The term "LAG3", "LAG-3" or "Lymphocyte Activation Gene-3" refers to Lymphocyte Activation Gene-3. The term LAG-3 as used herein includes human LAG-3 (hLAG-3), variants, isoforms, and species homologs of hLAG-3, and analogs having at least one common epitope with hLAG-3. The term "human LAG-3" refers to human sequence LAG-3, such as the complete amino acid sequence of human LAG-3 having Genbank Accession No. NP 002277. The term "mouse LAG-3" refers to mouse sequence LAG-3, such as the complete amino acid sequence of mouse LAG-3 having Genbank Accession No. NP_032505. LAG-3 is also known in the art as, for example, CD223. The human LAG-3 sequence may differ from human LAG-3 of Genbank Accession No. NP_002277 by having, e.g., conserved mutations or mutations in non-conserved regions and the LAG-3 has substantially the same biological function as the human LAG-3 of Genbank Accession No. NP_002277. For example, a biological function of human LAG-3 is having an epitope in the extracellular domain of LAG-3 that is specifically bound by an antibody of the instant disclosure or a biological function of human LAG-3 is binding to MEW Class II molecules.

The term "lyophilisate" as used herein in connection with the formulation according to the invention denotes a formulation which is manufactured by freeze-drying methods known in the art per se. The solvent (e.g., water) is removed by freezing following sublimation under vacuum and desorption of residual water at elevated temperature. In the pharmaceutical field, the lyophilisate has usually residual moisture of about 0.1 to 5% (w/w) and is present as a powder or a physical stable cake. The lyophilisate is characterized by a fast dissolution after addition of a reconstitution medium.

The term "Killer Ig-like Receptor", "Killer Inhibitory Receptor", or "KIR", refers to a protein or polypeptide encoded by a gene that is a member of the KIR gene family or by a cDNA prepared from such a gene. A detailed review of the KIR gene family, including the nomenclature of KIR genes and KIR gene products, and Genbank accession numbers for exemplary KIRs, is "The KIR Gene Cluster" by M. Carrington and P. Norman, available at the NCBI website called Bookshelf (accessible at ncbi.nlm.nih.gov/books). The term KIR as used herein includes human KIR (hKIR), variants, isoforms, and species homologs of hKIR, and analogs having at least one common epitope with hKIR. The sequences of human KIR genes and cDNAs, as well as their protein products, are available in public databases, including GenBank. Non-limiting exemplary GenBank entries of human KIRs have the following accession numbers: KIR2DL1: Genbank accession number U24076, NM_014218, AAR16197, or L41267; KIR2DL2: Genbank accession number U24075 or L76669; KIR2DL3: Genbank accession number U24074 or L41268; KIR2DL4: Genbank accession number X97229; KIR2DS1: Genbank accession number X89892; KIR2DS2: Genbank accession number L76667; KIR2DS3: Genbank accession number NM_012312 or L76670 (splice variant); KIR3DL1: Genbank accession number L41269; and KIR2DS4: Genbank accession number AAR26325. A KIR may comprise from 1 to 3 extracellular domains, and may have a long (i.e., more than 40 amino acids) or short (i.e., less than 40 amino acids) cytoplasmic tail. As previously described herein, these features determine the nomenclature of a KIR. KIR is further described in Int'l Publ. No. WO/2014/055648, which is incorporated herein by reference in its entirety.

"Programmed Death-1 (PD-1)" refers to an immunoinhibitory receptor belonging to the CD28 family. PD-1 is expressed predominantly on previously activated T cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1. The complete hPD-1 sequence can be found under GenBank Accession No. U64863. "PD-1" and "PD-1 receptor" are used interchangeably herein.

"Programmed Death Ligand-1 (PD-L1)" is one of two cell surface glycoprotein ligands for PD-1 (the other being PD-L2) that down-regulate T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1. The complete hPD-L1 sequence can be found under GenBank Accession No. Q9NZQ7.

The term "reconstituted formulation" as used herein denotes a formulation which is lyophilized and re-dissolved by addition of a diluent. The diluent can contain, for example, 0.9% Sodium Chloride Injection, USP or 5% Dextrose Injection, USP.

A "subject" includes any human or nonhuman animal. The term "nonhuman animal" includes, but is not limited to, vertebrates such as nonhuman primates, sheep, dogs, and rodents such as mice, rats and guinea pigs. In some embodiments, the subject is a human. The terms, "subject" and "patient" are used interchangeably herein.

A "therapeutically effective amount" or "therapeutically effective dosage" of a drug or therapeutic agent is any amount of the drug that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

As used herein, "subtherapeutic dose" means a dose of a therapeutic compound (e.g., an antibody) that is lower than the usual or typical dose of the therapeutic compound when administered alone for the treatment of a hyperproliferative disease (e.g., cancer).

"Treatment" or "therapy" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease.

The use of the alternative (e.g., "or") should be understood to mean either one, both, or any combination thereof of the alternatives. As used herein, the indefinite articles "a" or "an" should be understood to refer to "one or more" of any recited or enumerated component.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 10% or 20% (i.e., ±10% or ±20%). For example, about 3 mg can include any number between 2.7 mg and 3.3 mg (for 10%) or between 2.4 mg and 3.6 mg (for 20%). Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

The terms "once about every week," "once about every two weeks," or any other similar dosing interval terms as used herein mean approximate numbers. "Once about every week" can include every seven days±one day, i.e., every six days to every eight days. "Once about every two weeks" can include every fourteen days±three days, i.e., every eleven days to every seventeen days. Similar approximations apply, for example, to once about every three weeks, once about every four weeks, once about every five weeks, once about every six weeks and once about every twelve weeks. In some embodiments, a dosing interval of once about every six weeks or once about every twelve weeks means that the first dose can be administered any day in the first week, and then the next dose can be administered any day in the sixth or twelfth week, respectively. In other embodiments, a dosing interval of once about every six weeks or once about every twelve weeks means that the first dose is administered on a particular day of the first week (e.g., Monday) and then the next dose is administered on the same day of the sixth or twelfth weeks (i.e., Monday), respectively.

As described herein, any concentration range, percentage range, ratio range or integer range is to be understood to include the value of any integer within the recited range and, when appropriate, fractions thereof (such as one tenth and one hundredth of an integer), unless otherwise indicated.

Various aspects of the invention are described in further detail in the following subsections.

Anti-PD-1 and Anti-PD-L1 Antibodies

The composition of the invention includes a first antibody and a second antibody at a ratio between 1:100 to 100:1. In one aspect, the first antibody is an anti-PD-1 antibody or an anti-PD-L1 antibody. PD-1 is a key immune checkpoint receptor expressed by activated T and B cells and mediates immunosuppression. PD-1 is a member of the CD28 family of receptors, which includes CD28, CTLA-4, ICOS, PD-1, and BTLA. Two cell surface glycoprotein ligands for PD-1 have been identified, Programmed Death Ligand-1 (PD-L1) and Programmed Death Ligand-2 (PD-L2), that are expressed on antigen-presenting cells as well as many human cancers and have been shown to down regulate T cell activation and cytokine secretion upon binding to PD-1. Inhibition of the PD-1/PD-L1 interaction mediates potent antitumor activity in preclinical models.

HuMAbs that bind specifically to PD-1 with high affinity have been disclosed in U.S. Pat. Nos. 8,008,449 and 8,779,105. Other anti-PD-1 mAbs have been described in, for example, U.S. Pat. Nos. 6,808,710, 7,488,802, 8,168,757 and 8,354,509, and PCT Publication No. WO 2012/145493. Each of the anti-PD-1 HuMAbs disclosed in U.S. Pat. No. 8,008,449 has been demonstrated to exhibit one or more of the following characteristics: (a) binds to human PD-1 with a $K_D$ of $1 \times 10^{-7}$M or less, as determined by surface plasmon resonance using a Biacore biosensor system; (b) does not substantially bind to human CD28, CTLA-4 or ICOS; (c) increases T-cell proliferation in a Mixed Lymphocyte Reaction (MLR) assay; (d) increases interferon-γ production in an MLR assay; (e) increases IL-2 secretion in an MLR assay; (f) binds to human PD-1 and cynomolgus monkey PD-1; (g) inhibits the binding of PD-L1 and/or PD-L2 to PD-1; (h) stimulates antigen-specific memory responses; (i) stimulates Ab responses; and (j) inhibits tumor cell growth in vivo. Anti-PD-1 antibodies useful for the present invention include mAbs that bind specifically to human PD-1 and exhibit at least one, preferably at least five, of the preceding characteristics.

In one embodiment, the anti-PD-1 antibody is nivolumab. Nivolumab (also known as "OPDIVO®"; formerly designated 5C4, BMS-936558, MDX-1106, or ONO-4538) is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al., 2014 Cancer Immunol Res. 2(9): 846-56). In another embodiment, the anti-PD-1 antibody or fragment thereof cross-competes with nivolumab. In other embodiments, the anti-PD-1 antibody or fragment thereof binds to the same epitope as nivolumab. In certain embodiments, the anti-PD-1 antibody has the same CDRs as nivolumab.

In another embodiment, the anti-PD-1 antibody or fragment thereof cross-competes with pembrolizumab. In some embodiments, the anti-PD-1 antibody or fragment thereof binds to the same epitope as pembrolizumab. In certain embodiments, the anti-PD-1 antibody has the same CDRs as pembrolizumab. In another embodiment, the anti-PD-1 antibody is pembrolizumab. Pembrolizumab (also known as KEYTRUDA®, lambrolizumab, and MK-3475) is a humanized monoclonal IgG4 antibody directed against human cell surface receptor PD-1 (programmed death-1 or programmed cell death-1). Pembrolizumab is described, for example, in U.S. Pat. Nos. 8,354,509 and 8,900,587; see also http://www.cancer.gov/drugdictionary?cdrid=695789 (last accessed: Dec. 14, 2014). Pembrolizumab has been approved by the FDA for the treatment of relapsed or refractory melanoma.

In other embodiments, the anti-PD-1 antibody or fragment thereof cross-competes with MEDI0608. In still other embodiments, the anti-PD-1 antibody or fragment thereof binds to the same epitope as MEDI0608. In certain embodiments, the anti-PD-1 antibody has the same CDRs as MEDI0608. In other embodiments, the anti-PD-1 antibody is MEDI0608 (formerly AMP-514), which is a monoclonal antibody. MEDI0608 is described, for example, in U.S. Pat. No. 8,609,089B2 or in http://www.cancer.gov/drugdictionary?cdrid=756047 (last accessed Dec. 14, 2014).

In certain embodiments, the first antibody is an anti-PD-1 antagonist. One example of the anti-PD-1 antagonist is AMP-224, which is a B7-DC Fc fusion protein. AMP-224 is discussed in U.S. Publ. No. 2013/0017199 or in http://www.cancer.gov/publications/dictionaries/cancer-drug?cdrid=700595 (last accessed Jul. 8, 2015).

In other embodiments, the anti-PD-1 antibody or fragment thereof cross-competes with BGB-A317. In some embodiments, the anti-PD-1 antibody or fragment thereof binds the same epitope as BGB-A317. In certain embodiments, the anti-PD-1 antibody has the same CDRs as BGB-A317. In certain embodiments, the anti-PD-1 antibody is BGB-A317, which is a humanized monoclonal antibody. BGB-A317 is described in U.S. Publ. No. 2015/0079109.

Anti-PD-1 antibodies useful for the disclosed compositions also include isolated antibodies that bind specifically to human PD-1 and cross-compete for binding to human PD-1 with nivolumab (see, e.g., U.S. Pat. Nos. 8,008,449 and 8,779,105; WO 2013/173223). The ability of antibodies to cross-compete for binding to an antigen indicates that these antibodies bind to the same epitope region of the antigen and sterically hinder the binding of other cross-competing antibodies to that particular epitope region. These cross-competing antibodies are expected to have functional properties very similar to those of nivolumab by virtue of their binding to the same epitope region of PD-1. Cross-competing antibodies can be readily identified based on their ability to cross-compete with nivolumab in standard PD-1 binding assays such as Biacore analysis, ELISA assays or flow cytometry (see, e.g., WO 2013/173223).

In certain embodiments, the antibodies that cross-compete for binding to human PD-1 with, or bind to the same epitope region of human PD-1 as, nivolumab are mAbs. For administration to human subjects, these cross-competing antibodies can be chimeric antibodies, or humanized or human antibodies. Such chimeric, humanized or human mAbs can be prepared and isolated by methods well known in the art.

Anti-PD-1 antibodies useful for the compositions of the disclosed invention also include antigen-binding portions of the above antibodies. It has been amply demonstrated that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; and (iv) a Fv fragment consisting of the $V_L$ and $V_H$ domains of a single arm of an antibody.

Anti-PD-1 antibodies suitable for use in the disclosed compositions are antibodies that bind to PD-1 with high specificity and affinity, block the binding of PD-L1 and or PD-L2, and inhibit the immunosuppressive effect of the PD-1 signaling pathway. In any of the compositions or methods disclosed herein, an anti-PD-1 "antibody" includes an antigen-binding portion or fragment that binds to the PD-1 receptor and exhibits the functional properties similar to those of whole antibodies in inhibiting ligand binding and upregulating the immune system. In certain embodiments, the anti-PD-1 antibody or antigen-binding portion thereof cross-competes with nivolumab for binding to human PD-1. In other embodiments, the anti-PD-1 antibody or antigen-binding portion thereof is a chimeric, humanized or human monoclonal antibody or a portion thereof. In certain embodiments, the antibody is a humanized antibody. In other embodiments, the antibody is a human antibody. Antibodies of an IgG1, IgG2, IgG3 or IgG4 isotype can be used.

In certain embodiments, the anti-PD-1 antibody or antigen-binding portion thereof comprises a heavy chain constant region which is of a human IgG1 or IgG4 isotype. In certain other embodiments, the sequence of the IgG4 heavy chain constant region of the anti-PD-1 antibody or antigen-binding portion thereof contains an S228P mutation which replaces a serine residue in the hinge region with the proline residue normally found at the corresponding position in IgG1 isotype antibodies. This mutation, which is present in nivolumab, prevents Fab arm exchange with endogenous IgG4 antibodies, while retaining the low affinity for activating Fc receptors associated with wild-type IgG4 antibodies (Wang et al., 2014). In yet other embodiments, the antibody comprises a light chain constant region which is a human kappa or lambda constant region. In other embodiments, the anti-PD-1 antibody or antigen-binding portion thereof is a mAb or an antigen-binding portion thereof. In certain embodiments of any of the therapeutic methods described herein comprising administration of an anti-PD-1 antibody, the anti-PD-1 antibody is nivolumab. In other embodiments, the anti-PD-1 antibody is pembrolizumab. In other embodiments, the anti-PD-1 antibody is chosen from the human antibodies 17D8, 2D3, 4H1, 4A11, 7D3 and 5F4 described in U.S. Pat. No. 8,008,449. In still other embodiments, the anti-PD-1 antibody is MEDI0608 (formerly AMP-514), AMP-224, or Pidilizumab (CT-011).

In certain embodiments, the first antibody for the disclosed composition is an anti-PD-L1 antibody. Because anti-PD-1 and anti-PD-L1 target the same signaling pathway and have been shown in clinical trials to exhibit similar levels of efficacy in a variety of cancers, an anti-PD-L1 antibody can be substituted for the anti-PD-1 antibody in any of the therapeutic methods or compositions disclosed herein. In certain embodiments, the anti-PD-L1 antibody is BMS-936559 (formerly 12A4 or MDX-1105) (see, e.g., U.S. Pat. No. 7,943,743; WO 2013/173223). In other embodiments, the anti-PD-L1 antibody is MPDL3280A (also known as RG7446 and atezolizumab) (see, e.g., Herbst et al. 2013 *J Clin Oncol* 31(suppl):3000; U.S. Pat. No. 8,217,149), MEDI4736 (Khleif, 2013, In: Proceedings from the European Cancer Congress 2013; Sep. 27-Oct. 1, 2013; Amsterdam, The Netherlands. Abstract 802) or MSB0010718C (also called Avelumab; See US 2014/0341917). In certain embodiments, the antibodies that cross-compete for binding to human PD-L1 with, or bind to the same epitope region of human PD-L1 as the above-references PD-L1 antibodies are mAbs. For administration to human subjects, these cross-competing antibodies can be chimeric antibodies, or can be humanized or human antibodies. Such chimeric, humanized or human mAbs can be prepared and isolated by methods well known in the art.

Anti-CTLA-4 Antibodies

Anti-CTLA-4 antibodies used for the instant invention bind to human CTLA-4 so as to disrupt the interaction of CTLA-4 with a human B7 receptor. Because the interaction of CTLA-4 with B7 transduces a signal leading to inactivation of T-cells bearing the CTLA-4 receptor, disruption of the interaction effectively induces, enhances or prolongs the activation of such T cells, thereby inducing, enhancing or prolonging an immune response.

HuMAbs that bind specifically to CTLA-4 with high affinity have been disclosed in U.S. Pat. Nos. 6,984,720 and 7,605,238. Other anti-CTLA-4 mAbs have been described in, for example, U.S. Pat. Nos. 5,977,318, 6,051,227, 6,682,736, and 7,034,121. The anti-CTLA-4 HuMAbs disclosed in U.S. Pat. Nos. 6,984,720, 7,605,238 have been demonstrated to exhibit one or more of the following characteristics: (a) binds specifically to human CTLA-4 with a binding affinity reflected by an equilibrium association constant ($K_a$) of at least about $10^7 M^{-1}$, or about $10^9 M^{-1}$, or about $10^{11} M^{-1}$ to $10^{11} M^{-1}$ or higher, as determined by Biacore analysis; (b) a kinetic association constant ($k_a$) of at least about $10^3$, about $10^4$, or about $10^5$ $m^{-1}$ $s^{-1}$; (c) a kinetic disassociation constant ($k_d$) of at least about $10^3$, about $10^4$, or about $10^5$ $m^{-1}$ $s^{-1}$; and (d) inhibits the binding of CTLA-4 to B7-1 (CD80) and B7-2 (CD86). Anti-CTLA-4 antibodies useful for the present invention include mAbs that bind specifically to human CTLA-4 and exhibit at least one, at least two, or at least three of the preceding characteristics. An exemplary clinical anti-CTLA-4 antibody is the human mAb 10D1 (now known as ipilimumab and marketed as YERVOY®) as disclosed in U.S. Pat. No. 6,984,720.

An exemplary clinical anti-CTLA-4 antibody is the human mAb 10D1 (now known as ipilimumab and marketed as YERVOY®) as disclosed in U.S. Pat. No. 6,984,720. Ipilimumab is an anti-CTLA-4 antibody for use in the methods disclosed herein. Ipilimumab is a fully human, IgG1 monoclonal antibody that blocks the binding of CTLA-4 to its B7 ligands, thereby stimulating T cell activation and improving overall survival (OS) in patients with advanced melanoma.

Another anti-CTLA-4 antibody useful for the present methods is tremelimumab (also known as CP-675,206). Tremelimumab is human IgG2 monoclonal anti-CTLA-4 antibody. Tremelimumab is described in WO/2012/122444, U.S. Publ. No. 2012/263677, or WO Publ. No. 2007/113648 A2.

Anti-CTLA-4 antibodies useful for the disclosed composition also include isolated antibodies that bind specifically to human CTLA-4 and cross-compete for binding to human CTLA-4 with ipilimumab or tremelimumab or bind to the same epitope region of human CTLA-4 as ipilimumab or tremelimumab. In certain embodiments, the antibodies that cross-compete for binding to human CTLA-4 with, or bind to the same epitope region of human CTLA-4 as does ipilimumab or tremelimumab, are antibodies comprising a heavy chain of the human IgG1 isotype. For administration to human subjects, these cross-competing antibodies are chimeric antibodies, or humanized or human antibodies. Useful anti-CTLA-4 antibodies also include antigen-binding portions of the above antibodies such as Fab, $F(ab')_2$, Fd or Fv fragments.

Anti-LAG-3 Antibodies

Anti-LAG-3 antibodies of the instant invention bind to human LAG-3. Antibodies that bind to LAG-3 have been disclosed in Int'l Publ. No. WO/2015/042246 and U.S. Publ. Nos. 2014/0093511 and 2011/0150892.

An exemplary LAG-3 antibodies useful for the present invention is 25F7 (described in U.S. Publ. No. 2011/0150892). An additional exemplary LAG-3 antibody useful for the present invention is BMS-986016. In one embodiment, an anti-LAG-3 antibody useful for the composition cross-competes with 25F7 or BMS-986016. In another embodiment, an anti-LAG-3 antibody useful for the composition binds to the same epitope as 25F7 or BMS-986016. In other embodiments, an anti-LAG-3 antibody comprises six CDRs of 25F7 or BMS-986016.

Anti-CD137 Antibodies

Anti-CD137 antibodies specifically bind to and activate CD137-expressing immune cells, stimulating an immune response, in particular a cytotoxic T cell response, against tumor cells. Antibodies that bind to CD137 have been disclosed in U.S. Publ. No. 2005/0095244 and U.S. Pat. Nos. 7,288,638, 6,887,673, 7,214,493, 6,303,121, 6,569,997, 6,905,685, 6,355,476, 6,362,325, 6,974,863, and 6,210,669.

In some embodiments, the anti-CD137 antibody is urelumab (BMS-663513), described in U.S. Pat. No. 7,288,638 (20H4.9-IgG4 [1007 or BMS-663513]). In some embodiments, the anti-CD137 antibody is BMS-663031 (20H4.9-IgG1), described in U.S. Pat. No. 7,288,638. In some embodiments, the anti-CD137 antibody is 4E9 or BMS-554271, described in U.S. Pat. No. 6,887,673. In some embodiments, the anti-CD137 antibody is an antibody disclosed in U.S. Pat. Nos. 7,214,493; 6,303,121; 6,569,997; 6,905,685; or 6,355,476. In some embodiments, the anti-CD137 antibody is 1D8 or BMS-469492; 3H3 or BMS-469497; or 3E1, described in U.S. Pat. No. 6,362,325. In some embodiments, the anti-CD137 antibody is an antibody disclosed in issued U.S. Pat. No. 6,974,863 (such as 53A2). In some embodiments, the anti-CD137 antibody is an antibody disclosed in issued U.S. Pat. No. 6,210,669 (such as 1D8, 3B8, or 3E1). In some embodiments, the antibody is Pfizer's PF-05082566 (PF-2566) In other embodiments, an anti-CD137 antibody useful for the invention cross-competes with the anti-CD137 antibodies disclosed herein. In some embodiments, an anti-CD137 antibody binds to the same epitope as the anti-CD137 antibody disclosed herein. In other embodiments, an anti-CD137 antibody useful for the invention comprises six CDRs of the anti-CD137 antibodies disclosed herein.

Anti-KIR Antibodies

Antibodies that bind specifically to KIR block interaction between Killer-cell immunoglobulin-like receptors (KIR) on NK cells with their ligands. Blocking these receptors facilitates activation of NK cells and, potentially, destruction of tumor cells by the latter. Examples of anti-KIR antibodies have been disclosed in Int'l Publ. Nos. WO/2014/055648, WO 2005/003168, WO 2005/009465, WO 2006/072625, WO 2006/072626, WO 2007/042573, WO 2008/084106, WO 2010/065939, WO 2012/071411 and WO/2012/160448.

One anti-KIR antibody useful for the present invention is lirilumab (also referred to as BMS-986015, IPH2102, or the S241P variant of 1-7F9), first described in Int'l Publ. No. WO 2008/084106. An additional anti-KIR antibody useful for the present invention is 1-7F9 (also referred to as IPH2101), described in Int'l Publ. No. WO 2006/003179. In one embodiment, an anti-KIR antibody for the present composition cross competes for binding to KIR with lirilumab or I-7F9. In another embodiment, an anti-KIR antibody binds to the same epitope as lirilumab or I-7F9. In other embodiments, an anti-KIR antibody comprises six CDRs of lirilumab or I-7F9.

Anti-GITR Antibodies

Anti-GITR antibodies for combining with an anti-PD-1 antibody in a fixed dose may be any anti-GITR antibody that binds specifically to human GITR target and activate the glucocorticoid-induced tumor necrosis factor receptor (GITR). GITR is a member of the TNF receptor superfamily that is expressed on the surface of multiple types of immune cells, including regulatory T cells, effector T cells, B cells, natural killer (NK) cells, and activated dendritic cells ("anti-GITR agonist antibodies"). Specifically, GITR activation increases the proliferation and function of effector T cells, as well as abrogating the suppression induced by activated T regulatory cells. In addition, GITR stimulation promotes anti-tumor immunity by increasing the activity of other immune cells such as NK cells, antigen presenting cells, and B cells. Examples of anti-GITR antibodies have been disclosed in Int'l Publ. Nos. WO/2015/031667, WO2015/184, 099, WO2015/026,684, WO11/028683 and WO/2006/

105021, U.S. Pat. Nos. 7,812,135 and 8,388,967 and U.S. Publ. Nos. 2009/0136494, 2014/0220002, 2013/0183321 and 2014/0348841.

In one embodiment, an anti-GITR antibody useful for the present invention is TRX518 (described in, for example, Schaer et al. *Curr Opin Immunol.* (2012) April; 24(2): 217-224, and WO/2006/105021). In another embodiment, an anti-GITR antibody useful for the present invention is MK4166 or MK1248 and antibodies described in WO11/028683 and in U.S. Pat. No. 8,709,424, and comprising, e.g., a VH chain comprising SEQ ID NO: 104 and a VL chain comprising SEQ ID NO: 105, wherein the SEQ ID NOs are from WO11/028683 or U.S. Pat. No. 8,709,424). In certain embodiments, an anti-GITR antibody is an anti-GITR antibody that is disclosed in WO2015/031667, e.g., an antibody comprising VH CDRs 1-3 comprising SEQ ID Nos.: 31, 71 and 63 of WO2015/031667, respectively, and VL CDRs 1-3 comprising SEQ ID Nos.: 5, 14 and 30 of WO2015/031667. In certain embodiments, an anti-GITR antibody is an anti-GITR antibody that is disclosed in WO2015/184099, e.g., antibody Hum231 #1 or Hum231 #2, or the CDRs thereof, or a derivative thereof (e.g., pab1967, pab1975 or pab1979). In certain embodiments, an anti-GITR antibody is an anti-GITR antibody that is disclosed in JP2008278814, WO09/009116, WO2013/039954, US20140072566, US20140072565, US20140065152, or WO2015/026684, or is INBRX-110 (INHIBRx), LKZ-145 (Novartis), or MEDI-1873 (MedImmune). In certain embodiments, an anti-GITR antibody is an anti-GITR antibody that is described in PCT/US2015/033991 (e.g., an antibody comprising the variable regions of 28F3, 18E10 or 19D3). For example, an anti-GITR antibody may be an antibody comprising the following VH and VL chains or the CDRs thereof:

VH:
(SEQ ID NO: 1)
QVQLVESGGGVVQPGRSLRLSCAASGFTESSYGMHWVRQAPGKGLEWVAV

IWYEGSNKYYADSVKGRFTISRDNSKNTLYLQMNSLRAEDTAVYYCARGG

SMVRGDYYYGMDVWGQGTTVTVS,
and

VL:
(SEQ ID NO: 2)
AIQLTQSPSSLSASVGDRVTITCRASQGISSALAWYQQKPGKAPKWYDAS

SLESGVPSRFSGSGSGTDFTLTISSLQPEDFATYYCQQFNSYPYTFGQGT

KLEIK;
or

VH:
(SEQ ID NO: 3)
QVQLVESGGGVVQPGRSLRLSCAASGFTESSYGFHWVRQAPGKGLEWVAV

IWYAGSNKFYADSVKGRFTISRDNSKNTLYLQMNSLRAEDTAVYYCARGG

QLDYYYYVMDVWGQGTTVTVSS,
and

VL:
(SEQ ID NO: 4)
DIQMTQSPSSLSASVGDRVTITCRASQGISSWLAWYQQKPEKAPKSLIYA

ASSLQSGVPSRFSGSGSGTDFTLTISSLQPEDFATYYCQQYNSYPYTFGQ

GTKLEIK;
or

VH:
(SEQ ID NO: 5)
VQLVESGGGVVQPGRSLRLSCAASGFTFSSYGMEIWVRQAPGKGLEWVAV

IWYAGSNKYYADSVKGRFTISRDNSKNTLYLQMNSLRAEDTAVYYCARGG

RIAVAFYYSMDVWGQGTTVTVSS,
and

VL:
(SEQ ID NO: 6)
DIQMTQSPSSLSASVGDRVTITCRASQGISSWLAWYQQKPEKAPKSLIYA

ASSLQSGVPSRFSGSGSGTDFTLTISSLQPEDFATYYCQQYNSYPYTFGQ

GTKLEIK.

In certain embodiments, an antibody comprising a pair of the above VH and VL light chains, or their CDRs, comprises a heavy chain constant region of an IgG1 isotype, either wild type or mutated, e.g., to be effectorless. In one embodiment, an anti-GITR antibody comprises the following heavy and light chains amino acid sequences:

heavy chain:
(SEQ ID NO: 7)
QVQLVESGGGVVQPGRSLRLSCAASGFTFSSYGMHWVRQAPGKGLEWVAVI

WYEGSNKYYADSVKGRFTISRDNSKNTLYLQMNSLRAEDTAVYYCARGGSM

VRGDYYYGMDVWGQGTTVTVSSASTKGPSVFPLAPCSRSTSESTAALGCLV

KDYFPEPVTVSWNSGALTSGVHTFPAVLQSSGLYSLSSVVTVPSSNFGTQT

YTCNVDHKPSNTKVDKTVERKCCVECPPCPAPPVAGPSVFLFPPKPKDTLM

ISRTPEVTCVVVDVSHEDPEVQFNWYVDGVEVHNAKTKPREEQFNSTFRVV

SVLTVVHQDWLNGKEYKCKVSNKGLPAPIEKTISKTKGQPREPQVYTLPPS

REEMTKNQVSLTCLVKGFYPSDIAVEWESNGQPENNYKTTPPMLDSDGSFF

LYSKLTVDKSRWQQGNVFSCSVMHEALHNHYTQKSLSLSPG,
and light chain:
(SEQ ID NO: 8)
AIQLTQSPSSLSASVGDRVTITCRASQGISSALAWYQQKPGKAPKLLIYD

ASSLESGVPSRFSGSGSGTDFTLTISSLQPEDFATYYCQQFNSYPYTFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC,
or heavy chain:
(SEQ ID NO: 9)
QVQLVESGGGVVQPGRSLRLSCAASGFTFSSYGMHWVRQAPGKGLEWVAVI

WYEGSNKYYADSVKGRFTISRDNSKNTLYLQMNSLRAEDTAVYYCARGGSM

VRGDYYYGMDVWGQGTTVTVSSASTKGPSVFPLAPSSKSTSGGTAALGCLV

KDYFPEPVTVSWNSGALTSGVHTFPAVLQSSGLYSLSSVVTVPSSSLGTQT

YICNVNHKPSNTKVDKRVEPKSCDKTHTCPPCPAPEAEGAPSVFLEPPKPK

DTLMISRTPEVTCVVVDVSHEDPEVKFNWYVDGVEVHNAKTKPREEQYNST

YRVVSVLTVLHQDWLNGKEYKCKVSNKALPSSIEKTISKAKGQPREPQVYT

-continued

LPPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG,
and light chain:

(SEQ ID NO: 8)
AIQLTQSPSSLSASVGDRVTITCRASQGISSALAWYQQKPGKAPKLLIYDA

SSLESGVPSRFSGSGSGTDFTLTISSLQPEDFATYYCQQFNSYPYTFGQGT

KLEIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGEC.

In certain embodiments, an anti-GITR antibody for the present composition cross-competes with an anti-GITR antibody described herein, e.g., TRX518, MK4166 or an antibody comprising a VH domain and a VL domain amino acid sequence described herein. In some embodiments, an anti-GITR antibody for the present composition binds the same epitope as that of an anti-GITR antibody described herein, e.g., TRX518, MK4166 or an antibody comprising a VH domain and a VL domain amino acid sequence described herein. In certain embodiments, an anti-GITR antibody comprises the six CDRs of TRX518, MK4166 or those of an antibody comprising a VH domain and a VL domain amino acid sequence described herein. An exemplary pharmaceutical composition comprises an anti-PD-1 antibody, e.g., nivolumab, MK-3475 (pembrolizumab) or atezolizumab, and an anti-GITR agonist antibody, e.g., TRX518, MK4166 or an antibody comprising a VH domain and a VL domain amino acid sequence described herein, wherein the ratio of the amount (e.g., concentration (e.g., mg/ml) or weight (e.g., mg)) of the anti-PD-1 antibody to the amount of the anti-GITR antibody (e.g., concentration (e.g., mg/ml) or weight (e.g., mg), respectively) is from about 1:1-20; about 1:1-10; about 1:1-5; about 1:2-5; about 1:2-3; about 1:3-5; about 1-20:1; about 1-10:1; about 1-5:1; about 2-5:1; about 2-3:1; or about 3-5:1. For example, the ratio of (i) an anti-PD-1 or anti-PD-L1 antibody to (2) an anti-GITR antibody, may be 1:10, 1:9, 1:8, 1:7, 1:6, 1:5, 1:4, 1:3, 1:2, 1:1, 2:1, 3:1, 4:1, 5:1, 6:1, 7:1, 8:1, 9:1 or 10:1. ":" refers to "to," e.g., "1:1-20" refers to a ratio of 1 to a number selected from 1-20. The combination may be administered weekly, biweekly, once every three weeks or monthly.

In certain embodiments, an anti-PD-1 or anti-PD-L1 antibody e.g., nivolumab, pembrolizumab or atezolizumab, is co-formulated with an anti-GITR antibody, wherein the anti-GITR antibody is at a dose, e.g., flat dose, of 0.1 to 1000 mg, such as 0.1 to 100 mg, 0.5 to 100 mg, 1 to 100 mg, 5 to 100 mg, 10 to 100 mg, 50 to 100 mg, 0.1 to 300 mg, 0.5 to 300 mg, 1 to 300 mg, 5 to 300 mg, 10 to 300 mg, 50 to 300 mg, 100 to 300 mg or 200 to 300 mg. Exemplary amounts of anti-GITR antibody that may be co-formulated with an anti-PD-1 or anti-PD-L1 antibody include about 0.1 mg, about 0.3 mg, about 0.5 mg, about 1 mg, about 3 mg, about 10 mg, about 30 mg, about 100 mg, about 200 mg, about 240 mg, about 250 mg, about 300 mg, about 400 mg, about 500 mg, about 600 mg, about 700 mg, about 800 mg, about 900 mg or about 1000 mg. In certain embodiments, an anti-PD-1 or anti-PD-L1 antibody is co-formulated with an anti-GITR antibody, wherein the dose of the anti-PD-1 or PD-L1 antibody, is a dose (e.g., flat dose) of 100-300 mg, such as, 200-300 mg, 220-260 mg, 230-250 mg or 240 mg, such as about 60 mg, about 80 mg, about 100 mg, about 120 mg, about 140 mg, about 160 mg, about 180 mg, about 200 mg, about 220 mg, about 240 mg, about 260 mg, about 280 or about 300 mg.

In exemplary embodiments, an anti-PD-1 or anti-PD-L1 antibody, e.g., nivolumab, pembrolizumab or atezolizumab, is co-formulated with an anti-GITR antibody, e.g., an antibody comprising (i) a VH and a VL domain comprising the amino acid sequences of SEQ ID Nos.: 1 and 2, respectively, SEQ ID Nos.: 3 and 4, respectively, or SEQ ID Nos.: 5 and 6, respectively; or the VH CDR1, CDR2, CDR3 and the VL CDR1, CDR2 and CDR3 of any of these pairs of variable regions, or (ii) the heavy and light chains comprising the amino acid sequences of SEQ ID Nos. 7 and 8, respectively, or SEQ ID Nos.: 7 and 9, respectively, at the following fixed dose ratios: 80-300 mg of anti-PD-1 or anti-PD-L1 antibody to 1-1000 mg of anti-GITR antibody; 80-300 mg of anti-PD-1 or anti-PD-L1 antibody to 1-100 mg of anti-GITR antibody; 80-300 mg of anti-PD-1 or anti-PD-L1 antibody to 10-100 mg of anti-GITR antibody; 80-300 mg of anti-PD-1 or anti-PD-L1 antibody to 10-300 mg of anti-GITR antibody or 80-300 mg of anti-PD-1 or anti-PD-L1 antibody to 100-300 mg of anti-GITR antibody. In exemplary embodiments, nivolumab is co-formulated with an anti-GITR antibody, wherein the dose of nivolumab is about 80 mg or about 240 mg. A fixed dose combination may be administered as an intravenous infusion over, e.g., about 30, about 30-60, about 60 or about 60-90 minutes every about 1, about 2, about 3 or about 4 weeks.

In certain embodiments, about 3 mg/kg anti-PD-1 antibody, e.g., nivolumab, may be administered together, e.g., as a fixed dose combination, with about 0.1-10 mg/kg, about 0.1-5 mg/kg, about 0.5-10 mg/kg, about 0.5-5 mg/kg, about 0.5-2 mg/kg, about 1-2 mg/kg or about 2-5 mg/kg anti-GITR antibody, e.g., TRX518, MK4166, or an antibody comprising the heavy and light chains or variable regions or CDRs described herein, e.g., as an intravenous infusion over, e.g., about 30, about 30-60, about 60 or about 60-90 minutes every about 1, about 2, about 3 or about 4 weeks. In certain embodiments, about 2 mg/kg anti-PD-1 antibody, e.g., nivolumab or MK-3475, is administered together, e.g., as a fixed dose combination, with about 0.1-10 mg/kg, about 0.1-5 mg/kg, about 0.5-10 mg/kg, about 0.5-5 mg/kg, about 0.5-2 mg/kg, about 1-2 mg/kg or about 2-5 mg/kg anti-GITR antibody, e.g., MK4166 or an antibody comprising the heavy and light chains or variable regions or CDRs described herein, e.g., as an intravenous infusion over, e.g., about 30, about 30-60 or about 60 minutes every about 1, about 2, about 3 or about 4 weeks. The amount of antibodies in mg/kg can be calculated to determine the weight (mg) or the concentration (mg/ml) of the antibodies required for a fixed dosing ratio formulation. In certain embodiments, an anti-PD-1 antibody and an anti-GITR antibody are provided as a lyophilized composition, e.g., in a vial or a dual chamber syringe. A lyophilized composition can comprise, e.g., about 50 mg of an anti-PD-1 or anti-PD-L1 antibody, e.g., nivolumab, MK3475 or atezolizumab and about 5-250 mg, about 10-250, about 30-100 mg, about 30-70 mg or about 50 mg of an anti-GITR antibody, e.g., TRX-518, MK4166 or an antibody comprising the heavy and light chains or variable regions or CDRs described herein.

Additional Antibodies

In some embodiments, the second antibody to be combined with the first antibody is an anti-TGFβ antibody, as disclosed in Int'l Publ. No. WO/2009/073533. In some embodiments, the second antibody is an anti-IL-10 antibody, as disclosed in Int'l Publ. No. WO/2009/073533. In some other embodiments, the second antibody is an anti-B7-H4 antibody, as disclosed in Int'l Publ. No. WO/2009/073533. In certain embodiments, the second antibody is an anti-Fas ligand antibody, as disclosed in Int'l Publ. No. WO/2009/073533. In some embodiments, the second antibody is an anti-CXCR4 antibody, as disclosed in U.S. Publ. No. 2014/0322208 (e.g., Ulocuplumab (BMS-936564)). In some embodiments is the second antibody is an anti-mesothelin antibody, as disclosed in U.S. Pat. No. 8,399,623. In some embodiments, the second antibody is an anti-HER2 antibody, for example, Herceptin (U.S. Pat. No. 5,821,337), trastuzumab, or ado-trastuzumab emtansine (Kadcyla, e.g., WO/2001/000244). In embodiments, the second antibody to be combined with the first antibody is an anti-CD27 antibody. In embodiments, the anti-CD-27 antibody is Varlilumab (also known as "CDX-1127" and "1F5"), which is a human IgG1 antibody that is an agonist for human CD27, as disclosed in, for example, U.S. Pat. No. 9,169,325. In some embodiments, the second antibody to be combined with the first antibody is an anti-CD73 antibody. In certain embodiments, the anti-CD73 antibody is CD73.4.IgG2C219S.IgG1.1f.

Formulations, Pharmaceutical Compositions and Dosages

In the formulation of the present invention, a first antibody and a second antibody are formulated in a single composition of the present invention e.g., a pharmaceutical composition containing the first antibody and the second antibody and a pharmaceutically acceptable carrier. In one embodiment, the first antibody is an anti-PD-1 antibody. In another embodiment, the first antibody is an anti-PD-L1 antibody. An anti-PD-L1 antibody can be used in place of an anti-PD-1 antibody in any composition or method described herein.

As used herein, a "pharmaceutically acceptable carrier" includes any and all solvents, dispersion media, coatings, antibacterial and antifungal agents, isotonic and absorption delaying agents, and the like that are physiologically compatible. In certain embodiments, the carrier for a composition containing an antibody is suitable for intravenous, intramuscular, subcutaneous, parenteral, spinal or epidermal administration (e.g., by injection or infusion). A pharmaceutical composition of the invention can include one or more pharmaceutically acceptable salts, anti-oxidant, aqueous and non-aqueous carriers, and/or adjuvants such as preservatives, wetting agents, emulsifying agents and dispersing agents.

In one embodiment, the composition comprising the first antibody and the second antibody is provided in a single-use vial. In another embodiment, the composition comprising the first antibody and the second antibody is provided in a multi-use vial.

In other embodiments, the first antibody (e.g., an anti-PD-1 antibody or anti-PD-L1 antibody) is formulated with any known second antibody. In some embodiments, the second antibody is an anti-CTLA4 antibody. In certain embodiments, the anti-CTLA4 antibody is tremelimumab or ipilimumab. In some embodiments, the second antibody is an anti-CD137 antibody. In some embodiments, the anti-CD137 antibody is urelumab. In some embodiments, the second antibody is an anti-LAG3 antibody. In some embodiments, the anti-LAG3 antibody is 25F7. In some embodiments, the second antibody is an anti-GITR antibody. In some embodiments, the anti-GITR antibody is MK4166, TRX518, an antibody comprising the CDRs, variable chains or heavy and light chains of the anti-GITR antibodies that are described in PCT/US2015/033991 (e.g., those of 28F3, 18E10 or 19D3) or any other anti-GITR antibody described herein. In some embodiments, the second antibody is an anti-KIR antibody. In some embodiments, the anti-KIR antibody is 1-7F9 or lirilumab. In some embodiments, the second antibody is an anti-TGFβ antibody, an anti-IL-10 antibody, an anti-B7-H4 antibody, an anti-Fas ligand antibody, an anti-CXCR4 antibody, an anti-mesothelin antibody, an anti-CD27 antibody, an anti-CD73 antibody or any combination thereof.

In some embodiments, the first antibody and the second antibody are present in the composition at a fixed dose (i.e. a fixed ratio). In other embodiments, this fixed dose is between at least about 1:200 to at least about 200:1, at least about 1:150 to at least about 150:1, at least about 1:100 to at least about 100:1, at least about 1:75 to at least about 75:1, at least about 1:50 to at least about 50:1, at least about 1:25 to at least about 25:1, at least about 1:10 to at least about 10:1, at least about 1:5 to at least about 5:1, at least about 1:4 to at least about 4:1, at least about 1:3 to at least about 3:1, or at least about 1:2 to at least about 2:1 mg anti-PD-1 antibody (or anti-PD-L1 antibody) to mg second antibody. In some embodiments, the fixed dose is at least about 1:1, about 1:2, about 1:3, about 1:4, about 1:5, about 1:6, about 1:7, about 1:8, about 1:9, about 1:10, about 1:15, about 1:20, about 1:30, about 1:40, about 1:50, about 1:60, about 1:70, about 1:80, about 1:90, about 1:100, about 1:120, about 1:140, about 1:160, about 1:180, or about 1:200 anti-PD-1 antibody (or anti-PD-L1 antibody) to second antibody. In some embodiments, the fixed dose is at least about 2:1, about 3:1, about 4:1, about 5:1, about 6:1, about 7:1, about 8:1, about 9:1, about 10:1, about 15:1, about 20:1, about 30:1, about 40:1, about 50:1, about 60:1, about 70:1, about 80:1, about 90:1, about 100:1, about 120:1, about 140:1, about 160:1, about 180:1, or about 200:1 mg first antibody to mg second antibody.

In other embodiments, the composition comprises a first antibody and a second antibody at a ratio (e.g., from 200:1 to 1:200, 100:1 to 1:100, 20-1:1 to 1:1-20, or any ratio disclosed herein), wherein the composition has one or more characteristics selected from the group consisting of: (i) the aggregation in the composition is comparable to the aggregation in a reference composition (i.e., a composition comprising either the first antibody or the second antibody) after 6-months storage at 2° C. to 8° C.; (ii) the fragmentation in the composition is comparable to the aggregation in a reference composition (i.e., a composition comprising either the first antibody or the second antibody) after 6-months storage at 2° C. to 8° C.; (iii) the deamidation of the first antibody or the second antibody in the composition is comparable to the deamidation of the antibody in a reference composition (i.e., a composition comprising either the first antibody or the second antibody) after 6-months storage at 2° C. to 8° C.; (iv) the level of particulate matter in the composition is comparable to the level of particular matter in a reference composition (i.e., a composition comprising either the first antibody or the second antibody) after 6-months storage at 2° C. to 8° C.; and (v) any combination thereof.

In yet other embodiments, the composition comprises a first antibody and a second antibody at a ratio (e.g., from 200:1 to 1:200, 100:1 to 1:100, 20-1:1 to 1:1-20, or any ratio disclosed herein, wherein the composition has one or more characteristics selected from the group consisting of: (i) the aggregation in the composition is comparable to the aggregation in a reference composition (i.e., a composition comprising either the first antibody or the second antibody) after 6-months storage at 25° C.; (ii) the fragmentation in the composition is comparable to the aggregation in a reference composition (i.e., a composition comprising either the first antibody or the second antibody) after 6-months storage at 25° C.; (iii) the deamidation of the first antibody or the second antibody in the composition are comparable to the deamidation of the antibody in a reference composition (i.e., a composition comprising either the first antibody or the second antibody) after 6-months storage at 25° C.; (iv) the level of particulate matter in the composition is comparable to the level of particular matter in a reference composition (i.e., a composition comprising either the first antibody or the second antibody) after 6-months storage at 25° C.; and (v) any combination thereof.

In some embodiments, the aggregation of a composition is measured by a level of high molecular weight (HMW) species in the composition, which can be detected by size exclusion high-performance liquid chromatography (SE-HPLC). In some embodiments, the fragmentation of a composition is measured by a level of low molecular weight (LMW) species in the composition, which is detected by SE-HPLC. In some embodiments, the deamidation of a composition is measured by a level of acidic charge variants in the composition, which is detected by cation exchange chromatography (CEX) or imaged capillary isoelectric focusing (iCIEF).

In some embodiments, the amount of the anti-PD-1 antibody in the composition is at least about 60 mg, about 80 mg, about 100 mg, about 120 mg, about 140, about 160 mg, about 180 mg, about 200 mg, about 220 mg, about 240 mg, about 260 mg, about 280 mg, or about 300 mg. In some embodiments, the amount of the anti-PD-1 antibody in the composition is at least about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, or about 500 mg. In some embodiments, the amount of the anti-PD-1 antibody in the composition is between about 60 mg and about 300 mg, between about 60 mg and about 100 mg, between about 100 mg and about 200 mg, or between about 200 mg and about 300 mg. In some embodiments, the amount of the anti-PD-1 antibody in the composition is between about 300 mg and about 500 mg, between about 300 mg and about 450 mg, between about 300 mg and about 400 mg, between about 300 mg and about 350 mg, between about 350 mg and about 500 mg, between about 400 mg and about 500 mg, or between about 450 mg and about 500 mg. In some embodiments, the amount of the anti-PD-1 antibody in the composition is at least about 80 mg, about 160 mg, or about 240 mg. In some embodiments, the amount of the anti-PD-1 antibody in the composition is at least about 240 mg or at least about 80 mg. In some embodiments, the amount of the anti-PD-1 antibody in the composition is at least about 360 mg or at least about 480 mg. In some embodiments, the amount of the anti-PD-1 antibody in the composition is a least about 0.5 mg/kg, at least about 1 mg/kg, at least about 2 mg/kg, at least about 3 mg/kg or at least about 5 mg/kg. In some embodiments, the amount of anti-PD-1 antibody in the composition is between about 0.5 mg/kg and about 5 mg/kg, between about 0.5 mg/kg and about 5 mg/kg, between about 0.5 mg/kg and about 3 mg/kg or between about 0.5 mg/kg and about 2 mg/kg. In some embodiments, the amount of the anti-PD-1 antibody in the composition is at least about 1 mg/kg. In some embodiments, the anti-PD-1 antibody is nivolumab or pembrolizumab.

In some embodiments, the anti-PD-1 antibody is pembrolizumab and the amount of anti-PD-1 antibody in the composition is at least about 50 mg, at least about 75 mg, at least about 100 mg, at least about 150 mg, at least about 200 mg, at least about 250 mg, or at least about 300 mg. In some embodiments, the amount of anti-PD-1 antibody in the composition is at least about 100 mg or at least about 200 mg. In some embodiments, the amount of the anti-PD-1 antibody in the composition is at least about 300 mg, at least about 350 mg, at least about 400 mg, at least about 450 mg, or at least about 500 mg. In some embodiments, the anti-PD-1 antibody is pembrolizumab and the amount of anti-PD-1 antibody used to treat a disease or condition can be a weight based dose, e.g., at least about 0.5 mg/kg, at least about 1 mg/kg, at least about 2 mg/kg, at least about 3 mg/kg, at least about 5 mg/kg, at least about 10 mg/kg, at least about 15 mg/kg or at least about 20 mg/kg. In some embodiments, the amount of anti-PD-1 antibody that can be used to treat a disease or condition is a weight based dose, e.g., at least about 1 mg/kg, at least about 2 mg/kg, or at least about 10 mg/kg. In some embodiments, the second antibody is an anti-CTLA4 antibody, and the fixed dose is about 1:1, about 3:1 or about 1:3 mg anti-PD-1 antibody to mg anti-CTLA4 antibody. In some embodiments, the amount of the anti-CTLA4 antibody in the composition is at least about 60 mg, about 80 mg, about 100 mg, about 120 mg, about 140, about 160 mg, about 180 mg, about 200 mg, about 220 mg, about 240 mg, about 260 mg, about 280 mg, or about 300 mg. In some embodiments, the amount of the anti-CTLA4 antibody in the composition is between about 60 mg and about 300 mg, between about 60 mg and about 100 mg, between about 100 mg and about 200 mg, or between about 200 mg and about 300 mg. In some embodiments, the amount of the anti-CTLA4 antibody in the composition is at least about 80 mg, about 160 mg, or about 240 mg. In some embodiments, the amount of the anti-CTLA4 antibody in the composition is at least about 240 mg. In some embodiments, the amount of the anti-CTLA4 antibody in the composition is at least about 1 mg/kg, at least about 2 mg/kg, at least about 3 mg/kg or at least about 5 mg/kg. In some embodiments, the amount of the anti-CTLA4 antibody in the composition is used as a weight based dose, e.g., between about 1 mg/kg and about 10 mg/kg, between about 1 mg/kg and about 5 mg/kg or between about 2 mg/kg and about 5 mg/kg. In some embodiments, the amount of the anti-CTLA4 antibody in the composition is a least about 3 mg/kg. In some embodiments, (i) the X amount is about 240 mg and the Y amount is about 80 mg, (ii) the X amount is about 80 mg and the Y amount is about 80 mg; (iii) the X amount is about 160 mg and the Y amount is about 160 mg; (iv) the X amount is about 240 mg and the Y amount is about 240 mg; or (v) the X amount is about 80 mg and the Y amount is about 240 mg.

In some embodiments, the second antibody is an anti-KIR antibody and the fixed dose is about 30:1, about 10:1, about 3:1, about 1:1, about 1:2, or about 3:10 mg anti-PD-1 antibody to mg anti-KIR antibody.

In some embodiments, the second antibody is an anti-LAG3 antibody, and the fixed dose is about 80:3, about 80:1, about 12:1, about 3:1, or about 1:1 mg anti-PD-1 antibody to mg anti-LAG3 antibody. In some embodiments, the amount of anti-LAG3 antibody in the composition is at least about 60 mg, about 80 mg, about 100 mg, about 120 mg, about 140, about 160 mg, about 180 mg, about 200 mg, about 220 mg, about 240 mg, about 260 mg, about 280 mg, about 300 mg, or about 350 mg. In some embodiments, the amount of anti-LAG3 antibody in the composition is between about 60 and about 350 mg, between about 60 and about 300 mg, between about 100 and about 300 mg, or between about 150 and about 250 mg. In some embodiments, the amount of anti-LAG3 antibody is at least about 240 mg.

In some embodiments the second antibody is an anti-CD137 antibody and the fixed dose is about 1:1, about 1:2, about 1:3, about 1:4, about 1:5, about 1:10, about 10:1, about 5:1, about 4:1 or about 2:1 mg anti-PD-1 antibody to mg anti-CD137 antibody. In some embodiments, the amount of the anti-CD137 antibody in the composition is at least about 1 mg, at least about 2 mg, at least about 3 mg, at least about 4 mg, at least about 5 mg, at least about 6 mg, at least about 7 mg, at least about 8 mg, at least about 9 mg, at least about 10 mg, at least about 12 mg, at least about 15 mg, or at least about 20 mg. In some embodiments, the amount of the anti-CD137 antibody in the composition is between about 1 mg and about 20 mg, between about 1 mg and about 15 mg, between about 5 mg and about 12 mg or between about 5 mg and about 10 mg. In some embodiments, the amount of the anti-CD137 antibody in the composition is a least about 8 mg.

In some embodiments the second antibody is an anti-CD73 antibody, and the fixed dose is about 1:1, about 1:2, about 1:3, about 1:4, about 1:5, about 1:10, about 10:1, about 5:1, about 4:1 or about 2:1 mg anti-PD-1 antibody to mg anti-CD73 antibody. In some embodiments, the amount of the anti-CD73 antibody in the composition is from about 100 mg to about 2000 mg or from about 150 mg to about 1600 mg. In some embodiments, the amount of the anti-CD73 antibody in the composition is at least about 100 mg, 150 mg, 200 mg, 300 mg, 500 mg, 600 mg, 800 mg, 1000 mg, 1200 mg, or 1600 mg.

In certain embodiments, the anti-CD73 antibody CD73.4.IgG2C219S.IgG1.1f and nivolumab are administered as fixed doses at one of following combination doses: 50 mg of anti-CD73 antibody and 240 mg of nivolumab every two weeks; 50 mg of anti-CD73 antibody and 360 mg of nivolumab every three weeks; 150 mg of anti-CD73 antibody and 240 mg of nivolumab every two weeks; 150 mg of anti-CD73 antibody and 360 mg of nivolumab every three weeks; 300 mg of anti-CD73 antibody and 240 mg of nivolumab every two weeks; 300 mg of anti-CD73 antibody and 360 mg of nivolumab every three weeks; 600 mg of anti-CD73 antibody and 240 mg of nivolumab every two weeks; 600 mg of anti-CD73 antibody and 360 mg of nivolumab every three weeks; 1200 mg of anti-CD73 antibody and 240 mg of nivolumab every two weeks; 1200 mg of anti-CD73 antibody and 360 mg of nivolumab every three weeks; 1600 mg of anti-CD73 antibody and 240 mg of nivolumab every two weeks; 1600 mg of anti-CD73 antibody and 360 mg of nivolumab every three weeks; 2000 mg of anti-CD73 antibody and 240 mg of nivolumab every two weeks; 2000 mg of anti-CD73 antibody and 360 mg of nivolumab every three weeks.

In some embodiments, the PD-1 antibody and the second antibody are combined using the current formulations of the two antibodies (for example, 2 mls of an anti-PD-1 antibody in a citrate-based buffer are combined with 2 mls of an anti-CTLA4 antibody in a Tris-based buffer with no buffer exchange).

In some embodiments, the composition comprises one or more additional components selected from the group consisting of: a bulking agent, a stabilizing agent, a chelating agent, a surfactant, a buffering agent, and any combination thereof. In some embodiments, the buffering agent contains a citrate buffer, a Tris buffer, a Tris-Cl buffer, a histidine buffer, a TAE buffer, a HEPES buffer, a TBE buffer, a sodium phosphate buffer, a MES buffer, an ammonium sulfate buffer, a potassium phosphate buffer, a potassium thiocyanate buffer, a succinate buffer, a tartrate buffer, a DIPSO buffer, a HEPPSO buffer, a POPSO buffer, a PIPES buffer, a PBS buffer, a MOPS buffer, an acetate buffer, a phosphate buffer, a cacodylate buffer, a glycine buffer, a sulfate buffer, an imidazole buffer, a guanidine hydrochloride buffer, a phosphate-citrate buffer, a borate buffer, a malonate buffer, a 3-picoline buffer, a 2-picoline buffer, a 4-picoline buffer, a 3,5-lutidine buffer, a 3,4-lutidine buffer, a 2,4-lutidine buffer, a Aces, a diethylmalonate buffer, a N-methylimidazole buffer, a 1,2-dimethylimidazole buffer, a TAPS buffer, a bis-Tris buffer, a L-arginine buffer, a lactate buffer, a glycolate buffer.

In some embodiments, the PD-1 antibody and the second antibody are formulated in a buffer that is based on the buffer conditions of one of the two individual antibody formulations. In some embodiments, the buffer conditions used are those of the anti-PD-1 antibody. In some embodiments, the anti-PD-1 antibody is nivolumab, and the two antibodies are formulated in the citrate-based buffer system of nivolumab. In some embodiments, the buffer is a citrate buffer.

In some embodiments, the PD-1 antibody and the second antibody are formulated in buffer conditions that are different from the buffer conditions of either of the two antibodies on its own. In some embodiments, the buffer is a citrate-based buffer. In some embodiments, the concentration of citrate in the buffer is at least about 5 mM, about 10 mM, about 15 mM, about 20 mM, about 25 mM, about 30 mM, about 35 mM, about 40 mM, or about 50 mM. In some embodiments, the concentration of citrate is between about 5 mM and about 50 mM, in some embodiments, between about 5 mM and about 40 mM, between about 5 mM and about 30 mM, between about 5 mM and about 20 mM, between about 5 mM and about 15 mM, between about 10 mM and about 30 mM, or between about 15 mM and about 25 mM. In some embodiments, the concentration of citrate is about 10 mM. In some embodiments, the concentration of citrate is about 20 mM.

In some embodiments, the buffer used is a Tris-based buffer. In some embodiments, the Tris buffer is a Tris-Cl buffer. In some embodiments, the concentration of Tris-Cl in the buffer is at least about 5 mM, about 10 mM, about 15 mM, about 20 mM, about 25 mM, about 30 mM, about 35 mM, about 40 mM, or about 50 mM. In some embodiments, the concentration of Tris-Cl is between about 5 mM and about 50 mM, between about 10 mM and about 50 mM, between about 10 mM and about 40 mM, between about 10 mM and about 30 mM or between about 15 mM and about 25 mM. In some embodiments, the concentration of Tris-Cl is about 20 mM.

In some embodiments, the buffer used is a histidine-based buffer. In some embodiments, the concentration of histidine is at least about 5 mM, about 10 mM, about 15 mM, about 20 mM, about 25 mM, about 30 mM, about 35 mM, about 40 mM, or about 50 mM. In some embodiments, the concentration of histidine is between about 5 mM and about 50 mM, between about 5 mM and about 40 mM, between about 5 mM and about 30 mM, between about 5 mM and about 25 mM or between about 10 mM and about 15 mM. In some embodiments, the concentration of histidine is about 20 mM.

In some embodiments, the buffer used is a Tris-citrate buffer. In some embodiments, the concentration of Tris-Cl is at least about 5 mM, about 10 mM, about 15 mM, about 20 mM, about 25 mM, about 30 mM, about 35 mM, about 40 mM, or about 50 mM and the concentration of citrate is at least about 2 mM, about 5 mM, about 10 mM, about 15 mM, about 20 mM, about 25 mM, about 30 mM, about 35 mM, about 40 mM, or about 50 mM. In some embodiments, the concentration of Tris-Cl is between about 5 and about 20 mM, between about 5 and about 15 mM, or between about 10 and about 15 mM and the concentration of citrate is between about 1 mM and about 15 mM, between about 1 mM and about 10 mM, or between about 5 mM and about 10 mM. In some embodiments, the concentration of Tris-Cl is about 13.3 mM and the concentration of citrate is about 6.7 mM.

In some embodiments, the pH of the composition is at least about 5, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, or about 8.0. In some embodiments, the pH of the composition is between about 5.0 and about 8.0, between about 5.5 and about 6.5, between about 6.0 and about 7.0, or between about 6.5 and about 7.5. In some embodiments, the pH is about 6.0, In other embodiments the pH is about 7.0. In other embodiments, the pH is about 6.2. In other embodiments, the pH is about 6.5. In other embodiments, the pH is about 6.6. In other embodiments, the pH is about 5.5.

In some embodiments, the composition of the invention further comprises a bulking agent. A bulking agent can be selected from the group consisting of NaCl, mannitol, glycine, alanine, and any combination thereof. In other embodiments, the composition of the invention comprises a stabilizing agent. The stabilizing agent can be selected from the group consisting of sucrose, trehalose, raffinose, arginine; or any combination thereof. In other embodiments, the composition of the invention comprises a surfactant. The surfactant can be selected from the group consisting of polysorbate 80 (PS80), polysorbate 20 (PS20), and any combination thereof. In certain embodiments, the composition further comprises a chelating agent. The chelating agent can be selected from the group consisting of diethylenetriaminepentaacetic acid (DTPA), ethylenediaminetetraacetic acid, nitrilotriacetic acid, and any combination thereof.

In one embodiment, the composition comprises NaCl, mannitol, pentetic acid (DTPA), sucrose, PS80, and any combination thereof. In another embodiment, the composition comprises NaCl at a concentration of at least about 5 mM, at least about 10 mM, at least about 15 mM, at least about 20 mM, at least about 25 mM, at least about 30 mM, at least about 35 mM, at least about 40 mM, at least about 45 mM, at least about 50 mM, at least about 60 mM, at least about 70 mM, at least about 75 mM, at least about 80 mM, at least about 90 mM, at least about 100 mM, at least about 110 mM, at least about 120 mM, at least about 130 mM, at least about 140 mM, at least about 150 mM, at least about 175 mM, at least about 200 mM, at least about 225 mM, at least about 250 mM, at least about 275 mM, at least about 300 mM, at least about 350 mM, at least about 400 mM, at least about 450 mM or at least about 450 mM. In other embodiments, the composition comprises between about 10 and about 200 mM NaCl, between about 25 and about 150 mM NaCl, between about 40 and about 125 mM NaCl, between about 25 and about 75 mM NaCl, between about 50 and about 100 mM NaCl or between about 75 and 125 mM NaCl. In some embodiments, the composition comprises about 100 mM NaCl. In certain embodiments, the composition comprises about 50 mM NaCl. In other embodiments, the composition comprises about 83.3 mM NaCl. In yet other embodiments, the composition comprises about 96.15 mM NaCl. In a particular embodiment, the composition comprises about 78.57 mM NaCl.

In certain embodiments, the composition comprises mannitol (% w/v) USP at a concentration of at least about 0.25%, at least about 0.5%, at least about 0.75%, at least about 1%, at least about 1.5%, at least about 2%, at least about 2.5%, at least about 3%, at least about 3.5%, at least about 4%, at least about 4.5%, at least about 5%, at least about 7.5% or at least about 10%. In other embodiments, the composition comprises between about 0.5% and about 5% mannitol, between about 0.5% and about 4% mannitol, between about 0.5% and about 1.5% mannitol, between about 1% and about 2% mannitol, or between about 2.5% and about 3.5% mannitol. In yet other embodiments, the composition comprises about 1% mannitol. In still other embodiments, the composition comprises about 3.0% mannitol. In some embodiments, the composition comprises about 1.67% mannitol. In certain embodiments, the composition comprises about 1.15% mannitol. In a particular embodiment, the composition comprises about 1.86% mannitol.

In other embodiments, the composition comprises pentetic acid (DTPA), USP at a concentration of at least about 5 µM, at least about 10 µM, at least about 15 µM, at least about 20 µM, at least about 25 µM, at least about 30 µM, at least about 40 µM, at least about 50 µM, at least about 60 µM, at least about 70 µM, at least about 75 µM, at least about 80 µM, at least about 90 µM, at least about 100 µM, at least about 110 µM, at least about 120 µM, at least about 130 µM, at least about 140 µM, at least about 150 µM, at least about 175 µM, or at least about 200 µM. In some embodiments, the composition comprises between about 10 µM and about 200 µM DTPA, between about 10 µM and about 150 µM DTPA, between about 10 µM and about 100 µM DTPA, between about 10 µM and about 30 µM DTPA, between about 50 µM and about 100 µM DTPA, or between about 75 µM and about 125 µM DTPA. In other embodiments, the composition comprises DTPA at about 100 µM. In certain embodiments, the composition comprises DTPA at about 20 µM. In yet other embodiments, the composition comprises DTPA at about 73.3 µM. In a particular embodiment, the composition comprises DTPA at about 50 µM. In a specific embodiments, the composition comprises DTPA at about 93.85 µM. In certain embodiments, the composition comprises DTPA at about 65.71 µM.

In some embodiments, the composition comprises polysorbate 80, NF (PS80) (% w/v) at a concentration of at least about 0.005%, at least about 0.01%, at least about 0.015%, at least about 0.02%, at least about 0.03%, at least about 0.04%, at least about 0.05%, at least about 0.06%, at least about 0.07%, at least about 0.08%, at least about 0.09%, or at least about 0.1%. In other embodiments, the composition comprises between about 0.005% and about 0.1% PS80, between about 0.005% and about 0.02% PS80, between about 0.005% and about 0.05% PS80, between about 0.01% and about 0.02% PS80, between about 0.02% and about 0.1% PS80 or between about 0.01% and about 0.03% PS80. In still other embodiments, the composition comprises PS80 at a concentration of about 0.01%. In yet other embodiments, the composition comprises PS80 at a concentration of about 0.04%. In some embodiments, the composition comprises PS80 at a concentration of about 0.013%. In a particular embodiment, the composition comprises PS80 at a concentration of about 0.05%. In some embodiments, the composition comprises PS80 at a concentration of about 0.02%. In other embodiments, the composition comprises PS80 at a concentration of about 0.012%. In a specific embodiment, the composition comprises PS80 at a concentration of about 0.23%.

In certain embodiments, the composition comprises sucrose (% w/v) at a concentration of at least about 1%, at least about 2%, at least about 3%, at least about 4%, at least about 4.5%, at least about 5%, at least about 5.5%, at least about 6%, at least about 6.5%, at least about 7%, at least about 7.5%, at least about 8%, at least about 8.5%, at least about 9%, at least about 9.5%, at least about 10%, at least about 12% or at least about 15% sucrose. In other embodiments, the composition comprises between about 1% and about 10%, between about 2% and about 10%, between about 5% and about 10%, between about 5% and about 7%, or between about 7.5% and about 10% sucrose. In yet other embodiments, the composition comprises about 6% sucrose. In still other embodiments, the composition comprises about 8.5% sucrose. In other embodiments, the composition comprises about 8.0% sucrose.

In certain embodiments, the composition comprises nivolumab and ipilimumab in a Tris-citrate buffer. In some embodiments the composition comprises a 1:1 ratio of nivolumab to ipilimumab in a buffer comprising about 13.3 mM Tris (or 13.3 mM Tris±10%, 20%, 30%, 40%, or 50%), about 6.7 mM citrate, (or 6.7 mM citrate±10%, 20%, 30%, 40%, or 50%), about 1.67% mannitol (1.67% mannitol±10%, 20%, 30%, 40%, or 50%), about 83.3 mM NaCl (or 83.3 mM NaCl±10%, 20%, 30%, 40%, or 50%), about 73.3 µM DTPA (or 73.3 µM DTPA±10%, 20%, 30%, 40%, or 50%) and about 0.013% PS80 (or 0.013% PS80±10%, 20%, 30%, 40%, or 50%) at a pH of about 6.2. In some embodiments the composition comprises a 3:1 ratio of nivolumab to ipilimumab in a Tris-citrate buffer comprising about 1.15% mannitol (or 1.15% mannitol±10%, 20%, 30%, 40%, or 50%), about 96.15 mM NaCl (or 96.15 mM NaCl±10%, 20%, 30%, 40%, or 50%), about 93.85 µM DTPA (or 93.85 µM DTPA±10%, 20%, 30%, 40%, or 50%) and about 0.012% PS80 (or 0.012% PS80±10%, 20%, 30%, 40%, or 50%) at a pH of about 6.6. In some embodiments the composition comprises a 1:3 ratio of nivolumab to ipilimumab in a Tris-citrate buffer comprising about 1.86% mannitol (or 1.86% mannitol±10%, 20%, 30%, 40%, or 50%), about 78.57 mM NaCl (or 78.57 mM NaCl±10%, 20%, 30%, 40%, or 50%), about 65.71 µM DTPA (or 65.71 µM DTPA±10%, 20%, 30%, 40%, or 50%) and about 0.023% PS80 (or 0.023% PS80±10%, 20%, 30%, 40%, or 50%) at a pH of about 6.0.

In other embodiments, the composition comprises nivolumab and ipilimumab in a histidine buffer. In some embodiments the composition comprises a 3:1 ratio of nivolumab to ipilimumab in a 20 mM histidine buffer (or 20 mM histidine buffer±10%, 20%, 30%, 40%, or 50%) comprising about 50 mM NaCl (or 50 mM NaCl±10%, 20%, 30%, 40%, or 50%), about 50 µM DTPA (or 50 µM DTPA±10%, 20%, 30%, 40%, or 50%), about 6% sucrose (or 6% sucrose±10%, 20%, 30%, 40%, or 50%), and about 0.05% PS80 (or 0.05% PS80±10%, 20%, 30%, 40%, or 50%) at about pH 6. In some embodiments the composition comprises a 3:1 ratio of nivolumab to ipilimumab in a about 20 mM histidine buffer comprising about 50 mM NaCl (or 50 mM NaCl±10%, 20%, 30%, 40%, or 50%), about 50 µM DTPA (or 50 µM DTPA±10%, 20%, 30%, 40%, or 50%), about 6% sucrose (or 6% sucrose±10%, 20%, 30%, 40%, or 50%), and about 0.05% PS80 (or 0.05% PS80±10%, 20%, 30%, 40%, or 50%) at about pH 7. In some embodiments the composition comprises a 3:1 ratio of nivolumab to ipilimumab in an about 20 mM histidine buffer (or 20 mM histidine buffer±10%, 20%, 30%, 40%, or 50%) comprising about 50 µM DTPA (or 50 µM DTPA 10%, 20%, 30%, 40%, or 50%), about 8.5% sucrose (or 8.5% sucrose±10%, 20%, 30%, 40%, or 50%), and about 0.05% PS80 (or 0.05% PS80±10%, 20%, 30%, 40%, or 50%) at about pH 6. In some embodiments, the composition comprises a 1:1, 3:1, or 1:3 ratio of nivolumab to ipilimumab in a histidine buffer (20 mM±10%, 20%, 30%, 40%, or 50%) comprising 5 µM DTPA (or 50 µM DTPA±10%, 20%, 30%, 40%, or 50%), 0.05% PS80 (or 0.05% PS80±10%, 20%, 30%, 40%, or 50%) and 8.0% sucrose (or 8.0% sucrose±10%, 20%, 30%, 40%, or 50%) at pH 5.5, 6.0 or 6.5. In one embodiment, the composition comprises nivolumab and ipilimumab in a citrate buffer. In another embodiment, the composition comprises a 3:1 ratio of nivolumab to ipilimumab in an about 20 mM citrate buffer (or 20 mM citrate buffer±10%, 20%, 30%, 40%, or 50%) comprising about 50 mM NaCl (or 50 mM NaCl±10%, 20%, 30%, 40%, or 50%), about 50 µM DTPA (or 50 µM DTPA±10%, 20%, 30%, 40%, or 50%), about 6% sucrose (or 6% sucrose±10%, 20%, 30%, 40%, or 50%), and about 0.05% PS80 (or 0.05% PS80±10%, 20%, 30%, 40%, or 50%) at about pH 6. In other embodiments, the composition comprises a 3:1 ratio of nivolumab to ipilimumab in an about 20 mM citrate buffer (or 20 mM citrate buffer±10%, 20%, 30%, 40%, or 50%) comprising about 50 mM NaCl (or 50 mM NaCl±10%, 20%, 30%, 40%, or 50%), about 20 µM DTPA (or 20 µM DTPA±10%, 20%, 30%, 40%, or 50%), about 3% mannitol (or 3% mannitol±10%, 20%, 30%, 40%, or 50%), and about 0.04% PS80 (or 0.04% PS80±10%, 20%, 30%, 40%, or 50%) at about pH 6. In still other embodiments, the composition comprises a 1:1 ratio of nivolumab to ipilimumab in an about 20 mM citrate buffer (or 20 mM citrate buffer±10%, 20%, 30%, 40%, or 50%) comprising about 50 mM NaCl (or 50 mM NaCl±10%, 20%, 30%, 40%, or 50%), about 100 µM DTPA (or 100 µM DTPA±10%, 20%, 30%, 40%, or 50%), about 3% mannitol (or 3% mannitol 10%, 20%, 30%, 40%, or 50%), and about 0.02% PS80 (or 0.02% PS80±10%, 20%, 30%, 40%, or 50%) at about pH 6. In certain embodiments, the composition comprises a 1:1 ratio of nivolumab to ipilimumab in an about 20 mM citrate buffer (or 20 mM citrate buffer±10%, 20%, 30%, 40%, or 50%) comprising about 50 mM NaCl (or 50 mM NaCl±10%, 20%, 30%, 40%, or 50%), about 100 µM DTPA (or 100 µM DTPA±10%, 20%, 30%, 40%, or 50%), about 3% mannitol (or 3% mannitol±10%, 20%, 30%, 40%, or 50%), and about 0.02% PS80 (or 0.02% PS80±10%, 20%, 30%, 40%, or 50%) at about pH 6.5. In some embodiments, the composition comprises a 1:1 ratio of nivolumab to ipilimumab in an about 20 mM citrate buffer (or 20 mM citrate buffer±10%, 20%, 30%, 40%, or 50%) comprising about 100 mM NaCl (or 100 mM NaCl±10%, 20%, 30%, 40%, or 50%), about 100 µM DTPA (or 100 µM DTPA±10%, 20%, 30%, 40%, or 50%), about 1.0% mannitol (or 1.0% mannitol±10%, 20%, 30%, 40%, or 50%), and about 0.02% PS80 (or 0.02% PS80±10%, 20%, 30%, 40%, or 50%) at about pH 6.5. In yet other embodiments, the composition comprises a 1:1 ratio of nivolumab to ipilimumab in an about 20 mM citrate buffer (or 20 mM citrate buffer±10%, 20%, 30%, 40%, or 50%) comprising about 50 mM NaCl (or 50 mM NaCl±10%, 20%, 30%, 40%, or 50%), about 100 µM DTPA (or 100 µM DTPA±10%, 20%, 30%, 40%, or 50%), about 6% sucrose (or 6% sucrose±10%, 20%, 30%, 40%, or 50%), and about 0.02% PS80 (or 0.02% PS80±10%, 20%, 30%, 40%, or 50%) at about pH 6.0.

In some embodiments, the composition comprises a 1:3 ratio of nivolumab to ipilimumab comprising about 4.62 mg/ml nivolumab, about 1.54 mg/ml ipilimumab, about 18.5 mM Tris Hydrochloride, about 1.5 mM Sodium Citrate Dihydrate, about 96.2 mM NaCl, about 1.2% Mannitol, about 93.9 µM Pentetic Acid, and about 0.012% PS80 at about pH 6.0.

In some embodiments, the composition comprises a 1:3 ratio of nivolumab to ipilimumab comprising about 4.61 mg/ml nivolumab, about 1.54 mg/ml ipilimumab, about 18.46 mM Tris Hydrochloride, about 1.54 mM Sodium Citrate Dihydrate, about 96.15 mM NaCl, about 1.15% Mannitol, about 93.85 µM Pentetic Acid, and about 0.012% PS80 at about pH 6.3.

In some embodiments, the pharmaceutical composition comprises 30 mg of nivolumab and 90 mg of ipilimumab per vial. In other embodiments, the composition comprises 40 mg of nivolumab and 120 mg of ipilimumab per vial.

In other embodiments, the composition comprises a third antibody. In some embodiments, the third antibody is any antibody disclosed herein.

Stability of the Compositions

In one embodiment, a composition disclosed herein is stable at about 0° C., about 5° C., about 10° C., about 15° C., about 20° C., about 25° C., about 30° C., about 35° C., about 40° C., about 45° C., about 50° C., or about 55° C. for at least about 1 week, at least about 2 weeks, at least about 1 month, at least about 2 months, at least about 3 months, at least about 6 months, at least about 9 months, at least about 1 year, at least about 2 years or at least about 5 years.

In another embodiment, composition exhibits a change of the acidic peak (e.g., deamidation) that is less than about 15%, about 14%, about 13%, about 12%, about 11%, about 10%, about 9%, about 8%, about 7%, about 6%, about 5%, about 4%, about 3%, about 2% or about 1% after being stored for about 1 month, about 2 months, about 3 months, about 4 months, about 6 months, or about 1 year at about 5° C. In other embodiments, composition exhibits a change of the acidic peak that is less than about 15%, about 14%, about 13%, about 12%, about 11%, about 10%, about 9%, about 8%, about 7%, about 6%, about 5%, about 4%, about 3%, about 2% or about 1% after being stored for about 1 month, about 2 months, about 3 months, about 4 months, about 6 months, or about 1 year at about 25° C. In some embodiments, composition exhibits a change of the acidic peak that is less than about 15%, about 14%, about 13%, about 12%, about 11%, about 10%, about 9%, about 8%, about 7%, about 6%, about 5%, about 4%, about 3%, about 2% or about 1% after being stored for about 1 month, about 2 months, about 3 months, about 4 months, about 6 months, or about 1 year at about 40° C. In some embodiments, the acidic peak is measured using an Imaged Capillary Isoelectric Focusing assay (cIEF).

In some embodiments, the deamidation of a composition of the present invention is comparable to the deamidation of a reference composition (a composition comprising either the first antibody or the second antibody) if the composition exhibits a change of the acidic peak (e.g., deamidation) that is less than about 15%, about 14%, about 13%, about 12%, about 11%, about 10%, about 9%, about 8%, about 7%, about 6%, about 5%, about 4%, about 3%, about 2% or about 1% compared to the acidic peak of the reference composition.

In certain embodiments, the composition exhibits a change of the high molecular weight (HMW) peak (e.g., aggregation) that is less than about 15%, about 14%, about 13%, about 12%, about 11%, about 10%, about 9%, about 8%, about 7%, about 6%, about 5%, about 4%, about 3%, about 2% or about 1% after being stored for about 1 month, about 2 months, about 3 months, about 4 months, about 6 months, or about 1 year at about 5° C. In some embodiments, the composition exhibits a change of the HMW peak that is less than about 15%, about 14%, about 13%, about 12%, about 11%, about 10%, about 9%, about 8%, about 7%, about 6%, about 5%, about 4%, about 3%, about 2% or about 1% after being stored for about 1 month, about 2 months, about 3 months, about 4 months, about 6 months, or about 1 year at about 25° C. In some embodiments, the composition exhibits a change of the BMW peak that is less than about 15%, about 14%, about 13%, about 12%, about 11%, about 10%, about 9%, about 8%, about 7%, about 6%, about 5%, about 4%, about 3%, about 2% or about 1% after being stored for about 1 month, about 2 months, about 3 months, about 4 months, about 6 months, or about 1 year at about 40° C. In some embodiments, the composition exhibits a change of the HMW peak that is less than about 5%, about 4%, about 3%, about 2%, about 1.5%, about 1.4%, about 1.3%, about 1.2%, about 1.1%, about 1%, about 0.9%, about 0.8%, about 0.7%, about 0.6%, about 0.5%, about 0.4%, about 0.3%, about 0.2%, about 0.1%, or less than about 0.1%. In certain embodiments, the composition exhibits a HMW peak that is about 15%, about 14%, about 13%, about 12%, about 11%, about 10%, about 9%, about 8%, about 7%, about 6%, about 5%, about 4%, about 3%, about 2.5%, about 2%, about 1.5%, about 1%, about 0.9%, about 0.8%, about 0.7%, about 0.6%, about 0.5%, about 0.4%, about 0.3%, about 0.2% or about 0.1% after being stored for about 1 month, about 2 months, about 3 months, about 4 months, about 6 months, or about 1 year at about 5° C., at about 25° C. or at about 40° C. In some embodiments, the high molecular weight peak is measured using chromatography. In some embodiments, the chromatography is size exclusion chromatography.

In some embodiments, the aggregation (e.g., a level of HMW species) of a composition of the present invention is comparable to the aggregation of a reference composition (a composition comprising either the first antibody or the second antibody), if the composition exhibits a change of the BMW species peak that is less than about 15%, about 14%, about 13%, about 12%, about 11%, about 10%, about 9%, about 8%, about 7%, about 6%, about 5%, about 4%, about 3%, about 2% or about 1% compared to the HMW species peak of the reference composition.

In some embodiments, the composition exhibits a change of the main peak that is less than about 15%, about 14%, about 13%, about 12%, about 11%, about 10%, about 9%, about 8%, about 7%, about 6%, about 5%, about 4%, about 3%, about 2% or about 1% after being stored for about 1 month, about 2 months, about 3 months, about 4 months, about 6 months, or about 1 year at about 5° C. In some embodiments, the composition exhibits a change of the main peak that is less than about 15%, about 14%, about 13%, about 12%, about 11%, about 10%, about 9%, about 8%, about 7%, about 6%, about 5%, about 4%, about 3%, about 2% or about 1% after being stored for about 1 month, about 2 months, about 3 months, about 4 months, about 6 months, or about 1 year at about 25° C. In some embodiments, the composition exhibits a change of the main peak that is less than about 15%, about 14%, about 13%, about 12%, about 11%, about 10%, about 9%, about 8%, about 7%, about 6%, about 5%, about 4%, about 3%, about 2% or about 1% after being stored for about 1 month, about 2 months, about 3 months, about 4 months, about 6 months, or about 1 year at about 40° C. In some embodiments, the composition exhibits a change of the main peak that is less than about 5%, about 4%, about 3%, about 2%, about 1.5%, about 1.4%, about 1.3%, about 1.2%, about 1.1%, about 1%, about 0.9%, about 0.8%, about 0.7%, about 0.6%, about 0.5%, about 0.4%, about 0.3%, about 0.2%, or about 0.1%. In some embodiments, the main peak is measured using an Imaged Capillary Isoelectric Focusing assay (cIEF).

In some embodiments, the composition exhibits a change of the low molecular weight (LMW) peak (e.g., fragmentation) that is less than about 15%, about 14%, about 13%, about 12%, about 11%, about 10%, about 9%, about 8%, about 7%, about 6%, about 5%, about 4%, about 3%, about 2% or about 1% after being stored for about 1 month, about 2 months, about 3 months, about 4 months, about 6 months, or about 1 year at about 5° C. In some embodiments, the composition exhibits a change of the LMW peak that is less than about 15%, about 14%, about 13%, about 12%, about 11%, about 10%, about 9%, about 8%, about 7%, about 6%, about 5%, about 4%, about 3%, about 2% or about 1% after being stored for about 1 month, about 2 months, about 3 months, about 4 months, about 6 months, or about 1 year at about 25° C. In some embodiments, the composition exhibits a change of the LMW peak that is less than about 15%, about 14%, about 13%, about 12%, about 11%, about 10%, about 9%, about 8%, about 7%, about 6%, about 5%, about 4%, about 3%, about 2% or about 1% after being stored for about 1 month, about 2 months, about 3 months, about 4 months, about 6 months, or about 1 year at about 40° C. In some embodiments, the composition exhibits a change of the LMW peak that is less than about 5%, about 4%, about 3%, about 2%, about 1.5%, about 1.4%, about 1.3%, about 1.2%, about 1.1%, about 1%, about 0.9%, about 0.8%, about 0.7%, about 0.6%, about 0.5%, about 0.4%, about 0.3%, about 0.2%, or about 0.1%. In certain embodiments, the composition exhibits a LMW peak that is about 15%, about 14%, about 13%, about 12%, about 11%, about 10%, about 9%, about 8%, about 7%, about 6%, about 5%, about 4%, about 3%, about 2.5%, about 2%, about 1.5%, about 1%, about 0.9%, about 0.8%, about 0.7%, about 0.6%, about 0.5%, about 0.4%, about 0.3%, about 0.2% or about 0.1% after being stored for about 1 month, about 2 months, about 3 months, about 4 months, about 6 months, or about 1 year at about 5° C., at about 25° C. or at about 40° C. In some embodiments, the low molecular weight peak is measured using chromatography. In some embodiments, the chromatography is size exclusion chromatography.

In some embodiments, the fragmentation (e.g., a level of LMW species) of a composition of the present invention is comparable to the fragmentation of a reference composition (a composition comprising either the first antibody or the second antibody), if the composition comprising the first and second antibodies exhibits a change of the LMW species peak that is less than about 15%, about 14%, about 13%, about 12%, about 11%, about 10%, about 9%, about 8%, about 7%, about 6%, about 5%, about 4%, about 3%, about 2% or about 1% compared to the LMW species peak of the reference composition.

Method of Making the Compositions Disclosed Herein

In one embodiment, the invention is directed to a method of making any composition disclosed herein. In another embodiment, the formulation comprising the anti-PD-1 antibody drug product is mixed with a formulation comprising the second antibody drug product to obtain the desired ratio in a final drug product with no buffer changes. In other embodiments, the final composition is in Tris-citrate buffer.

In some embodiments, the formulation comprising the anti-PD-1 antibody drug substance and a formulation comprising the second antibody drug substance is subject to buffer exchanges and/or concentration before being mixed to obtain the desired ratio in a final drug product.

In other embodiments, the composition is diluted prior to use. In certain embodiments, the composition is diluted with 0.9% Sodium Chloride Injection, USP or 5% Dextrose Injection, USP prior to use. In other embodiments, the composition is diluted to obtain an infusion with a desired concentration of first and second antibody. In yet other embodiments, the final concentration of first and second antibody is between about 1 mg/ml and about 500 mg/ml, about 1 mg/ml and about 450 mg/ml, about 1 mg/ml and about 400 mg/ml, about 1 mg/ml and about 350 mg/ml, about 1 mg/ml and about 300 mg/ml, about 1 mg/ml and about 250 mg/ml, about 1 mg/ml and about 200 mg/ml, about 1 mg/ml and about 150 mg/ml, about 1 mg/ml and about 100 mg/ml, about 1 mg/ml and about 90 mg/ml, about 1 mg/ml and about 80 mg/ml, about 1 mg/ml and about 70 mg/ml, about 1 mg/ml and about 60 mg/ml, about 1 mg/ml and about 50 mg/ml, about 1 mg/ml and about 40 mg/ml, about 1 mg/ml and about 30 mg/ml, about 1 mg/ml and about 20 mg/ml, about 1 mg/ml and about 15 mg/ml, about 1 mg/ml and about 10 mg/ml, about 1 mg/ml and about 9 mg/ml, about 1 mg/ml and about 8 mg/ml, about 1 mg/ml and about 7 mg/ml, about 1 mg/ml and about 6 mg/ml, about 1 mg/ml and about 5 mg/ml, about 1 mg/ml and about 4 mg/ml, about 1 mg/ml and about 3 mg/ml, about 1 mg/ml and about 2 mg/ml, about 0.5 mg/ml and about 3 mg/ml, about 50 mg/ml and about 400 mg/ml, or about 100 mg/ml and about 300 mg/ml.

In certain embodiments, the diluted infusion is stored for no more than about 10, about 9, about 8, about 7, about 6, about 5, about 4, about 3, about 2 or about 1 hours at room temperature after dilution. In some embodiments, the diluted infusion is store under refrigeration (about 2° C.-about 8° C.) for no more than about 1 week, about 6 days, about 5 days, about 4 days, about 3 days, about 2 days, about 1 day or about 12 hours after dilution.

Methods of the Invention

This disclosure provides a method of treating a subject afflicted with a disease or condition with any composition disclosed herein. In one embodiment, the method is directed to administering a pharmaceutical composition comprising an X amount of a first antibody, which is an anti-PD-1 antibody or an anti-PD-L1 antibody, and a Y amount of a second antibody, wherein the ratio of the amount of the first antibody to the amount of the second antibody is present in a fixed dose ratio of about 100:1 to about 1:100 in the composition.

In some embodiments, the disease or condition is an infectious disease. In other embodiments, the disease or condition is cancer. In still other embodiments, the cancer is melanoma cancer, renal cancer, prostate cancer, breast cancer, colon cancer, lung cancer, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, or any combinations thereof. In yet other embodiments, the cancer is lung cancer, metastatic melanoma, glioblastoma, or renal cell carcinoma.

In certain embodiments, the cancer is squamous cell carcinoma, small-cell lung cancer, non-small cell lung cancer, squamous non-small cell lung cancer (NSCLC), non-squamous NSCLC, glioma, gastrointestinal cancer, renal cancer (e.g. clear cell carcinoma), ovarian cancer, liver cancer, colorectal cancer, endometrial cancer, kidney cancer (e.g., renal cell carcinoma (RCC)), prostate cancer (e.g. hormone refractory prostate adenocarcinoma), thyroid cancer, neuroblastoma, pancreatic cancer, glioblastoma (glioblastoma multiforme), cervical cancer, stomach cancer, bladder cancer, hepatoma, breast cancer, colon carcinoma, and head and neck cancer (or carcinoma), gastric cancer, germ cell tumor, pediatric sarcoma, sinonasal natural killer, melanoma (e.g., metastatic malignant melanoma, such as cutaneous or intraocular malignant melanoma), bone cancer, skin cancer, uterine cancer, cancer of the anal region, testicular cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the parathyroid gland, cancer of the adrenal gland, sarcoma of soft tissue, cancer of the urethra, cancer of the penis, solid tumors of childhood, cancer of the ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally-induced cancers including those induced by asbestos, virus-related cancers (e.g., human papilloma virus (HPV)-related tumor), and hematologic malignancies derived from either of the two major blood cell lineages, i.e., the myeloid cell line (which produces granulocytes, erythrocytes, thrombocytes, macrophages and mast cells) or lymphoid cell line (which produces B, T, NK and plasma cells), such as all types of leukemias, lymphomas, and myelomas, e.g., acute, chronic, lymphocytic and/or myelogenous leukemias, such as acute leukemia (ALL), acute myelogenous leukemia (AML), chronic lymphocytic leukemia (CLL), and chronic myelogenous leukemia (CML), undifferentiated AML (M0), myeloblastic leukemia (M1), myeloblastic leukemia (M2; with cell maturation), promyelocytic leukemia (M3 or M3 variant [M3V]), myelomonocytic leukemia (M4 or M4 variant with eosinophilia [M4E]), monocytic leukemia (M5), erythroleukemia (M6), megakaryoblastic leukemia (M7), isolated granulocytic sarcoma, and chloroma; lymphomas, such as Hodgkin's lymphoma (HL), non-Hodgkin's lymphoma (NHL), B cell hematologic malignancy, e.g., B-cell lymphomas, T-cell lymphomas, lymphoplasmacytoid lymphoma, monocytoid B-cell lymphoma, mucosa-associated lymphoid tissue (MALT) lymphoma, anaplastic (e.g., Ki 1+) large-cell lymphoma, adult T-cell lymphoma/leukemia, mantle cell lymphoma, angio immunoblastic T-cell lymphoma, angiocentric lymphoma, intestinal T-cell lymphoma, primary mediastinal B-cell lymphoma, precursor T-lymphoblastic lymphoma, T-lymphoblastic; and lymphoma/leukaemia (T-Lbly/T-ALL), peripheral T-cell lymphoma, lymphoblastic lymphoma, post-transplantation lymphoproliferative disorder, true histiocytic lymphoma, primary central nervous system lymphoma, primary effusion lymphoma, lymphoblastic lymphoma (LBL), hematopoietic tumors of lymphoid lineage, acute lymphoblastic leukemia, diffuse large B-cell lymphoma, Burkitt's lymphoma, follicular lymphoma, diffuse histiocytic lymphoma (DHL), immunoblastic large cell lymphoma, precursor B-lymphoblastic lymphoma, cutaneous T-cell lymphoma (CTLC) (also called mycosis fungoides or Sezary syndrome), and lymphoplasmacytoid lymphoma (LPL) with Waldenstrom's macroglobulinemia; myelomas, such as IgG myeloma, light chain myeloma, nonsecretory myeloma, smoldering myeloma (also called indolent myeloma), solitary plasmocytoma, and multiple myelomas, chronic lymphocytic leukemia (CLL), hairy cell lymphoma; hematopoietic tumors of myeloid lineage, tumors of mesenchymal origin, including fibrosarcoma and rhabdomyoscarcoma; seminoma, teratocarcinoma, tumors of the central and peripheral nervous, including astrocytoma, schwannomas; tumors of mesenchymal origin, including fibrosarcoma, rhabdomyosarcoma, and osteosarcoma; and other tumors, including melanoma, xeroderma pigmentosum, keratoacanthoma, seminoma, thyroid follicular cancer and teratocarcinoma, hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) preferably of the T-cell type; a/d T-NHL hepatosplenic lymphoma; peripheral/post-thymic T cell lymphoma (pleomorphic and immunoblastic subtypes); angiocentric (nasal) T-cell lymphoma; cancer of the head or neck, renal cancer, rectal cancer, cancer of the thyroid gland; acute myeloid lymphoma, as well as any combinations of said cancers. The methods described herein can also be used for treatment of metastatic cancers.

In certain embodiments, the composition is administered with any additional anti-cancer agent. In other embodiments, the anti-cancer agent is any anti-cancer agent that is known in the art. In yet other embodiments, the anti-cancer agent is a third antibody. In some embodiments, the third antibody is any antibody disclosed herein.

In other embodiments, the composition is administered intravenously. In some embodiments, the composition is reconstituted prior to administration. In yet other embodiments, the composition is diluted prior to administration. In a particular embodiment, the composition is administered at a flat dose. In other embodiments, the composition is administered at a weight-based dose.

In some embodiments, the composition is administered at least about weekly, at least about twice weekly, at least about every two weeks, at least about every three weeks, or at least about monthly. In some embodiments, the treatment lasts for at least about 4 weeks, at least about 8 weeks, at least about 12 weeks, at least about 3 months, at least about 6 months, at least about 9 months, at least about 1 year, at least about 18 months, at least about 2 years or greater than 2 years.

In some embodiments, the invention is directed to a method of modulating the immune response comprising administering any composition disclosed herein.

In certain embodiments, the composition of the present invention (e.g., administration of an anti-PD-1 antibody or the administration of an anti-PD-1 antibody and another anti-cancer therapy) effectively increases the duration of survival of the subject. For example, the duration of survival of the subject is increased by at least about 1 month, at least about 2 months, at least about 3 months, at least about 4 months, at least about 5 months, at least about 6 months, at least about 7 months, at least about 8 months, at least about 9 months, at least about 10 months, at least about 11 months or at least about 1 year or more when compared to another subject treated with only either another therapy (e.g., the standard of care) or only one of the two members of the composition alone (e.g., an anti-PD-1 antibody alone). In some embodiments, the duration of survival is increased by at least about 2 months. In certain embodiments, the therapy of the present invention effectively increases the duration of progression-free survival of the subject. For example, the progression free survival of the subject is increased by at least about 1 month, at least about 2 months, at least about 3 months, at least about 4 months, at least about 5 months, at least about 6 months, at least about 7 months, at least about 8 months, at least about 9 months, at least about 10 months, at least about 11 months or at least about 1 year when compared to an untreated subject or a subject treated only with another therapy (e.g., standard of care treatment) or only one of the two members of the composition alone (e.g., an anti-PD-1 or PD-L1 antibody alone). In some embodiments, the progression-free survival is increased by at least about 2 months. In certain embodiments, the therapy of the present invention effectively increases the response rate in a group of subjects. For example, the response rate in a group of subjects is increased by at least about 2%, at least about 3%, at least about 4%, at least about 5%, at least about 10%, at least about 15%, at least about 20%, at least about 25%, at least about 30%, at last about 35%, at least about 40%, at least about 45%, at least about 50%, at least about 55%, at least about 60%, at least about 70%, at least about 75%, at least about 80%, at least about 85%, at least about 90%, at least about 95%, at least about 99% or at least about 100% when compared to another group of subjects treated with only either another therapy (e.g., the standard of care) or only one of the two members of the composition alone (e.g., an anti-PD-1 antibody alone), i.e., monotherapy.

Dosages of Compositions Disclosed Herein

In some embodiments, the composition is administered at a flat dose regardless of the weight of the patient. For example, the anti-PD-1 antibody with the second antibody may be administered at a flat dose of 0.1, 0.5, 1, 2, 3, 4, 5, 10, 15, 20, 50, 75, 80, 200, 240, 300, 360, 400, 480, 500, 750 or 1500 mg or any other dose disclosed herein, without regard to the patient's weight. In some embodiments, the composition is administered at a weight-based dose at any dose disclosed herein. In some embodiments, the amount of the first antibody and the amount of the second antibody administered to the patient at a single dose are identical the X amount and the Y amount, respectively.

In certain embodiments of the present combination therapy methods, the therapeutically effective dosage of the anti-PD-1 antibody or antigen-binding portion thereof comprises 60 mg, about 80 mg, about 100 mg, about 120 mg, about 140, about 160 mg, about 180 mg, about 200 mg, about 220 mg, about 240 mg, about 260 mg, about 280 mg, or about 300 mg. In some embodiments, the therapeutically effective dosage of the anti-PD-1 antibody or antigen-binding portion thereof comprises about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, or about 500 mg. In some embodiments, the dose of the anti-PD-1 antibody in the composition is between about 60 mg and about 300 mg, between about 60 mg and about 100 mg, between about 100 mg and about 200 mg, or between about 200 mg and about 300 mg. In some embodiments, the dose of the anti-PD-1 antibody in the composition is between about 300 mg and about 500 mg, between about 300 mg and about 450 mg, between about 300 mg and about 400 mg, between about 300 mg and about 350 mg, between about 350 mg and about 500 mg, between about 400 mg and about 500 mg, or between about 450 mg and about 500 mg. In some embodiments, the amount of the anti-PD-1 antibody in the composition is at least about 80 mg, about 160 mg, or about 240 mg. In certain embodiments, the amount of the anti-PD-1 antibody in the composition is at least about 360 mg or 480 mg. In some embodiments, the dose of the anti-PD-1 antibody in the composition is at least about 240 mg or at least about 80 mg. In one embodiment, the amount of the anti-PD-1 antibody in the composition is about 360 mg. In another embodiment, the amount of the anti-PD-1 antibody in the composition is about 480 mg. In some embodiments, the dose of the anti-PD-1 antibody in the composition is a least about 0.5 mg/kg, at least about 1 mg/kg, at least about 2 mg/kg, at least about 3 mg/kg or at least about 5 mg/kg. In some embodiments, the dose of anti-PD-1 antibody in the composition is between about 0.5 mg/kg and about 5 mg/kg, between about 0.5 mg/kg and about 5 mg/kg, between about 0.5 mg/kg and about 3 mg/kg or between about 0.5 mg/kg and about 2 mg/kg. In some embodiments, the dose of the anti-PD-1 antibody in the composition is a least about 1 mg/kg. The corresponding dose of the second antibody is calculated using the desired ratio.

In some embodiments, the anti-PD-1 antibody is administered at a subtherapeutic dose, i.e., a dose of the therapeutic agent that is significantly lower than the usual or FDA-approved dose when administered as monotherapy for the treatment of the cancer. The quantity of the second antibody in the composition is calculated based on the desired ratio. Dosages of nivolumab that are lower than the typical 3 mg/kg, but not less than 0.001 mg/kg, are subtherapeutic dosages. The subtherapeutic doses of an anti-PD-1 antibody used in the methods herein are higher than 0.001 mg/kg and lower than 3 mg/kg. In some embodiments, a subtherapeutic dose is about 0.001 mg/kg-about 1 mg/kg, about 0.01 mg/kg-about 1 mg/kg, about 0.1 mg/kg-about 1 mg/kg, or about 0.001 mg/kg-about 0.1 mg/kg body weight. In some embodiments, the subtherapeutic dose is at least about 0.001 mg/kg, at least about 0.005 mg/kg, at least about 0.01 mg/kg, at least about 0.05 mg/kg, at least about 0.1 mg/kg, at least about 0.5 mg/kg, or at least about 1.0 mg/kg body weight. Receptor-occupancy data from 15 subjects who received 0.3 mg/kg to 10 mg/kg dosing with nivolumab indicate that PD-1 occupancy appears to be dose-independent in this dose range. Across all doses, the mean occupancy rate was 85% (range, 70% to 97%), with a mean plateau occupancy of 72% (range, 59% to 81%). In some embodiments, 0.3 mg/kg dosing can allow for sufficient exposure to lead to maximal biologic activity.

In some embodiments, the composition is administered by intravenous infusion once about per week, once about every 2 weeks, once about every 3 weeks, or once about a month. In certain embodiments, the composition is administered once about every 3 weeks. In one embodiment, 360 mg of the anti-PD-1 antibody or antigen binding fragment is administered once every 3 weeks. In another embodiment, 480 mg of the anti-PD-1 antibody or antigen binding fragment is administered once about once every 4 weeks. In some embodiments, the infusion occurs over at least about 10 minutes, about 20 minutes, about 30 minutes, about 45 minutes, about 60 minutes, about 90 minutes, about 2 hours, about 3 hours, about 4 hours or about 5 hours.

Actual dosage levels of the active ingredients in the pharmaceutical compositions of the present invention can be flat or varied so as to obtain an amount of the active ingredient which is effective to achieve the desired therapeutic response for a particular patient, composition, and mode of administration, without being unduly toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A composition of the present invention can be administered via one or more routes of administration using one or more of a variety of methods well known in the art. As will be appreciated by the skilled artisan, the route and/or mode of administration will vary depending upon the desired results.

Kits

Also within the scope of the present invention are kits comprising an anti-PD-1 antibody/second antibody compositions and instructions for therapeutic uses. Kits typically include a label indicating the intended use of the contents of the kit and instructions for use. The term label includes any writing, or recorded material supplied on or with the kit, or which otherwise accompanies the kit. Accordingly, this disclosure provides a kit comprising: (a) an appropriate dosage of the composition disclosed herein and (b) instructions for using the composition in any of the methods disclosed herein.

The present invention is further illustrated by the following examples which should not be construed as further limiting. The contents of all references cited throughout this application are expressly incorporated herein by reference.

EXAMPLES

Several feasibility studies were performed to evaluate the stability of ipilimumab and nivolumab in a single fixed dose ratio combination (FDRC) formulation. FIG. 1 shows the formulations of ipilimumab and nivolumab in their drug substance (DS) or drug product (DP) formulations, which were used as controls where indicated in the following examples.

Example 1

A feasibility study was performed to evaluate the stability of ipilimumab and nivolumab in a single fixed dose ratio combination (FDRC) formulation created by mixing the individual formulations of ipilimumab and nivolumab (FIG. 1) to a final ratio of ipilimumab to nivolumab of 1:1.

Ipilimumab (BMS-734016) DP contains 5 mg/mL ipilimumab in 20 mM Tris-HCl, 100 mM NaCl, 1.0% (w/v) Mannitol, 100 µM pentetic acid (DTPA), and 0.01% polysorbate 80 (PS80), at pH 7.0, and it is available as 40 mL in a 50 mL bottle and 10 ml in a 10 ml vial (FIG. 1). Nivolumab (BMS-936558) DP contains 10 mg/mL nivolumab in 20 mM citrate buffer (sodium citrate dihydrate), 50 mM NaCl, 3.0% (w/v) Mannitol, 20 µM DTPA, and 0.02% PS80, at pH 6.0, and it is available as 10 mL in a 10 ml vial (FIG. 1).

To achieve a 1:1 ratio of ipilimumab to nivolumab, 80 mL of ipilimumab DP (2 bottles) was mixed with 40 mL of nivolumab DP (4 vials), yielding a combined product having 3.3 mg/mL ipilimumab and 3.3 mg/mL nivolumab. The resulting FDRC formulation contained 13.3 mM Tris-HCl, 6.7 mM citrate, 83.3 mM NaCl, 1.67% (w/v) mannitol, 73.3 µM DTPA, and 0.013% w/v PS80, at pH 6.2 as shown in Table 1.

TABLE 1

Combined EC FDRC (1:1) Formulation

| | | Final Conc'n in Vial: (mg/mL) | | Tris | Citrate | | Mannitol | NaCl | DTPA | PS 80 |
| --- | --- | --- | --- | --- | --- | --- | --- | --- | --- | --- |
| Prototype | Ratio | Ipi (mg/mL) | Nivo (mg/mL) | mM | mM | pH | % w/v | mM | µM | % w/v |
| 1 | 1:1 | 3.3 | 3.3 | 13.3 | 6.7 | 6.2 | 1.67 | 83.3 | 73.3 | 0.013 |

The FDRC (1:1) formulation was filtered and aliquoted into 10 cc glass vials (5 mL per vial), stoppered, and sealed. Vials were then stored at either 5° C. or 40° C. Samples were analyzed at 0 days, 1 week, 2 weeks, 1 month, 2 months, 3 months, and 6 months. Day-0 samples were used a controls.

Sample Analysis—Methods

At each time point, sample vials were analyzed by visual appearance, pH at room temperature, HIAC, size exclusion chromatography, and imaged capillary isoelectric focusing (cIEF). HIAC (Royco) is a light obscuration based particle counting technique instrument.

Size exclusion chromatography (SEC) was performed by analytical size exclusion HPLC (SE-HPLC) using a TSK-GEL® G3000SW$_{XL}$ with a TSKGEL® Guard SW$_{XL}$ guard column on a WATERS® 2695 ALLIANCE® HPLC with a 2497 dual wavelength UV detector using EMPOWER™ 2 Software. The system was equilibrated with 0.1 M NaH$_2$PO$_4$, 0.1 M Na$_2$SO$_4$, and 15% acetonitrile (ACN), at pH 6.8 (mobile phase). Samples were analyzed neat unless the concentration was greater than 125 mg/mL. If the sample concentration was greater than 125 mg/mL, the sample diluted to 50 mg/mL with the corresponding buffer. Samples were transferred to an HPLC vial prior to analysis and stored in the analytical HPLC system at a temperature of 5° C.±3° C. A total of 100 µg of sample were injected for analysis and were run isocratically with a column temperature of 22° C. using the mobile phase. The flow rate was 1.0 mL/min with a run time per sample of 20 min and a detection wavelength of 280 nm.

Imaged capillary isoelectric focusing (cIEF) was performed using a Protein SIMPLE™ iCE3 instrument with an Alcott sampler. Samples were analyzed at a concentration of 25 mg/mL with 2 M urea and 0.35% methyl cellulose (MC). A 50 mm capillary with a 100 µm internal diameter was used to perform separation. The electrolyte solution was 80 mM $H_3PO_4$ in 0.1% MC, and the catholyte solution was 100 mM NaOH in 0.1% MC. The carrier ampholytes were 1% PHARMALYTE® 5-8 and 3% PHARMALYTE® 8-10.5. Focusing time was 13 minutes with focusing voltage starting at 1.5 kV (300 V/cm) for the first minute followed by 3 kV (600V/cm) for the remaining 12 minutes. Detection was performed at 280 nm.

Sample Analysis—Results

SEC was performed on the nivolumab DP and ipilimumab DP controls and the 1:1 ratio fixed dosing combination (EC FDRC (1:1)) formulation following storage for 3 months at 40° C. (FIG. 2A). The nivolumab DP control HMW peak size increased by about 1.6%, and the ipilimumab DP control HMW peak size increased by about 0.25% following storage for 3 months at 40° C. (FIG. 2A). The EC FDRC (1:1) formulation HMW peak size increased by about 0.7% following storage for 3 months at 40° C. (FIG. 2A). Following storage for 6 months at 40° C., the EC FDRC (1:1) formulation HMW peak size increased from 0.555% to a final HMW peak size of 2.82%, an increase of about 2.265% (Table 2). Following storage for 6 months at 5° C., the EC FDRC (1:1) formulation HMW peak size decreased from 0.555% to a final HMW peak size of 0.525% (Table 2).

cIEF was performed on the nivolumab DP and ipilimumab DP controls and the EC FDRC (1:1) formulation following storage for 6 months at 5° C. (FIG. 2B). The nivolumab DP control acidic peak size increased by about 1.3%, and the ipilimumab DP acidic peak size increased by about 3% following storage for 6 months at 5° C. (FIG. 2B).

For the EC FDRC (1:1) formulation, the nivolumab acidic peak size increased by about 3.56%, from 35.09% at day-0 (Initial) to 38.65% at 6 months, while the ipilimumab acidic peak size increased by about 4.16%, from 34% at day-0 (Initial) to 38.16% at 6 months (Table 2 and FIG. 2B).

This study can be used to leverage a broad concentration range of a mixed buffer system, i.e., a Tris-Citrate buffer composition.

Example 2

A feasibility study was performed to evaluate the stability of an ipilimumab/nivolumab FDRC created by mixing the individual formulations of ipilimumab and nivolumab to final ratios of 3:1, 1:1, and 1:3 (Table 3). The FDRC formulations were generated by mixing the ipilimumab DS at 5 mg/mL and nivolumab DS at 20 mg/mL to achieve 3:1, 1:1, and 1:3 protein ratios (Table 3). Each combined solution was further mixed with a stir bar at room temperature for 30 min, transferred to vials, and stored for stability over time. The vials were stored at 5° C., 25° C., and 40° C. for up to 12 months.

TABLE 3

EC FDRC (3:1; 1:1; 1:3) - Combinations of Formulations of Ipilimumab DP and Nivolumab DP

| Prototype | Ratio | Final Conc'n in Vial: (mg/mL) | | pH | Mannitol % w/v | NaCl mM | DTPA µM | PS 80 % w/v |
|---|---|---|---|---|---|---|---|---|
| | | Ipi | Nivo | | | | | |
| EC: pH 6.6 | 3:1 | 4.62 | 1.54 | 6.6 | 1.15 | 96.15 | 93.85 | 0.012 |
| EC: pH 6.0 | 1:3 | 2.86 | 8.57 | 6.0 | 1.86 | 78.57 | 65.71 | 0.023 |
| EC: pH 6.2 | 1:1 | 4.00 | 4.00 | 6.2 | 1.67 | 83.33 | 73.33 | 0.013 |

Prototype EC:pH 6.6, having a 3:1 ratio of ipilimumab to nivolumab, contained 4.62 mg/mL ipilimumab, 1.54 mg/mL nivolumab, 1.15% w/v mannitol, 96.15 mM NaCl, 93.85 µM DTPA, and 0.012% w/v PS80, at pH 6.6. Prototype EC:pH 6.0, having a 1:3 ratio of ipilimumab to nivolumab, contained 2.86 mg/mL ipilimumab, 8.57 mg/mL nivolumab, 1.86% w/v mannitol, 78.57 mM NaCl, 65.71 µM DTPA, and 0.023% w/v PS80, at pH 6.0. Prototype EC:pH 6.2, having a 1:1 ratio of ipilimumab to nivolumab, contained 4.00 mg/mL ipilimumab, 4.00 mg/mL nivolumab, 1.67% w/v mannitol, 83.33 mM NaCl, 73.33 µM DTPA, and 0.013% w/v PS80, at pH 6.2.

TABLE 2

Combined EC FDRC (1:1) Capillary Isoelectric Focusing and Size Exclusion Chromatography results.

| Drug | cIEF Acidic Peak (Initial) | cIEF Acidic Peak (6 M/5 C.) | cIEF Acidic Peak (Change at 5 C.) | SEC HMW initial | SEC HMW 6 M/40 C. | SEC HMW 6 M/5 C. | SEC HMW Change at 40 C. | SEC HMW Change at 5 C. |
|---|---|---|---|---|---|---|---|---|
| Ipilimumab | 34 | 38.16 | 4.16 | 0.555 | 2.82 | 0.525 | 2.265 | −0.03 |
| Nivolumab | 35.09 | 38.65 | 3.56 | | | | | |

SEC Analysis

In general, small increases in HMW and LMW were observed in all 3 prototypes (FIGS. 3A-B). SEC was performed on the nivolumab DP control, the ipilimumab DP control, and the EC FDRC formulations EC:pH 6.0 (1:3), EC:pH 6.2 (1:1), and EC:pH 6.6 (3:1) following storage for 2 months at 40° C. (FIGS. 3A and 3B). The ipilimumab control formulation had an initial HMW peak size of about 0.4% at day 0, which increased by about 0.1% to a final HMW peak size of just over 0.5% after 2 months at 40° C. (FIG. 3A). The nivolumab control formulation had an initial BMW peak size of about 0.8% at day 0, which increased by about 0.7% to a final HMW peak size of over 1.5% after 2 months at 40° C. (FIG. 3A). The EC:pH 6.0 FDRC formulation (1:3) had an initial BMW peak size of about 0.6% at day 0, which increased by about 0.7% to a final BMW peak size of about 1.3% after 2 months at 40° C. (FIG. 3A). The EC:pH 6.2 FDRC formulation (1:1) had an initial HMW peak size of about 0.5% at day 0, which increased by about 0.5% to a final HMW peak size of about 1.0% after 2 months at 40° C. (FIG. 3A). The EC:pH 6.6 FDRC formulation (3:1) had an initial BMW peak size of about 0.5% at day 0, which increased by about 0.3% to a final HMW peak size of about 0.8% after 2 months at 40° C. (FIG. 3A).

The low molecular weight (LMW) peak sizes for the various formulations were also measured at day 0, after 2 months at 40° C., and after 3 months at 25° C. (FIG. 3B). The ipilimumab control formulation had an initial LMW peak size of about 0.2% at day 0, which increased by about 0.65% to a final LMW peak size of about 0.85% after 2 months at 40° C. (FIG. 3B). Following storage at 25° C. for 3 months, the LMW peak size of the ipilimumab control formulation increased by about 0.1% (FIG. 3B). The nivolumab control formulation had an initial LMW peak size of about 0.2% at day 0, which increased by about 0.6% to a final LMW peak size of about 0.8% after 2 months at 40° C. (FIG. 3B). Following storage at 25° C. for 3 months, the LMW peak size of the nivolumab control formulation increased by less than 0.1% (FIG. 3B). The EC:pH 6.0 FDRC formulation (1:3) had an initial LMW peak size of about 0.15% at day 0, which increased by about 0.8% to a final LMW peak size of about 0.95% after 2 months at 40° C. (FIG. 3B). Following storage at 25° C. for 3 months, the LMW peak size of the EC:pH 6.0 (1:3) FDRC formulation increased by about 0.2% (FIG. 3B). The EC:pH 6.2 FDRC formulation (1:1) had an initial LMW peak size of about 0.15% at day 0, which increased by about 1.2% to a final LMW peak size of about 1.35% after 2 months at 40° C. (FIG. 3B). Following storage at 25° C. for 3 months, the LMW peak size of the EC:pH 6.2 (1:1) FDRC formulation increased by about 0.3% (FIG. 3B). The EC:pH 6.6 FDRC formulation (3:1) had an initial LMW peak size of about 0.15% at day 0, which increased by about 1.5% to a final LMW peak size of about 1.65% after 2 months at 40° C. (FIG. 3B). Following storage at 25° C. for 3 months, the LMW peak size of the EC:pH 6.6 (3:1) FDRC formulation increased by about 0.1%.

cIEF Analysis cIEF was performed on the nivolumab DP control, the ipilimumab DP control, and the EC FDRC formulations EC:pH 6.0 (1:3), EC:pH 6.2 (1:1), and EC:pH 6.6 (3:1) following storage for 3 months at 25° C. (FIG. 4A), 3 months at 5° C. (FIG. 4B), and 1 month at 25° C. (FIG. 4C). The nivolumab DP control acidic peak size decreased by about 0.05% and the ipilimumab DP control acidic peak size increased by about 5.59% following storage for 3 months at 25° C. (FIG. 4A). The FDRC formulation EC:pH 6.0 (1:3) nivolumab and ipilimumab acidic peak sizes increased by about 5% and about 5.7%, respectively, following storage for 3 months at 25° C. (FIG. 4A). The FDRC formulation EC:pH 6.2 (1:1) nivolumab and ipilimumab acidic peak sizes increased by about 6.8% and about 6.3%, respectively, following storage for 3 months at 25° C. (FIG. 4A). The FDRC formulation EC:pH 6.6 (3:1) nivolumab and ipilimumab acidic peak sizes increased by about 4% and about 7.8%, respectively, following storage for 3 months at 25° C. (FIG. 4A). Across the three FDRC formulations, the ipilimumab acidic peak size increased by about 5.7%-7.8%, or by an average of about 2.2% per month; and the nivolumab acidic peak size increased by about 4%-6.8%, or by an average of less than 2% (about 1.76%) per month (FIG. 4A).

FIG. 4B shows the actual change in acidic peak size relative to the initial (Day 0) controls for samples stored for 3 months at 5° C. using cIEF analysis. The nivolumab DP control acidic peak size decreased by about 5.1%, and the ipilimumab DP control acidic peak size decreased by about 1% following storage for 3 months at 5° C. (FIG. 4B). The FDRC formulation EC:pH 6.0 (1:3) nivolumab and ipilimumab acidic peak sizes increased by about 0.1% and decreased by about 1.5%, respectively, following storage for 3 months at 5° C. (FIG. 4B). The FDRC formulation EC:pH 6.2 (1:1) nivolumab and ipilimumab acidic peak sizes increased by about 2.1% and about 0.5%, respectively, following storage for 3 months at 5° C. (FIG. 4B). The FDRC formulation EC:pH 6.6 (3:1) showed no change in the ipilimumab acidic peak size and a decrease of less than 0.1% in the nivolumab acidic peak size following storage for 3 months at 5° C. (FIG. 4B).

FIG. 4C shows the actual change in acidic peak size relative to the initial (Day 0) controls for samples stored for 1 month at 25° C. The nivolumab DP control acidic peak size increased by about 1.05%, and the ipilimumab DP control acidic peak size increased by about 1.16% following storage for 1 month at 25° C. (FIG. 4C). The FDRC formulation EC:pH 6.0 (1:3) nivolumab and ipilimumab acidic peak sizes increased by about 2.8% and about 1%, respectively, following storage for 1 month at 25° C. (FIG. 4C). The FDRC formulation EC:pH 6.2 (1:1) nivolumab and ipilimumab acidic peak sizes increased by about 3.1% and about 1.6%, respectively, following storage for 1 month at 25° C. (FIG. 4C). The FDRC formulation EC:pH 6.6 (3:1) nivolumab acidic peak size did not change, and the ipilimumab acidic acid peak size increased by about 2.8% following storage for 1 month at 25° C. (FIG. 4C).

Example 3

A design of experiments (DoE) study was performed to identify new candidate ipilimumab/nivolumab formulations. Prototype ipilimumab/nivolumab FDRC (3:1) formulations were made in selected histidine or citrate formulations, as shown in Table 4. All DoE FDRC prototypes were prepared to a final concentration of ipilimumab/nivolumab of 10 mg/mL at a ratio of 3:1 (Table 4). FDRC prototype "Combo 4" contained 20 mM citrate, 50 mM NaCl, 50 µM DTPA, 6% w/v sucrose, and 0.05% w/v PS80, at a theoretical pH of 6. FDRC prototype "Combo 5" contained 20 mM histidine, 50 mM NaCl, 50 µM DTPA, 6% w/v sucrose, and 0.05% w/v PS80, at a theoretical pH of 6.0. FDRC prototype "Combo 6" contained 20 mM histidine, 50 mM NaCl, 50 µM DTPA, 6% w/v sucrose, and 0.05% w/v PS80, at a theoretical pH of 7. FDRC prototype "Combo New" contained 20 mM histidine, 50 µM DTPA, 8.5% w/v sucrose, and 0.05% w/v PS80, at a theoretical pH of 6. FDRC prototype "Combo 8," which was similar to the current nivolumab DP formulation, contained 20 mM citrate, 50 mM NaCl, 20 µM DTPA, 3% w/v mannitol, and 0.04% w/v PS80, at a theoretical pH of 6.

TABLE 4

DoE FDRC (3:1) - Novel Formulations

| Prototype (3:1) | 20 mM pH Buffer | Concentration mg/mL | NaCl mM | DTPA µM | Sucrose % w/v | Mannitol % w/v | PS80 % w/v |
|---|---|---|---|---|---|---|---|
| Combo 4 | 6 Citrate | 10 | 50 | 50 | 6 | — | 0.05 |
| Combo 5 | 6 Histidine | 10 | 50 | 50 | 6 | — | 0.05 |
| Combo 6 | 7 Histidine | 10 | 50 | 50 | 6 | — | 0.05 |
| Combo new | 6 Histidine | 10 | — | 50 | 8.5 | — | 0.05 |
| Combo 8 | 6 Citrate | 10 | 50 | 20 | — | 3 | 0.04 |

The DoE FDRC formulations were created according to the following example preparation of Combo New. Combo New was prepared by first subjecting ipilimumab DS and nivolumab DS (ELN 96488-024 and -025) to ultrafiltration/diafiltration. In particular, a disposable UFDF cassette was used for nivolumab DS and ipilimumab DS. About 250 mL of the unformulated DS of nivolumab (~21 mg/mL) was used for UF/DF, using the diafiltration/concentration mode. The transmembrane pressure (TMP) was set at 15 psi, while a 0.3 liter per min flow speed was set for feed pump. The diafiltration was completed after 3 liter of the buffer was used. The sample in the vessel was further concentrated based on a scale weight reduction, and collected in 250 PETG bottle. The concentration of nivolumab post UFDF was 30.6 mg/mL. About 500 mL of unformulated DS of ipilimumab (~5.2 mg/mL) was used for UF/DF, using the diafiltration/concentration mode. The ipilimumab concentration in the final product was 16.2 mg/mL by A280.

Next, 20 mL of ipilimumab DS in a histidine-sucrose based buffer and 7.5 mL of nivolumab DS in a histidine-sucrose based buffer were added into D-Tube Dialyzer units and dialyzed against Combo New buffer, as shown in Table 4, for 24 hours in a cold room with sufficient volume (3× change of buffer). The protein concentration of the ipilimumab and nivolumab was then measured by HIAC. Additional ipilimumab DS and/or nivolumab DS and the appropriate buffers were then added to bring the final concentration of ipilimumab to 7.5 mg/mL and nivolumab to 2.5 mg/mL (3:1). The remaining prototypes Combo 4, Combo 5, Combo 6, and Combo 8 were prepared in the same fashion as Combo New, modified to the specific concentrations shown in Table 4.

The combined DP formulations were then filtered and sterile filled into 10 cc vials (SAP #1215125, batch #2L68780), stoppered (SAP #1239068, batch #0H49862), and crimped. Some vials were saved for day-0 control analysis. The rest were put on stability stations at 5° C., 25° C., and 40° C. until vials were pulled at specific time points for analysis.

SEC Analysis

SEC was performed on the nivolumab DP control, the ipilimumab DP control, and the DoE FDRC (3:1) formulations Combo New, Combo 4, Combo 5, Combo 6, and Combo 8 following storage for 3 months at 40° C. (FIG. 5A). The ipilimumab control formulation had an initial HMW peak size of about 0.4% at day 0, which increased by about 0.2% to a final HMW peak size of about 0.6% after 3 months at 40° C. (FIG. 5A). The nivolumab control formulation had an initial HMW peak size of about 0.7% at day 0, which increased by about 1.6% to a final HMW peak size of about 2.4% after 3 months at 40° C. (FIG. 5A). The Combo New FDRC formulation had an initial HMW peak size of about 0.4% at day 0, which increased by about 0.1% to a final HMW peak size of just over 0.5% after 3 months at 40° C. (FIG. 5A). The Combo 4 FDRC formulation had an initial HMW peak size of about 0.6% at day 0, which increased by about 0.7% to a final HMW peak size of about 1.3% after 3 months at 40° C. (FIG. 5A). The Combo 5 FDRC formulation had an initial HMW peak size of just less than 0.5% at day 0, which increased by about 0.3% to a final HMW peak size of less than 0.8% after 3 months at 40° C. (FIG. 5A). The Combo 6 FDRC formulation had an initial HMW peak size of about 0.5% at day 0, which increased by about 0.3% to a final HMW peak size of about 0.8% after 3 months at 40° C. (FIG. 5A). The Combo 8 FDRC formulation had an initial HMW peak size of about 0.5% at day 0, which increased by about 1.0% to a final HMW peak size of about 1.5% after 3 months at 40° C. (FIG. 5A).

The same formulations were analyzed by SEC following storage for 3 months at 25° C. (FIG. 5A). The HMW peak size of the ipilimumab control formulation and the nivolumab control formulation each increased 0.1% or less following storage for 3 months at 25° C. (FIG. 5A). The HMW peak sizes of the Combo New and Combo 8 FDRC formulations each increased by 0.1% or less, and the HMW peak sizes of the Combo 4, Combo 5, and Combo 6 FDRC formulations each decreased by about 0.1% or less following storage for 3 months at 25° C. (FIG. 5A).

cIEF Analysis cIEF was performed on the nivolumab DP control, the ipilimumab DP control, and the DoE FDRC (3:1) formulations Combo New, Combo 4, Combo 5, Combo 6, and Combo 8 following storage for 3 months at 25° C. (FIG. 5B). The ipilimumab control acidic peak size increased by about 5.59%, and the nivolumab DP control acidic peak size decreased by about 0.05% following storage for 3 months at 25° C. (FIG. 5B). The nivolumab and ipilimumab acidic peak sizes of the Combo New FDRC formulation increased by about 0.64% and 5.98%, respectively, following storage for 3 months at 25° C. (FIG. 5B). The nivolumab and ipilimumab acidic peak sizes of the Combo 4 FDRC formulation increased by about 5.32% and 6.97%, respectively, following storage for 3 months at 25° C. (FIG. 5B). The nivolumab and ipilimumab acidic peak sizes of the Combo 5 FDRC formulation increased by about 0.12% and 5.34%, respectively, following storage for 3 months at 25° C. (FIG. 5B). The nivolumab and ipilimumab acidic peak sizes of the Combo 6 FDRC formulation increased by about 7.01% and 12.19%, respectively, following storage for 3 months at 25° C. (FIG. 5B). The nivolumab and ipilimumab acidic peak sizes of the Combo 8 FDRC formulation each increased by about 7.17% following storage for 3 months at 25° C. (FIG. 5B).

Example 4

A feasibility study was performed to evaluate the stability of an ipilimumab/nivolumab FDRC at varying ratios of ipilimumab to nivolumab, using a modified version of the DoE FDRC (3:1) Combo New formulation, characterized in Example 3, as the base formulation. Ipilimumab/nivolumab FDRC platform combined (PC) formulations were made at ratios of ipilimumab to nivolumab of 3:1, 1:3, and 1:1, as shown in Table 5. All formulations were prepared in a histidine buffer and at final concentrations of 50 µM DTPA, 0.05% w/v PS80, and 8.0% w/v sucrose (Table 5). FDRC PC Prototype 4 ("PC:pH 5.5-1:3") had a ratio of 1:3 and a pH of 5.5; FDRC PC Prototype 5 ("PC:pH 6.0-1:3") had a ratio of 1:3 and a pH of 6.0; FDRC PC Prototype 6 ("PC:pH 6.5-1:3") had a ratio of 1:3 and pH of 6.5; FDRC PC Prototype 7 ("PC:pH 6.0-1:1") had a ratio of 1:1 and a pH of 6.0; and FDRC PC Prototype 8 ("PC:pH 6.0-3:1") had a ratio of 3:1 and a pH of 6.0 (Table 5).

TABLE 5

Ipilimumab/Nivolumab FDRC Platform Combined Formulations

| Prototype | Ratio | Final Conc'n in Vial: (mg/mL) | | pH | Mannitol % w/v | NaCl mM | DTPA µM | PS 80 % w/v | Sucrose % w/v |
| --- | --- | --- | --- | --- | --- | --- | --- | --- | --- |
| | | Ipi | Nivo | | | | | | |
| 4 | 1:3 | 2.5 | 7.5 | 5.5 | — | — | 50 | 0.05 | 8.0 |
| 5 | 1:3 | 2.5 | 7.5 | 6.0 | — | — | 50 | 0.05 | 8.0 |
| 6 | 1:3 | 2.5 | 7.5 | 6.5 | — | — | 50 | 0.05 | 8.0 |
| 7 | 1:1 | 5 | 5 | 6.0 | — | — | 50 | 0.05 | 8.0 |
| 8 | 3:1 | 7.5 | 2.5 | 6.0 | — | — | 50 | 0.05 | 8.0 |

SEC Analysis

SEC was performed on the nivolumab DP control, the ipilimumab DP control, and the platform combined (PC) FDRC formulations PC:pH 6.0-1:1, PC:pH 5.5-1:3, PC:pH 6.0-1:3, PC:pH 6.5-1:3, and PC:pH 6.0-3:1 following storage for 3 months at 40° C. (FIG. 6A). The HMW peak sizes of the nivolumab and ipilimumab control formulations increased by about 1.7% and 0.25%, respectively, following storage for 3 months at 40° C. (FIG. 6A). The HMW peak size of the PC:pH 6.0-1:1 FDRC formulation increased by about 0.5% following storage for 3 months at 40° C. (FIG. 6A). The HMW peak size of the PC:pH 5.5-1:3 FDRC formulation increased by about 1.25% following storage for 3 months at 40° C. (FIG. 6A). The HMW peak size of the PC:pH 6.0-1:3 FDRC formulation increased by about 0.75% following storage for 3 months at 40° C. (FIG. 6A). The HMW peak size of the PC:pH 6.5-1:3 FDRC formulation increased by about 0.1% following storage for 3 months at 40° C. (FIG. 6A). The HMW peak size of the PC:pH 6.0-3:1 FDRC formulation increased by about 0.25% following storage for 3 months at 40° C. (FIG. 6A).

The same formulations were analyzed by SEC following storage for 3 months at 5° C. (FIG. 6B). The nivolumab control formulation had an initial HMW peak size of about 0.70% at day 0, which increased to a final HMW peak size of about 0.71% after 3 months at 5° C. (FIG. 6B). The ipilimumab control formulation had an initial HMW peak size of about 0.4% at day 0, which did not change after 3 months at 5° C. (FIG. 6B). The PC:pH 6.0-1:1 FDRC formulation had an initial HMW peak size of about 0.44% at day 0, which increased to a final HMW peak size of about 0.45% after 3 months at 5° C. (FIG. 6B). The PC:pH 5.5-1:3 FDRC formulation had an initial BMW peak size of about 0.47% at day 0, which increased to a final HMW peak size of about 0.48% after 3 months at 5° C. (FIG. 6B). The PC:pH 6.0-1:3 FDRC formulation had an initial HMW peak size of about 0.51% at day 0, which did not change after 3 months at 5° C. (FIG. 6B). The PC:pH 6.5-1:3 FDRC formulation had an initial HMW peak size of about 0.56% at day 0, which increased to a final HMW peak size of about 0.58% after 3 months at 5° C. (FIG. 6B). The PC:pH 6.0-3:1 FDRC formulation had an initial HMW peak size of about 0.37% at day 0, which increased to a final HMW peak size of about 0.39% after 3 months at 5° C. (FIG. 6B).

cIEF Analysis cIEF was performed on the nivolumab DP control, the ipilimumab DP control, and the platform combined (PC) FDRC formulations PC:pH 6.0-1:1, PC:pH 5.5-1:3, PC:pH 6.0-1:3, PC:pH 6.5-1:3, and PC:pH 6.0-3:1 following storage for 3 months at 25° C. (FIG. 7A) and 3 months at 5° C. (FIG. 7B).

Following storage for 3 months at 25° C., the nivolumab control acidic peak size decreased by about 0.05%, and the ipilimumab control acidic peak size increased by about 5.59% (FIG. 7A). The nivolumab and ipilimumab acidic peak sizes of the PC:pH 6.0-1:1 FDRC formulation increased by about 2.6% and 7%, respectively, following storage for 3 months at 25° C. (FIG. 7A). The PC:pH 5.5-1:3 FDRC formulation nivolumab and ipilimumab acidic peak sizes increased by about 2.1% and 5.9%, respectively, following storage for 3 months at 25° C. (FIG. 7A). The PC:pH 6.0-1:3 FDRC formulation nivolumab and ipilimumab acidic peak sizes increased by about 3.7% and 6.8%, respectively, following storage for 3 months at 25° C. (FIG. 7A). The PC:pH 6.5-1:3 FDRC formulation nivolumab and ipilimumab acidic peak sizes increased by about 5.9% and 6.3%, respectively, following storage for 3 months at 25° C. (FIG. 7A). The PC:pH 6.0-3:1 FDRC formulation nivolumab and ipilimumab acidic peak sizes increased by about 1.3% and 6.2%, respectively, following storage for 3 months at 25° C. (FIG. 7A). Across all PC FDRC formulations stored for 3 months at 25° C., the ipilimumab acidic peak size increased by about 5.9-7.0%, or by an average of about 2.0% per month (FIG. 7A). The nivolumab acidic peak size of the FC FDRC formulations increased by about 1.3-5.9%, or at a maximum of about 2% per month (FIG. 7A).

Following storage for 3 months at 5° C., the nivolumab control acidic peak size decreased by about 5.2%, and the ipilimumab control acidic peak size decreased by about 1% (FIG. 7B). The nivolumab and ipilimumab acidic peak sizes of the PC:pH 6.0-1:1 FDRC formulation decreased by about 2% and increased by about 2.2%, respectively, following storage for 3 months at 5° C. (FIG. 7B). The nivolumab and ipilimumab acidic peak sizes of the PC:pH 5.5-1:3 FDRC formulation decreased by about 1.1% and about 0.3%, respectively, following storage for 3 months at 5° C. (FIG. 7B). The nivolumab and ipilimumab acidic peak sizes of the PC:pH 6.0-1:3 FDRC formulation each decreased by about 0.2% following storage for 3 months at 5° C. (FIG. 7B). The nivolumab and ipilimumab acidic peak sizes of the PC:pH 6.5-1:3 FDRC formulation increased by about 0.5% and decreased by about 3.1%, respectively, following storage for 3 months at 5° C. (FIG. 7B). The nivolumab and ipilimumab acidic peak sizes of the PC:pH 6.0-3:1 FDRC formulation increased by about 0.1% and decreased by about 0.2%, respectively, following storage for 3 months at 5° C. (FIG. 7B). In sum, the acidic peak sizes of ipilimumab and nivolumab in the 1:3 formulations across pH 5.5-6.5 showed essentially no change after storage for 3 months at 5° C., and there was no discernable change in ipilimumab and nivolumab across the 3 different ratios (FIG. 7B).

Example 5

A feasibility study was performed to evaluate the stability of an ipilimumab/nivolumab (1:1) FDRC in several nivolumab-DP-based formulations, as shown in Table 6. These formulations were designed through modification of the nivolumab DP formulation (FIG. 1). A total of 24 vials of ipilimumab DP and nivolumab DP were subjected to buffer exchange from their original DP buffer formulations into a buffer formulation containing 20 mM citric acid and 50 mM NaCl at pH 6.0 (Prototype A) using centrifugal filter units with a molecular weight cutoff of 50 kDa. Prototypes B-D were prepared in the same manner to reach the specifications shown in Table 6. Prototype A contained 7.5 mg/mL ipilimumab, 7.5 mg/mL nivolumab, 20 mM citrate, 50 mM NaCl, 3.0% w/v mannitol, 100 µM pentetic acid (DTPA), and 0.02% PS80, at pH 6.0. Prototype A was identical to the nivolumab DP except that Prototype A had 100 µM pentetic acid, whereas the nivolumab DP had 20 µM pentetic acid. Prototype B contained 7.5 mg/mL ipilimumab, 7.5 mg/mL nivolumab, 20 mM citrate, 50 mM NaCl, 3.0% w/v mannitol, 100 µM pentetic acid (DTPA), and 0.02% PS80, at pH 6.5. Prototype C contained 7.5 mg/mL ipilimumab, 7.5 mg/mL nivolumab, 20 mM citrate, 100 mM NaCl, 1.0% w/v mannitol, 100 µM pentetic acid (DTPA), and 0.02% PS80, at pH 6.5. Prototype D contained 7.5 mg/mL ipilimumab, 7.5 mg/mL nivolumab, 20 mM citrate, 50 mM NaCl, 6% w/v sucrose, 100 µM pentetic acid (DTPA), and 0.02% PS80, at pH 6.0.

TABLE 6

Nivolumab-DP-based FDRC (1:1) Formulations

| | |
|---|---|
| Prototype A: | Ipi/Nivo: 7.5 + 7.5 in Citrate (20 mM), pH 6.0, 50 mM NaCl, 3.0% w/v Mannitol, 100 uM Pentetic acid, 0.02% PS80 |
| Prototype B: | Ipi/Nivo: 7.5 + 7.5 in Citrate (20 mM), pH 6.5, 50 mM NaCl, 3.0% w/v Mannitol, 100 uM Pentetic acid, 0.02% PS80 |
| Prototype C: | Ipi/Nivo: 7.5 + 7.5 in Citrate (20 mM), pH 6.5, 100 mM NaCl, 1.0% w/v Mannitol, 100 uM Pentetic acid, 0.02% PS80 |
| Prototype D: | Ipi/Nivo: 7.5 + 7.5 in Citrate (20 mM), pH 6.0, 50 mM NaCl, 6% w/v Sucrose, 100 uM Pentetic acid, 0.02% PS80 |

*Note:
Prototype A is similar to the nivolumab DP formulation except the pentetic acid (DTPA) concentration is the same as in the ipilimumab DP formulation (see FIG. 1).

FDRC prototypes A, B, C, and D were filtered with 0.2 micron unit and filled into 10 cc SCHOTT® vials (1 or 2 mL per vial), stoppered, and sealed. They were then put on stability stations for up to 12 months for stability analysis by appearance, pH, SEC, HIAC, and cIEF.

SEC Analysis

SEC was performed on the nivolumab DP control, the ipilimumab DP control, and the nivolumab-DP-based FDRC (1:1) prototypes A, B, C, and D following storage for 1 month at 40° C. (FIG. 8). The BMW peak sizes of the nivolumab and ipilimumab control formulations increased by about 0.38% and 0.02%, respectively, following storage for 1 month at 40° C. (FIG. 8). The HMW peak size of the FDRC prototype A formulation increased by about 0.36% following storage for 1 month at 40° C. (FIG. 8). The HMW peak size of the FDRC prototype B formulation increased by about 0.41% following storage for 1 month at 40° C. (FIG. 8). The HMW peak size of the FDRC prototype C increased by about 0.37% following storage for 1 month at 40° C. (FIG. 8). The HMW peak size of the FDRC prototype D increased by about 0.24% following storage for 1 month at 40° C. (FIG. 8). The nivolumab control formulation and FDRC prototype A and B formulations each contained 3% w/v mannitol, whereas the ipilimumab control formulation and FDRC prototype C formulation had 1% mannitol and the FDRC prototype D formulation had no mannitol (see Table 6).

cIEF Analysis cIEF was performed on the nivolumab DP control, the ipilimumab DP control, and the nivolumab-DP-based FDRC (1:1) prototype A, B, C, and D formulations following storage for 3 months at 25° C. (FIG. 9). The nivolumab control acidic peak size increased by about 7.5%, and the ipilimumab control acidic peak size increased by about 8.8% following storage for 3 months at 25° C. (FIG. 9). The nivolumab and ipilimumab acidic peak sizes of the FDRC prototype A formulation each increased by about 9.4% following storage for 3 months at 25° C. (FIG. 9). The nivolumab and ipilimumab acidic peak sizes of the FDRC prototype B formulation increased by about 8.2% and 13.8%, respectively, following storage for 3 months at 25° C. (FIG. 9). The nivolumab and ipilimumab acidic peak sizes of the FDRC prototype C formulation increased by about 8.7% and 10.2%, respectively, following storage for 3 months at 25° C. (FIG. 9). The nivolumab and ipilimumab acidic peak sizes of the FDRC prototype D formulation increased by about 10.1% and 9%, respectively, following storage for 3 months at 25° C. (FIG. 9). The effect of NaCl on acidic peak change can be observed by comparing the ipilimumab control formulation and the FDRC prototype C formulation, which each had 100 mM NaCl, to the nivolumab control formulation and the FDRC prototype A, B, and D formulations, which each had 50 mM NaCl (FIG. 9; Table 6).

Example 6

A fixed dose ratio combination (FDRC) drug product of Nivolumab and Ipilimumab was developed in 1:3 ratio. Ipilimumab/nivolumab FDRC was prepared from the commercial drug substance of ipilimumab and nivolumab. See FIG. 1. Ipilimumab drug substance is an aqueous solution containing 5 mg/mL ipilimumab in 20 mM Tris hydrochloride, 100 mM sodium chloride, 1.0% (w/v) mannitol, 100 µM pentetic acid, 0.01% (w/v) polysorbate 80 at pH 7.0. Nivolumab drug substance is an aqueous solution containing 20 mg/mL nivolumab in 20 mM sodium citrate, 50 mM sodium chloride, 3.0% (w/v) mannitol, 20 µM pentetic acid, 0.04% (w/v) polysorbate 80 at pH 6.0. Both the ipilimumab and nivolumab drug substance are stored at 2°-8° C.

The ipilimumab/nivolumab FDRC (3:1) drug product is formulated by combining the ipilimumab and nivolumab drug substances at an ipilimumab to nivolumab protein ratio of 3 to 1. Development stability data up to 6 months showed that the FDRC drug product was stable when stored at 2° to 8° C., the intended storage condition. The FDRC drug product is a sterile, non-pyrogenic, single-use, preservative-free, isotonic aqueous solution for IV administration. The FDRC drug product may be administered undiluted at a total protein concentration of 6.2 mg/mL or further diluted with 0.9% Sodium Chloride Injection, USP or 5% Dextrose Injection, USP to desired concentrations. The FDRC is packaged in a Type I flint glass tubing or molded vial and stoppered with a FLUROTEC® film-coated butyl rubber stopper. The composition of the FDRC is provided in Table 7.

variants detected by CEX or iCIEF) as shown in Examples 1 to 5. These changes were monitored by SE-HPLC and iCIEF in the FDRC The results obtained from the studies showed that in the FDRC DP, the levels of combined BMW species, combined LMW species, acidic charge variants of nivolumab, acidic charge variants of ipilimumab, and particulate matter remained essentially unchanged after 6-months storage at 2° C. to 8° C.

The studies conducted through 6 months under the accelerated condition of 25° C. showed that the rate of formation of BMW species is comparable between the FDRC DP, nivolumab DP, and ipilimumab DP. The rate of formation of LMW species in the FDRC DP is 0.15% per month, which is comparable with that of 0.18% per month in the ipilimumab DP, as the FDRC is primarily composed of ipilimumab. The rate of formation of nivolumab acidic variants in the FDRC DP is 1.98% per month, which is comparable with that of 1.76% per month in the nivolumab DP. The rate of formation of ipilimumab acidic variants in the FDRC and in the ipilimumab DP is considered comparable at 2.4% and 1.9% per month, respectively. The level of particulate matter remained essentially unchanged.

The studies conducted through 3-months storage at 40° C. showed that similar but greater changes were observed in the FDRC DP under the condition.

TABLE 7

Comparison of the Compositions of the FDRC, Ipilimumab, and Nivolumab Drug Products

| Component | Function | Quantity (Concentration) | | | Unit |
| --- | --- | --- | --- | --- | --- |
| | | FDRC | Ipilimumab | Nivolumab | |
| Ipilimumab (BMS-734016) | Active ingredient | 4.62 | 5 | — | mg/mL |
| Nivolumab (BMS-936558) | Active ingredient | 1.54 | — | 10 | mg/mL |
| Tris Hydrochloride | Buffering agent | 18.5 | 20 | — | mM |
| Sodium Citrate, Dihydrate | Buffering agent | 1.5 | — | 20 | mM |
| Sodium Chloride | Tonicity modifier | 96.2 | 100 | 50 | mM |
| Mannitol | Tonicity modifier | 1.2 | 1.0 | 3.0 | % (w/v) |
| Pentetic Acid[1] | Metal ion chelator | 93.9 | 100.0 | 20.0 | µM |
| Polysorbate 80 | Surfactant | 0.012 | 0.010 | 0.020 | % (w/v) |
| pH at 20° to 25° C.[2] | pH adjustment | 6.0 | 7.0 (at 4° C.) | 6.0 | pH unit |
| Water for Injection | Solvent | q.s. | | | |

[1]Also known as diethylenetriaminepentaacetic acid (DTPA)
[2]Diluted solutions of hydrochloric acid and sodium hydroxide may be used for pH adjustment during ipilimumab and nivolumab DS manufacturing. Solution pH is not adjusted during DP manufacturing development stability study. In addition, the particulate matter and binding activities were monitored by HIAC and ELISA binding, respectively, in these studies at designated time points.

The stability of the FDRC DP samples prepared as shown in Table 7 was monitored under intended (5° C.), accelerated (25° C.), and stressed (40° C.) storage conditions.

The major degradation pathways of ipilimumab and nivolumab were identified to be aggregation (HMW species detected by SE-HPLC), fragmentation (LMW species detected by SE-HPLC), and deamidation (acidic charge The use-time study data demonstrate the stability, compatibility, and equivalence of the dosing solutions prepared from the FDRC DP and from combining individual nivolumab and ipilimumab DPs in an IV bag.

In summary, comparable formation rates of critical quality attributes (CQAs) such as HMW species, LMW species, and acidic variants at stressed and accelerated conditions and negligible changes in these CQAs at the recommended storage condition indicate the potential for developing a FDRC DP with the commercialized DS of nivolumab and ipilimumab. Each of the above listed studies are shown in more detail below:

Aggregation and Fragmentation Detected by SE-HPLC

The extent of aggregation (HMW species) and fragmentation (LMW species) of the FDRC was examined by SE-HPLC. The HMW species, monomer, and LMW species of ipilimumab co-elute with the HMW species, monomer, and LMW species of nivolumab, respectively. The results presented in Table 8 are reported as the area percent of combined monomer, combined HMW species, and combined LMW species of ipilimumab and nivolumab. The level of combined HMW species was tested 0.5% initially and remained essentially unchanged through 6 months of storage at 5° C. and 25° C. (ranged 0.5 to 0.6%) and increased to 1.0% through 3 months of storage at 40° C. The level of combined LMW species was tested 0.1% initially and remained essentially unchanged through 6 months of storage at 5° C. (ranged 0.1 to 0.2%), increased to 1.0% through 6 months of storage at 25° C., and increased to 2.4% through 3 months of storage at 40° C.

TABLE 8

Combined Monomer, HMW Species, and LMW Species in the FDRC Detected by SE-HPLC

| Time | Combined Monomer (%) | | | Combined HMW Species (%) | | | Combined LMW Species (%) | | |
|---|---|---|---|---|---|---|---|---|---|
| (Month) | 5° C. | 25° C. | 40° C. | 5° C. | 25° C. | 40° C. | 5° C. | 25° C. | 40° C. |
| Initial | 99.3 | 99.3 | 99.3 | 0.5 | 0.5 | 0.5 | 0.1 | 0.1 | 0.1 |
| 1 | NT | 99.3 | 98.9 | NT | 0.6 | 0.6 | NT | 0.2 | 0.4 |
| 2 | 99.3 | 99.2 | 97.5 | 0.5 | 0.5 | 0.8 | 0.2 | 0.3 | 1.7 |
| 3 | 99.3 | 98.8 | 96.7 | 0.5 | 0.6 | 1.0 | 0.2 | 0.6 | 2.4 |
| 6 | 99.3 | 98.4 | NT | 0.6 | 0.7 | NT | 0.2 | 1.0 | NT |

NT = not tested

These results were compared with ipilimumab (5 mg/mL) and nivolumab (10 mg/mL) commercial DP formulation controls placed on station at 5° C., 25° C. and 40° C. along with FDRC DP analyzed in a similar manner with this modified SEC-HPLC method as shown in Table 9 and 10 respectively. Based on the data available it is evident that both ipilimumab, nivolumab and FDRC are not prone to formation of HMW species at the recommended storage temperature of 2-8° C.; and the rate of formation of HMW species/month is comparable between ipilimumab, nivolumab and FDRC at 25° C. and 40° C. conditions as shown in Table 11. More importantly, the rates of formation of HMW and LMW species in FDRC are equivalent to rates of formation of HMW & LMW species in ipilimumab, as the FDRC is predominantly composed of ipilimumab and the total protein concentration in FDRC i.e., 6.2 mg/mL is very close to ipilimumab DP concentration of 5 mg/mL. Comparable formation rates of CQA's such as HMW and LMW species at stressed and accelerated conditions and negligible change in these CQA's at recommended storage conditions indicate the potential for a development for FDRC DP.

TABLE 9

Monomer, HMW Species, and LMW Species in Ipilimumab Detected by SE-HPLC

| Time | Monomer (%) | | | HMW Species (%) | | | LMW Species (%) | | |
|---|---|---|---|---|---|---|---|---|---|
| (Month) | 5° C. | 25° C. | 40° C. | 5° C. | 25° C. | 40° C. | 5° C. | 25° C. | 40° C. |
| Initial | 99.38 | 99.38 | 99.38 | 0.4 | 0.4 | 0.4 | 0.22 | 0.22 | 0.22 |
| 1 | 99.37 | 99.33 | 98.98 | 0.4 | 0.38 | 0.42 | 0.23 | 0.29 | 0.6 |
| 2 | 99.39 | 99.26 | 98.54 | 0.39 | 0.395 | 0.51 | 0.22 | 0.325 | 0.955 |
| 3 | 99.37 | 99.16 | 96.65 | 0.4 | 0.43 | 0.635 | 0.23 | 0.415 | 2.54 |
| 6 | 99.29 | 98.62 | NT | 0.475 | 0.535 | NT | 0.245 | 1.32 | NT |

TABLE 10

Monomer, HMW Species, and LMW Species in Nivolumab Detected by SE-HPLC

| Time (Month) | Monomer (%) 5° C. | Monomer (%) 25° C. | Monomer (%) 40° C. | HMW Species (%) 5° C. | HMW Species (%) 25° C. | HMW Species (%) 40° C. | LMW Species (%) 5° C. | LMW Species (%) 25° C. | LMW Species (%) 40° C. |
|---|---|---|---|---|---|---|---|---|---|
| Initial | 98.99 | 98.99 | 98.99 | 0.705 | 0.705 | 0.705 | 0.315 | 0.315 | 0.315 |
| 1 | 98.98 | 98.94 | 98.35 | 0.705 | 0.73 | 1.115 | 0.32 | 0.33 | 0.55 |
| 2 | 98.98 | 98.91 | 97.56 | 0.705 | 0.76 | 1.595 | 0.305 | 0.34 | 0.81 |
| 3 | 98.98 | 98.79 | 96.45 | 0.715 | 0.815 | 2.37 | 0.31 | 0.395 | 1.18 |
| 6 | 98.91 | 98.14 | NT | 0.795 | 0.965 | NT | 0.3 | 0.425 | NT |

TABLE 11

Rate of formation/month of Monomer, HMW Species, and LMW Species in Ipilimumab, Nivolumab and FDRC as detected by SEHPLC

| Time (Month) | Monomer (%) 5° C. | Monomer (%) 25° C. | Monomer (%) 40° C. | HMW Species (%) 5° C. | HMW Species (%) 25° C. | HMW Species (%) 40° C. | LMW Species (%) 5° C. | LMW Species (%) 25° C. | LMW Species (%) 40° C. |
|---|---|---|---|---|---|---|---|---|---|
| FDRC | 0.00 | 0.16 | 0.92 | 0.02 | 0.03 | 0.17 | 0.02 | 0.15 | 0.82 |
| Ipilimumab | 0.01 | 0.13 | 0.86 | 0.01 | 0.02 | 0.08 | 0.00 | 0.18 | 0.73 |
| Nivolumab | 0.01 | 0.14 | 0.84 | 0.02 | 0.04 | 0.55 | 0.00 | 0.02 | 0.29 |

Charge Variants Detected by iCIEF

The charge variant profile of the FDRC was determined by iCIEF analysis. Ipilimumab and nivolumab peaks are separated in the chromatographic profile. The relative amount of the acidic peak areas, main peak area, and basic peak areas of ipilimumab are provided in Table 12 and the relative amount of the acidic peak areas, main peak area, and basic peak areas of nivolumab are provided in Table 13. The acidic, main, and basic peak areas of both ipilimumab and nivolumab remained essentially unchanged through 6 months of storage at 5° C. Changes to the charge profile were observed at 25 C and 40 C for both ipilimumab and nivolumab. Degradation was significant at 40° C. within a very short duration and hence not used for comparison and considered too aggressive for evaluation of DP stability.

TABLE 12

Charge Profile of Ipilimumab in the FDRC Detected by iCIEF

| Time (Month) | Acidic Peaks (%) 5° C. | Acidic Peaks (%) 25° C. | Acidic Peaks (%) 40° C. | Main Peak (%) 5° C. | Main Peak (%) 25° C. | Main Peak (%) 40° C. | Basic Peaks (%) 5° C. | Basic Peaks (%) 25° C. | Basic Peaks (%) 40° C. |
|---|---|---|---|---|---|---|---|---|---|
| Initial | 34.6 | 34.6 | 34.6 | 59.5 | 59.5 | 59.5 | 5.9 | 5.9 | 5.9 |
| 1 | NT | 37.2 | 48.7 | NT | 56.7 | 45.2 | NT | 6.2 | 6.1 |
| 2 | 34.5 | 39.6 | 61.2 | 57.9 | 54.5 | 33.7 | 7.6 | 5.9 | 5.1 |
| 3 | 34.6 | 42.4 | 68.3 | 59.2 | 51.9 | 27.4 | 6.2 | 5.7 | 4.3 |
| 6 | 35.6 | 49.0 | NT | 59.0 | 45.9 | NT | 5.4 | 5.1 | NT |

TABLE 13

Charge Profile of Nivolumab in the FDRC Detected by iCIEF

| Time (Month) | Acidic Peaks (%) 5° C. | Acidic Peaks (%) 25° C. | Acidic Peaks (%) 40° C. | Main Peak (%) 5° C. | Main Peak (%) 25° C. | Main Peak (%) 40° C. | Basic Peaks (%) 5° C. | Basic Peaks (%) 25° C. | Basic Peaks (%) 40° C. |
|---|---|---|---|---|---|---|---|---|---|
| Initial | 33.7 | 33.7 | 33.7 | 59.8 | 59.8 | 59.8 | 6.5 | 6.5 | 6.5 |
| 1 | NT | 34.3 | 45.0 | NT | 59.8 | 46.3 | NT | 5.9 | 8.7 |
| 2 | 34.8 | 39.1 | 61.3 | 59.3 | 54.5 | 31.2 | 5.9 | 6.5 | 7.5 |
| 3 | 33.6 | 37.7 | 65.9 | 60.6 | 55.2 | 27.9 | 5.9 | 7.1 | 6.2 |
| 6 | 33.7 | 45.5 | NT | 59.3 | 46.4 | NT | 7.1 | 8.1 | NT |

Moreover, as discussed earlier the FDRC composition evaluated above is composed of tris.HCl and sodium citrate dihydrate, and hence prone to pH changes with temperature because of the amine buffer Tris-HCl. Hence, charge profile changes between FDRC and nivolumab were conducted at 25° C., to be consistent with sample preparation temperature and storage temperature.

Comparison of ipilimumab acidic charge profile in FDRC shown in Table 12 against ipilimumab control DP in Tris-HCl buffer (commercial composition) at pH 7 (4° C.) at 25° C. condition (Table 14) has indicated that the acidic peak formation is comparable at 2.4% and 1.93%/month respectively as shown in FIG. 10. This relatively minor difference at stressed conditions is considered insignificant for the FDRC drug product stability at the recommended storage conditions (2-8° C.) as observed in Table 12.

Historically, changes in ipilimumab charge profile have been monitored by CEX and hence data is being collected to identify the comparability of the charge profile at various conditions for ipilimumab, however, the potential for deamidation, the primary degradation pathway for ipilimumab, is potentially decreased since deamidation kinetics are usually slower at lower pH.

TABLE 14

Charge Profile of Ipilimumab by iCIEF at 25 C.

| Time (Month) | Acidic Peaks (%) Lab Stability Batch | Main Peak (%) Lab Stability Batch | Basic Peaks (%) Lab Stability Batch |
|---|---|---|---|
| Initial | 39.71 | 56.59 | 3.69 |
| 1 | 42.34 | 54.84 | 2.82 |
| 3 | 45.3 | 51.2 | 3.5 |
| 6 | 51.6 | 45 | 3.4 |

Comparison of nivolumab acidic charge profile in FDRC shown in Table 15 against three nivolumab long term stability batches (LTSB) at 25° C. condition has indicated that the acidic peak formation is comparable at 1.97% and 1.75%/month respectively as shown in FIG. 11.

TABLE 15

Charge Profile of Nivolumab (in GMP Batches) by iCIEF at 25° C.

| | Acidic Peaks (%) | | | Main Peak (%) | | | Basic Peaks (%) | | |
|---|---|---|---|---|---|---|---|---|---|
| Time (Month) | Lot 2J71008 | Lot 2J71191 | Lot 2J71192 | Lot 2J71008 | Lot 2J71191 | Lot 2J71192 | Lot 2J71008 | Lot 2J71191 | Lot 2J71192 |
| Initial | 36.1 | 36.3 | 35.2 | 58.1 | 56.6 | 58.8 | 5.8 | 7.1 | 6.0 |
| 1 | 33.0 | 29.6 | 36.2 | 61.8 | 62.9 | 57.2 | 5.2 | 7.5 | 6.6 |
| 3 | 40.8 | 39.3 | 37.2 | 52.9 | 52.4 | 55.6 | 6.3 | 8.3 | 7.2 |
| 6 | 45.7 | 44.1 | 44.3 | 46.4 | 47.2 | 47.8 | 7.9 | 8.7 | 7.9 |

Particulate Matter Detected by HIAC

Samples stored at 5° and 25° C. for up to 6 months were examined using light obscuration particle count procedure (HIAC) to determine the size and number of particles according to size in the FDRC DP. As shown in Table 16, particulate matter values for ≥2 microns, ≥5 microns, ≥10 microns, and ≥25 microns were variable, but were well within the acceptance criteria outlined in USP <787>.

TABLE 16

Particulate Matter by HIAC

| | Particulate Matter (Particles/mL) | | | |
|---|---|---|---|---|
| | ≥2 μm | ≥5 μm | ≥10 μm | ≥25 μm |
| Initial | 161 | 21 | 5 | 0 |
| 6 Months at 5° C. | 134 | 43 | 13 | 2 |
| 6 Months at 25° C. | 174 | 34 | 6 | 1 |

Binding Activity Determined by ELISA Assays

ELISA assays were utilized to examine the specific binding of ipilimumab to human CTLA-4 receptor and the specific binding of nivolumab to human PD-1 receptor. The binding activities of ipilimumab and nivolumab in the FDRC samples were calculated relative to the ipilimumab and nivolumab reference standards, respectively. The binding activities of the FDRC samples through 2 months of storage at 25° C. were within the proposed acceptance criterion (70 to 130%) (Table 17).

TABLE 17

Binding Activities Determined by ELISA Assays

| Storage Condition | Ipilimumab Binding Activity Relative to Ipilimumab Reference Standard (%) | Nivolumab Binding Activity Relative to Nivolumab Reference Standard (%) |
|---|---|---|
| Initial | 87 | 119 |
| 2 Months at 25° C. | 87 | 78 |

Tryptic Peptide Mapping Assay

A tryptic peptide mapping assay was performed to measure deamidation and oxidation. Samples were reduced, alkylated and digested with trypsin. The tryptic peptides were separated on a C-18 column and detected by a UV detector at 215 and 280 nm, followed by a mass spectrometer (LTQ-Orbitrap-Elite). Relative quantitation was achieved by comparing peak areas of the intact peptides as well as the modified peptides in selected ion chromatograms. The results of the assay are shown in Tables 18 and 19.

TABLE 18

Tryptic Peptide Mapping - Deamidation

| Storage Condition | Nivo H$_4$[3] (%) | Ipi H$_5$[4] (%) | Ipi H37/Nivo H36 Deam1[5] (%) | Ipi H37/Nivo H36 Deam2[6] (%) | Ipi H37/Nivo H36 Deam3[7] (%) | Ipi H37/Nivo H36 Deam4[8] (%) |
|---|---|---|---|---|---|---|
| Initial | 0.5 | 2.8 | 3.4 | 3.2 | 1.4 | 3.6 |
| 2 Months at 25° C. | 0.7 | 4.6 | 4.7 | 4.6 | 1.5 | 3.7 |
| 6 Months at 25° C. | 1.0 | 3.9 | 5.2 | 5.9 | 0.7 | 2.5 |

[3]Nivo H$_4$ = Heavy Chain Tryptic Peptide # 4 for nivolumab
[4]Ipi H$_5$ = Heavy Chain Tryptic Peptide # 5 for ipilimumab
[5]Ipi H$_{37}$/Nivo H$_{36}$ Deam1 = Heavy Chain Tryptic Peptide # 37 for ipilimumab (Asn # ) and #36 for nivolumab (Asn #)
[6]Ipi H$_{37}$/Nivo H$_{36}$ Deam2 = Heavy Chain Tryptic Peptide #37 for ipilimumab (Asn # ) and #36 for nivolumab (Asn #)
[7]Ipi H$_{37}$/Nivo H$_{36}$ Deam3 = Heavy Chain Tryptic Peptide #37 for ipilimumab (Asn # ) and #36 for nivolumab (Asn #)
[8]Ipi H$_{37}$/Nivo H$_{36}$ Deam4 = Heavy Chain Tryptic Peptide #37 for ipilimumab (Asn # ) and #36 for nivolumab (Asn #)

TABLE 19

Tryptic Peptide Mapping - Oxidation

| Storage Condition | Ipi H$_{21}$/Nivo H$_{22}$[9] (%) | Nivo H4[10] (%) | Ipi H$_3$[11] (%) |
|---|---|---|---|
| Initial | 4.4 | 0.2 | 0.5 |
| 2 Months at 25° C. | 4.9 | 0.6 | 0.5 |
| 6 Months at 25° C. | 3.3 | 0.3 | 0.2 |

[9]Ipi H$_{21}$/Nivo H$_{22}$ = Heavy Chain Tryptic Peptide # 21 for ipilimumab (His/Met #) and #22 for nivolumab (His/Met #)
[10]Nivo H$_4$ = Heavy Chain Tryptic Peptide # 4 for nivolumab
[11]Ipi H$_3$ = Heavy Chain Tryptic Peptide # 3 for ipilimumab pH Analysis of Samples The pH of the FDCR DP was measured, as seen in Table 20.

TABLE 20 pH of the DP Solutions

| Storage Condition | 25° C. | 5° C. |
|---|---|---|
| Initial | 6.58 | 6.58 |
| 2 Months | 6.59 | 6.56 |
| 6 Months | 6.44 | 6.38 |

Use-Time Stability of the FDRC Drug Product

A study was performed to demonstrate the stability and compatibility of the FDRC DP with 0.9% Sodium Chloride Injection, USP (NS), IV bags, IV infusion sets, and in-line filters. After 2 months of storage at 5° C., the FDRC DP samples were diluted into NS in an IV bag which was stored at 25° C. for 4 hours followed by 20 hours at 5° C. The solution in the IV bag was then infused through an IV set and an in-line filter. Samples were collected and analyzed by HIAC, micro flow imaging (MFI), SE-HPLC, CE-SDS, iCIEF, and reverse phase ultra performance liquid chromatography (RP-UPLC).

The results of the study are presented in Tables 21-23. The data show little or no change from the initial values for particulate matter (by HIAC), aggregation (by SE-HPLC), fragmentation (by (SE-HPLC), purity (by CE-SDS), charge variant profile (by iCIEF), and ipilimumab/nivolumab protein ratio (by RP-UPLC) after completion of the compatibility study.

The results indicate that the FDRC DP can be diluted with 0.9% Sodium Chloride Injection, USP to a concentration range of 1.5/0.5 to 4.2/1.4 mg/mL ipilimumab/nivolumab for IV infusion. The diluted solution in an IV bag may be stored at 5° C. for up to 24 hours and up to 4 hours of the 24 hours may be at room temperature (25° C.).

TABLE 21

Use-Time Stability and Comparability of the FDRC Drug Product

| | Condition | | | | | | | | | | |
|---|---|---|---|---|---|---|---|---|---|---|---|
| | HIAC (Particles/mL) | | | | MFI (Particles/mL) | | | SE-HPL | | | CE-SDS (Reduced) |
| | ≥2 µm | ≥5 µm | ≥10 µm | ≥25 µm | 2-10 µm | ≥10 µm | ≥25 µm | HMW (%) | Monomer (%) | LMW (%) | Purity (%) |
| 1.5/0.5 mg/mL ipilimumab/nivolumab | | | | | | | | | | | |
| Initial[12] | 138 | 26 | 5 | 0 | 353 | 11.5 | 0 | 0.4 | 99.4 | 0.3 | 99.6 |
| 24 hours[13] | 213 | 52 | 14 | 0 | 414 | 18 | 1.6 | 0.3 | 99.3 | 0.4 | 99.6 |

TABLE 21-continued

Use-Time Stability and Comparability of the FDRC Drug Product

| | Condition | | | | | | | | | | |
|---|---|---|---|---|---|---|---|---|---|---|---|
| | HIAC (Particles/mL) | | | | MFI (Particles/mL) | | | SE-HPL | | | CE-SDS (Reduced) |
| | ≥2 µm | ≥5 µm | ≥10 µm | ≥25 µm | 2-10 µm | ≥10 µm | ≥25 µm | HMW (%) | Monomer (%) | LMW (%) | Purity (%) |
| 4.2/1.4 mg/mL ipilimumab/nivolumab | | | | | | | | | | | |
| Initial | 345 | 77 | 24 | 1 | 888 | 6.5 | 0 | 0.4 | 99.3 | 0.3 | 99.6 |
| 24 hours | 193 | 36 | 12 | 1 | 455 | 0 | 0 | 0.4 | 99.3 | 0.3 | 99.6 |

[12] Samples collected from a IV bag at time zero after dilution of the FDRC DP in the IV bag
[13] Samples collected after 24-hours storage and infusion through an IV set and an in-line filter

TABLE 22

Use-Time Stability and Comparability of the FDRC Drug Product

| | iCIEF-Ipilimumab | | | iCIEF-Nivolumab | | | |
|---|---|---|---|---|---|---|---|
| Condition | Acidic Peaks (%) | Main Peak (%) | Basic Peaks (%) | Acidic Peaks (%) | Main Peak (%) | Basic Peaks (%) | RP-UPLC Ipilimumab/Nivolumab Protein Ratio |
| 1.5/0.5 mg/mL ipilimumab/nivolumab | | | | | | | |
| Initial | 38.9 | 56.2 | 4.9 | 34.3 | 57.5 | 8.3 | 2.8 |
| 24 hours | 38.0 | 56.8 | 5.1 | 34.2 | 57.7 | 8.1 | 2.8 |
| 4.2/1.4 mg/mL ipilimumab/nivolumab | | | | | | | |
| Initial | 37.2 | 58.1 | 4.7 | 34.2 | 58.0 | 7.8 | 2.9 |
| 24 hours | 37.9 | 57.2 | 4.9 | 34.8 | 57.9 | 7.3 | 2.8 |

TABLE 23

Use-Time Stability and Comparability of the FDRC Drug Product

| Condition | A280 (Traditional) | A280 (Solo-VPE) | pH |
|---|---|---|---|
| 1.5/0.5 mg/mL ipilimumab/nivolumab | | | |
| Initial | 2.07 | 1.998 | 6.36 |
| 24 hours | 1.924 | 2.012 | 6.33 |
| 4.2/1.4 mg/mL ipilimumab/nivolumab | | | |
| Initial | 5.618 | 5.615 | 6.38 |
| 24 hours | 5.529 | 5.647 | 6.37 |

Use-Time Stability of the Co-administered Ipilimumab and Nivolumab Drug Product

A study was performed to demonstrate the stability and compatibility of the co-administered DP with 0.9% Sodium Chloride Injection, USP (NS), IV bags, IV infusion sets, and in-line filters. Ipilimumab and nivolumab monotherapy DP vials were diluted into NS in an IV bag which was stored at 25° C. for 4 hours followed by 20 hours at 5° C. The solution in the IV bag was then infused through an IV set and an in-line filter. Samples were collected and analyzed by HIAC, micro flow imaging (WI), SE-HPLC, CE-SDS, iCIEF, and reverse phase ultra performance liquid chromatography (RP-UPLC).

The results of the study are presented in Tables 24-26. The data show little or no change from the initial values for particulate matter (by HIAC), aggregation (by SE-HPLC), fragmentation (by SE-HPLC), purity (by CE-SDS), charge variant profile (by iCIEF), and ipilimumab/nivolumab protein ratio (by RP-UPLC) after completion of the compatibility study. The results indicate that the co-administered DP can be diluted with 0.9% Sodium Chloride Injection, USP to a concentration range of 1.5/0.5 to 4.2/1.4 mg/mL ipilimumab/nivolumab for IV infusion. The diluted solution in an IV bag may be stored at 5° C. for up to 24 hours and up to 4 hours of the 24 hours may be at room temperature (25° C.).

TABLE 24

Use-Time Stability and Comparability of the Co-administered Ipilimumab and Nivolumab Drug Product

| | HIAC (Particles/mL) | | | | MFI (Particles/mL) | | | SE-HPLC | | | CE-SDS (Reduced) |
|---|---|---|---|---|---|---|---|---|---|---|---|
| Condition | ≥2 µm | ≥5 µm | ≥10 µm | ≥25 µm | 2-10 µm | ≥10 µm | ≥25 µm | HMW (%) | Monomer (%) | LMW (%) | Purity (%) |
| 1.5/0.5 mg/mL ipilimumab/nivolumab (Non-DEHP Intravia bags) | | | | | | | | | | | |
| Initial[14] | 327 | 75 | 10 | 0 | 1078 | 8 | 1 | 0.3 | 99.4 | 0.2 | 99.6 |
| 24 hours[15] | 49 | 9 | 1 | 0 | 152 | 3 | 1 | 0.3 | 99.4 | 0.3 | 99.6 |

TABLE 24-continued

Use-Time Stability and Comparability of the Co-administered Ipilimumab and Nivolumab Drug Product

| Condition | HIAC (Particles/mL) ≥2 μm | ≥5 μm | ≥10 μm | ≥25 μm | MFI (Particles/mL) 2-10 μm | ≥10 μm | ≥25 μm | SE-HPLC HMW (%) | Monomer (%) | LMW (%) | CE-SDS (Reduced) Purity (%) |
|---|---|---|---|---|---|---|---|---|---|---|---|
| \multicolumn{12}{l}{1.5/0.5 mg/mL ipilimumab/nivolumab (DEHP Viaflex bags)} |
| Initial | 373 | 54 | 8 | 0 | 1233 | 2 | 0 | 0.4 | 99.3 | 0.3 | 99.6 |
| 24 hours | 35 | 5 | 1 | 0 | 71 | 5 | 1 | 0.4 | 99.4 | 0.3 | 99.6 |
| \multicolumn{12}{l}{4.2/1.4 mg/mL ipilimumab/nivolumab (Non-DEHP Intravia bags)} |
| Initial | 862 | 170 | 17 | 0 | 2979 | 8 | 1 | 0.4 | 99.3 | 0.3 | 99.6 |
| 24 hours | 112 | 21 | 3 | 0 | 237 | 8 | 0 | 0.4 | 99.4 | 0.3 | 99.6 |
| \multicolumn{12}{l}{4.2/1.4 mg/mL ipilimumab/nivolumab (DEHP Viaflex bags)} |
| Initial | 431 | 91 | 15 | 0 | 1400 | 11 | 1 | 0.4 | 99.4 | 0.3 | 99.6 |
| 24 hours | 53 | 11 | 4 | 0 | 150 | 3 | 1 | 0.4 | 99.4 | 0.3 | 99.6 |

[14] Samples collected from a IV bag at time zero after dilution of the co-administered DP in the IV bag
[15] Samples collected after 24-hours storage and infusion through an IV set and an in-line filter

TABLE 25

Use-Time Stability and Comparability of the Co-administered Ipilimumab and Nivolumab Drug Product

| Condition | iCIEF-Ipilimumab Acidic Peaks (%) | Main Peak (%) | Basic Peaks (%) | iCIEF-Nivolumab Acidic Peaks (%) | Main Peak (%) | Basic Peaks (%) | RP-UPLC Ipilimumab/Nivolumab Protein Ratio |
|---|---|---|---|---|---|---|---|
| \multicolumn{8}{l}{1.5/0.5 mg/mL ipilimumab/nivolumab (Non-DEHP Intravia bags)} |
| Initial | 36.3 | 59.9 | 3.8 | 35.9 | 59.1 | 5.0 | 2.85 |
| 24 hours | 36.2 | 59.9 | 3.9 | 33.8 | 60.7 | 5.5 | 2.80 |
| \multicolumn{8}{l}{1.5/0.5 mg/mL ipilimumab/nivolumab (DEHP Viaflex bags)} |
| Initial | 36.8 | 59.8 | 3.4 | 35.2 | 58.6 | 6.2 | 2.87 |
| 24 hours | 36.2 | 60.1 | 3.7 | 35.3 | 58.3 | 6.4 | 2.79 |
| \multicolumn{8}{l}{4.2/1.4 mg/mL ipilimumab/nivolumab (Non-DEHP Intravia bags)} |
| Initial | 36.6 | 59.8 | 3.6 | 34.1 | 59.8 | 6.1 | 2.9 |
| 24 Hours | 36.9 | 59.5 | 3.6 | 33.6 | 60.4 | 6.0 | 2.87 |
| \multicolumn{8}{l}{4.2/1.4 mg/mL ipilimumab/nivolumab (DEHP Viaflex bags)} |
| Initial | 36.3 | 59.9 | 3.8 | 36.0 | 57.3 | 6.7 | 2.93 |
| 24 hours | 36.7 | 59.5 | 3.8 | 35.2 | 58.6 | 6.2 | 2.92 |

TABLE 26

Use-Time Stability and Comparability of the Co-administered Ipilimumab and Nivolumab Drug Product

| Condition | A280 (Traditional) | A280 (Solo-VPE) | pH |
|---|---|---|---|
| \multicolumn{4}{l}{1.5/0.5 mg/mL ipilimumab/nivolumab (Non-DEHP Intravia bags)} |
| Initial | 1.994 | 1.941 | 6.21 |
| 24 hours | 1.898 | 1.936 | 6.19 |
| \multicolumn{4}{l}{1.5/0.5 mg/mL ipilimumab/nivolumab (DEHP Viaflex bags)} |
| Initial | 2.019 | 1.982 | 6.2 |
| 24 hours | 1.879 | 1.986 | 6.2 |
| \multicolumn{4}{l}{4.2/1.4 mg/mL ipilimumab/nivolumab (Non-DEHP Intravia bags)} |
| Initial | 5.701 | 5.481 | 6.26 |
| 24 hours | 5.338 | 5.538 | 6.24 |
| \multicolumn{4}{l}{4.2/1.4 mg/mL ipilimumab/nivolumab (DEHP Viaflex bags)} |
| Initial | 5.586 | 5.509 | 6.26 |
| 24 hours | 5.363 | 5.499 | 6.26 |

Example 7

The process performance qualification (PPQ) limits for pH and Polysorbate 80 in a Nivolumab-Ipilimumab 1:3 Fixed dose ratio combination (FDRC) for nivolumab-Ipilimumab 1:3 fixed dose ratio combination were determined. The quantitative compositions of the FDRC drug product are seen in Table 27.

TABLE 27

Quantitative Compositions of the FDRC Drug Product

| Component | Function | Composition | Quantity (mg) Per Vial (Nivolumab/Ipilimumab) 30/90 | 40/120 |
|---|---|---|---|---|
| Nivolumab (BMS-936558) | Active ingredient | 1.54 mg/mL | 31.11 | 41.58 |
| Ipilimumab (BMS-734016) | Active ingredient | 4.61 mg/mL | 93.32 | 124.74 |
| Sodium Citrate, Dihydrate | Buffering agent | 1.54 mM | 9.15 | 12.23 |
| Tris Hydrochloride | Buffering agent | 18.46 mM | 58.76 | 78.55 |
| Sodium Chloride | Tonicity modifier | 96.15 mM | 113.50 | 151.71 |
| Mannitol | Tonicity modifier | 1.15% w/v | 232.30 | 310.50 |
| Pentetic Acid[16] | Metal ion chelator | 93.85 μM | 0.75 | 1.00 |
| Polysorbate 80 | Surfactant | 0.012% w/v | 2.42 | 3.24 |
| Hydrochloric Acid Sodium Hydroxide[17] | pH adjustment | | q.s. to pH 6.3 | |
| Water for Injection | Solvent | | q.s. to 20.2 mL | q.s. to 27.0 mL | q.s. = quantity sufficient pH limit

[16] Also known as diethylenetriaminepentaacetic acid

[17] Diluted solutions of hydrochloric acid and sodium hydroxide may be used for pH adjustment during nivolumab and ipilimumab DS manufacturing. Solution pH is not adjusted during FDRC DP manufacturing manipulation to the incoming DS, a study was conducted to understand the potential range of pH in FDRC DP due to the incoming DS variability.

Commercial ipilimumab DS and nivolumab DS have a pH acceptance criteria of 6.6-7.6 (4° C.) & 5.5-6.5 respectively. Since, the FDRC DP is manufactured without any further

TABLE 28

Variability in FDRC DP pH due to incoming DS variability

| 20 mM Tris-HCl | 20 mM Sodium Citrate | Final pH pH (4° C.) | pH (21° C.) |
|---|---|---|---|
| pH 6.6 | pH 5.5 | 5.77 | 5.64 |
| pH 7.0 | pH 6.0 | 6.47 | 6.32 |
| pH 7.6 | pH 6.5 | 7.34 | 6.99 |

The solutions were prepared by adding 42 mL of 20 mM Tris-HCl and 3.5 mL 20 mM Sodium Citrate buffer to mimic FDRC DP preparation. The results of this evaluation (Table 28) indicated that the pH range of FDRC DP could be in the range of 5.7-7.0, with a target pH of 6.2-6.3 at ambient conditions. This attribute is well controlled in the incoming DS of nivolumab and ipilimumab, hence it is unlikely that the pH extremes of 5.7 or 7.0 will be ever experienced by the FDRC DP. Additionally, based on the current knowledge of CQAs of ipilimumab and nivolumab, the risk to FDRC DP quality attributes is expected to be higher at the higher pH range. Based on this understanding, two additional studies were initiated to evaluate the impact of pH on DP quality attributes and also to understand the impact of variability in various excipients (including pH) from incoming DS on DP quality attributes.

Evaluation of the data from the pH ranging study was focused on the quality attributes in FDRC impacted by variation in pH such as charge profile monitored by capillary isoelectric focusing (icIEF) and high molecular weight aggregates monitored by size exclusion chromatography (SEC). There is no discernible change in SEC profile of FDRC DP across the pH range of 5.4-6.6 (ambient) at the recommended storage conditions of 2-8° C. or up to 3 months at 25° C. Quantifiable changes were only observed at accelerated conditions (40° C.), where it was evident that the evaluated pH range has no impact on SEC profile (Table 29).

TABLE 29

Monomer, HMW, and LMW Species (%) due to variability in pH

| DP Prototype (pH) | HMW Species (%) Initial | 1 M/40° C. | 3 M/40° C. | Monomer (%) Initial | 1 M/40° C. | 3 M/40° C. | LMW Species (%) Initial | 1 M/40° C. | 3 M/40° C. |
|---|---|---|---|---|---|---|---|---|---|
| 5.4 | 1.12 | 1.25 | 1.79 | 98.7 | 98.2 | 96.8 | 0.1 | 0.53 | 1.35 |
| 5.7 | 1.19 | 1.24 | 1.69 | 98.7 | 98.3 | 97.1 | 0.1 | 0.46 | 1.16 |
| 6.0 | 1.23 | 1.24 | 1.65 | 98.6 | 98.3 | 97.2 | 0.1 | 0.43 | 1.07 |
| 6.3 | 1.24 | 1.2 | 1.63 | 98.6 | 98.3 | 97.3 | 0.1 | 0.42 | 1.04 |
| 6.6 | 1.33 | 1.33 | 1.7 | 98.6 | 98.2 | 97.2 | 0.1 | 0.43 | 1.05 |

The charge profile of ipilimumab and nivolumab did not shown any significant differences beyond analytical error at the recommended storage temperature of 2-8° C. after 6 months as shown in Table 30. Charge profile for ipilimumab and nivolumab is primarily evaluated at the storage temperature of 25° C. as the differences are more discernible, unlike 40° C., where the profile is dramatically altered and the molecules significantly fall apart. FIG. 12 illustrates the acidic profile of ipilimumab and nivolumab in FDRC DP in comparison with their respective controls at pH 6.0.

TABLE 30

Acidic & Main Peak Profile (cIEF) due to variability in pH after 6 Months at 5° C.

| DP Proto-type (pH) | Acidic Peak Profile (%) (% Change from Initial after 6M at 5° C.) | | Main Peak Change (%) (% Change from Initial after 6M at 5° C.) | |
|---|---|---|---|---|
| | Ipilimumab | Nivolumab | Ipilimumab | Nivolumab |
| 5.4 | −1.0 | −0.3 | −1.0 | −0.4 |
| 5.7 | 0.6 | −3.7 | 1.4 | −1.8 |
| 6.0 | 0.6 | −1.5 | 0.8 | −1.2 |
| 6.3 | 0.9 | −2.3 | 1.5 | −1.6 |
| 6.6 | 1.1 | −1.9 | 1.6 | −0.7 |

Additionally, a pH ruggedness study initiated with the variables shown in Table 31, where the pH range evaluated was varied between 5.8-7.0 has resulted in similar observations for SEC and cIEF profiles.

TABLE 31

DP Ruggedness Study Design

| Prototype | Final Conc'n in Vial: (mg/mL) | | pH | Tris mM | Citrate mM | NaCl mM | Mannitol % w/v | PS 80 % w/v | DTPA μM |
|---|---|---|---|---|---|---|---|---|---|
| | Ipilimumab (mg/mL) | Nivolumab (mg/mL) | | | | | | | |
| 1 | 4.62 | 1.54 | 5.8 | 18.46 | 1.54 | 76.92 | 1.38% | 0.005 | 93.85 |
| 2 | 4.62 | 1.54 | 5.8 | 18.46 | 1.54 | 115.38 | 1.38% | 0.020 | 93.85 |
| 3 | 4.62 | 1.54 | 5.8 | 18.46 | 1.54 | 76.92 | 0.92% | 0.020 | 93.85 |
| 4 | 4.62 | 1.54 | 6.4 | 18.46 | 1.54 | 96.15 | 1.15% | 0.012 | 93.85 |
| 5 | 4.62 | 1.54 | 7 | 18.46 | 1.54 | 115.38 | 1.38% | 0.005 | 93.85 |
| 6 | 4.62 | 1.54 | 7 | 18.46 | 1.54 | 76.92 | 0.92% | 0.005 | 93.85 |
| 7 | 4.62 | 1.54 | 6.4 | 18.46 | 1.54 | 96.15 | 1.15% | 0.012 | 93.85 |
| 8 | 4.62 | 1.54 | 5.8 | 18.46 | 1.54 | 115.38 | 0.92% | 0.005 | 93.85 |
| 9 | 4.62 | 1.54 | 7 | 18.46 | 1.54 | 115.38 | 0.92% | 0.020 | 93.85 |
| 10 | 4.62 | 1.54 | 7 | 18.46 | 1.54 | 76.92 | 1.38% | 0.020 | 93.85 |

The HMW profile of the FDRC DP remained unchanged after 6 months of storage at 2-8° C. and 25° C. as shown in FIG. 13 (Monomer Profile seen in FIG. 14), indicating the lack of pH effect even in the presence of other variables such as the concentration of sodium chloride, Mannitol and PS80. Evaluation of acidic and main peak profiles of ipilimumab and nivolumab in FDRC DP (FIG. 15-18) clearly indicates a pH dependence of deamidation at accelerated temperature of 25° C., as indicated by an increase in acidic peak profile at higher temperature range of pH 7.0. This effect at accelerated temperatures, however, does not translate into a quantifiable difference at the recommended storage temperature of 2-8° C.

The cIEF Peak Profile and the impact of pH are shown in FIG. 19, and the iCIEF Profile: pH range of 5.4-6.6 are shown in FIG. 20.

Polysorbate 80 Limit: NLT 60 μg/mL

Polysorbate 80 concentration in the FDRC DP is primarily defined by the proportion of ipilimumab and nivolumab DS mixed to manufacture the FDRC DP, where the target concentration of PS 80 in FDRC DP is 120 μg/mL, with a nominal concentration 100 μg/mL and 400 μg/mL for ipilimumab and nivolumab DS respectively. There are no release acceptance criteria for PS 80 for both nivolumab and ipilimumab DS; however, the nivolumab DS and ipilimumab DS manufacture has an in-process limit of 275-525 μg/mL and 60-140 μg/mL respectively.

Preliminary analysis of the DP attributes that are impacted by variability of PS80 such as the SEC HMW (%) had no discernible change (FIG. 13) and particulates by HIAC in the range of 10-25 micron range, met the current USP acceptance criteria. Additionally, the FDRC DP manufacturing process is designed so that there is no need for a filter flush prior to DP vial filling, due to the presence of an intermediate tank (35-40 L) downstream of the redundant sterile filters, which is filled prior to initiating the filling operation.

Additionally, during DP optimization studies, a PS 80 concentration range of 120 μg/ml-1000 μg/ml was evaluated in the FDRC DP under worst case of agitation at 300 rpm for up to 72 hours on a horizontal shaker. These studies when analyzed by visual appearance showed the lack of any visual particulates after 72 hours and the SEC profile for all prototypes had no discernible difference from initial time point. Based on this, it was decided to not change the target concentration of FDRC DP by spiking with concentrated PS 80 concentration at the DP manufacturing site.

However, in order to understand the potential risk of particulate generation or HMW species formation because of significantly lower PS80 levels upon dilution with infusion solutions like saline, a study was conducted where FDRC DP solution with PS 80 at target concentration of 120 μg/ml was subjected to 20 fold dilution (6 μg/mL) with normal saline, and the resulting solutions were evaluated for up to 24 hours by visual appearance, particulates by HIAC and SEC HMW (%). This study demonstrated that down to a 6 μg/ml PS 80 concentration in infusion solutions prepared from FDRC DP does not cause any change in visual appearance, HMW profile or HIAC characteristics of the solution, which strengthened the rationale to maintain the target concentration at 120 μg/ml. Additionally, it is anticipated that the FDRC DP will be diluted ~3× using infusion solutions, during clinical and commercial administration which leads to a PS 80 concentration of 40 μg/ml. The proposed PS 80 concentration of NLT of 60 μg/ml would still result in a final infusion solution concentration of 20 μg/ml, which is above the evaluated concentration of 6 μg/ml in the dilution study discussed above.

What is claimed is:

1. A method of treating a cancer in a patient in need thereof comprising administering to the patient a pharmaceutical composition comprising about 1.54 mg/ml nivolumab, about 4.62 mg/ml ipilimumab, about 18.46 mM Tris hydrochloride (HCl), about 1.54 mM sodium citrate dihydrate, about 1.15% mannitol, about 96.15 mM NaCl, about 93.85 pentetic acid, and about 0.012% PS80; wherein the cancer comprises a lung cancer, a metastatic melanoma, or a renal cell carcinoma.

2. The method of claim 1, wherein the composition:
(i) is stable at about 5° C. for at least about 1 week;
(ii) is stable at about 40° C. for at least about 1 week; or
(iii) is stable at about 25° C. for at least about 1 week.

3. The method of claim 1, wherein the pH of the composition is about 6.0, about 6.2, about 6.5, about 6.6, or about 7.0.

4. The method of claim 1, wherein the pH of the composition is about 6.2.

5. The method of claim 1, wherein the pH of the composition is 6.2.

6. The method of claim 1, wherein the pH of the composition is 6.1.

7. The method of claim 1, wherein the composition comprises 1.54 mg/mL nivolumab and 4.62 mg/ml ipilimumab.

8. The method of claim 1, wherein the composition comprises about 30 mg nivolumab and about 90 mg ipilimumab.

9. The method of claim 1, wherein the composition comprises about 40 mg nivolumab and about 120 mg ipilimumab.

10. The method of claim 1, wherein the composition comprises 18.46 mM Tris hydrochloride (HCl).

11. The method of claim 1, wherein the composition comprises 1.54 mM sodium citrate dihydrate.

12. The method of claim 1, wherein the composition comprises 1.15% mannitol.

13. The method of claim 1, wherein the composition comprises 96.15 mM NaCl.

14. The method of claim 1, wherein the composition comprises 93.85 pentetic acid.

15. The method of claim 1, wherein the composition comprises 0.012% PS80.

16. The method of claim 1, wherein the composition comprises 18.46 mM Tris hydrochloride (HCl) and 1.54 mM sodium citrate dihydrate.

17. The method of claim 1, wherein the composition comprises 1.15% mannitol, 96.15 mM NaCl, and 93.85 μM pentetic acid.

18. The method of claim 1, wherein the composition comprises 18.46 mM Tris hydrochloride (HCl), 1.54 mM sodium citrate dihydrate, 1.15% mannitol, 96.15 mM NaCl, and 93.85 µM pentetic acid.

19. The method of claim 1, wherein the composition comprises 18.46 mM Tris hydrochloride (HCl), 1.54 mM sodium citrate dihydrate, 1.15% mannitol, 96.15 mM NaCl, 93.85 µM pentetic acid, and 0.012% PS80.

20. The method of claim 19, wherein the pH is 6.2 at 25° C.

21. The method of claim 1, wherein the pH of the composition is between about 6.0 and about 7.0.

22. The method of claim 1, wherein the composition:
(i) is stable at 5° C. for at least 1 week;
(ii) is stable at 40° C. for at least 1 week; or
(iii) is stable at 25° C. for at least 1 week.

23. A method of treating a cancer in a patient in need thereof comprising administering to the patient a pharmaceutical composition comprising 1.54 mg/ml nivolumab, 4.62 mg/ml ipilimumab, 18.46 mM Tris hydrochloride (HCl), 1.54 mM sodium citrate dihydrate, 1.15% mannitol, 96.15 mM NaCl, 93.85 µM pentetic acid, and 0.012% PS80; wherein the cancer comprises a lung cancer, a metastatic melanoma, or a renal cell carcinoma.

24. The method of claim 23, wherein the pH of the composition is between about 6.0 and about 7.0.

25. The method of claim 23, wherein the pH of the composition is 6.2 at 25° C.

26. The method of claim 23, wherein the composition:
(i) is stable at 5° C. for at least 1 week;
(ii) is stable at 40° C. for at least 1 week; or
(iii) is stable at 25° C. for at least 1 week.

27. The method of claim 23, wherein the composition comprises about 30 mg nivolumab and about 90 mg ipilimumab.

28. The method of claim 23, wherein the composition comprises about 40 mg nivolumab and about 120 mg ipilimumab.

29. The method of claim 1, wherein the lung cancer comprises non-small cell lung cancer (NSCLC).

* * * * *